US012178707B2

(12) United States Patent
Kartholl et al.

(10) Patent No.: US 12,178,707 B2
(45) Date of Patent: Dec. 31, 2024

(54) ELBOW JOINT PROSTHESES

(71) Applicant: HOWMEDICA OSTEONICS CORP., Mahwah, NJ (US)

(72) Inventors: Matthew Victor Kartholl, Fort Wayne, IN (US); Brad Alan Parker, Warsaw, IN (US); Kevin Alika Farley, Leesburg, IN (US); Ryan D. Koepke, Fort Wayne, IN (US)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 0 days.

(21) Appl. No.: 18/526,442

(22) Filed: Dec. 1, 2023

(65) Prior Publication Data

US 2024/0091017 A1 Mar. 21, 2024

Related U.S. Application Data

(60) Continuation of application No. 17/583,886, filed on Jan. 25, 2022, now Pat. No. 11,865,009, which is a
(Continued)

(51) Int. Cl.
  *A61F 2/38* (2006.01)
  *A61F 2/46* (2006.01)
  *A61F 2/30* (2006.01)

(52) U.S. Cl.
  CPC .............. *A61F 2/3804* (2013.01); *A61F 2/38* (2013.01); *A61F 2/4637* (2013.01); *A61F 2002/30383* (2013.01); *A61F 2002/30494* (2013.01); *A61F 2002/30495* (2013.01); *A61F 2002/30528* (2013.01); *A61F 2002/30602* (2013.01); *A61F 2002/3809* (2013.01);
(Continued)

(58) Field of Classification Search
  CPC .... A61F 2/3804; A61F 2/4637; A61F 2/4605; A61F 2002/30383; A61F 2002/30494; A61F 2002/30495; A61F 2002/30528; A61F 2002/30602; A61F 2002/3809; A61F 2002/3813; A61F 2002/3827
  See application file for complete search history.

(56) References Cited

U.S. PATENT DOCUMENTS

| 4,106,128 A | 8/1978 | Greenwald et al. |
| 4,242,750 A | 12/1980 | Finck et al. |
(Continued)

FOREIGN PATENT DOCUMENTS

| CN | 1086120 A | 5/1994 |
| CN | 1177469 A | 4/1998 |
(Continued)

OTHER PUBLICATIONS

Australian Patent Application No. 2018249496, filed Oct. 2, 2019, 65 pages.
(Continued)

*Primary Examiner* — Bruce E Snow
(74) *Attorney, Agent, or Firm* — DUANE MORRIS LLP

(57) ABSTRACT

A radial head assembly is provided that includes a collar, an articular member, an articular head component, and stem that is configured to engage the articular head component. The articular member at least partially defines an articular space within the collar when disposed in the collar.

19 Claims, 34 Drawing Sheets

Related U.S. Application Data division of application No. 17/279,846, filed as application No. PCT/US2019/052852 on Sep. 25, 2019, now Pat. No. 11,266,507.

(60) Provisional application No. 62/740,790, filed on Oct. 3, 2018.

(52) U.S. Cl.
CPC ............ *A61F 2002/3813* (2013.01); *A61F 2002/3827* (2013.01); *A61F 2/4605* (2013.01)

(56) References Cited

U.S. PATENT DOCUMENTS

| | | | |
|---|---|---|---|
| 4,383,337 A | 5/1983 | Volz et al. | |
| 4,798,610 A | 1/1989 | Averill et al. | |
| 5,782,923 A | 7/1998 | Engelbrecht et al. | |
| 5,824,108 A | 10/1998 | Huebner | |
| 5,879,395 A | 3/1999 | Tornier et al. | |
| 6,132,467 A | 10/2000 | Keller | |
| 6,206,929 B1 | 3/2001 | Ochoa et al. | |
| 6,361,563 B2 | 3/2002 | Terrill-Grisoni et al. | |
| 6,379,387 B1 | 4/2002 | Tornier | |
| 6,767,368 B2 | 7/2004 | Tornier | |
| 6,890,357 B2 * | 5/2005 | Tornier | A61F 2/3804 623/20.12 |
| 7,160,329 B2 | 1/2007 | Cooney, III et al. | |
| 7,740,661 B2 * | 6/2010 | Baratz | A61F 2/3804 623/20.11 |
| 7,922,728 B2 | 4/2011 | Tornier et al. | |
| 7,942,882 B2 | 5/2011 | Tornier et al. | |
| RE42,805 E | 10/2011 | Tornier et al. | |
| 8,048,162 B2 * | 11/2011 | Scheker | A61F 2/3804 623/20.11 |
| 8,110,005 B2 | 2/2012 | Berelsman et al. | |
| 8,361,158 B2 | 1/2013 | Smirthwaite et al. | |
| 8,603,182 B2 | 12/2013 | Lambert et al. | |
| 8,636,801 B2 | 1/2014 | Hassler et al. | |
| 8,709,089 B2 | 4/2014 | Lang et al. | |
| 9,023,110 B2 | 5/2015 | Wendelburg et al. | |
| 9,155,626 B2 * | 10/2015 | Huebner | A61F 2/3804 |
| 9,289,304 B1 | 3/2016 | Kaufmann | |
| 2005/0043806 A1 | 2/2005 | Cook et al. | |
| 2006/0064173 A1 | 3/2006 | Guederian | |
| 2006/0116771 A1 | 6/2006 | Cooney, III et al. | |
| 2006/0142866 A1 | 6/2006 | Baratz et al. | |
| 2007/0073409 A1 | 3/2007 | Cooney et al. | |
| 2008/0288079 A1 | 11/2008 | Leibel | |
| 2009/0240336 A1 * | 9/2009 | Vander Meulen | A61F 2/3804 623/18.11 |
| 2011/0166663 A9 * | 7/2011 | Scheker | A61F 2/3804 623/20.11 |
| 2012/0022664 A1 | 1/2012 | Vander et al. | |
| 2014/0012388 A1 | 1/2014 | Brownhill et al. | |
| 2014/0074246 A1 | 3/2014 | Huebner et al. | |
| 2016/0051365 A1 | 2/2016 | Brownhill et al. | |
| 2018/0280150 A1 | 10/2018 | Kartholl et al. | |

FOREIGN PATENT DOCUMENTS

| | | |
|---|---|---|
| DE | 4331282 A1 | 3/1995 |
| EP | 0394545 | 10/1990 |
| JP | 2008521557 | 6/2008 |
| WO | 2010012007 A2 | 1/2010 |
| WO | 2018187233 A1 | 10/2018 |
| WO | 2020072247 | 4/2020 |

OTHER PUBLICATIONS

First Examination Report issued in connection with Australian Patent Application No. 2021240214, Mar. 6, 2023, 6 pages.

International Search Report and Written Opinion issued in connection with International Patent Application No. PCT/US2022/070268, Apr. 7, 2022, 10 pages.

International Search Report and Written Opinion issued in connection with International Patent Application No. PCT/US2022/070264, Apr. 1, 2022, 10 pages.

Non-Final Office Action issued in connection with U.S. Appl. No. 17/372,955, filed May 1, 2024, 10 pages.

Latitude Total Elbow Prosthesis, Surgical Technique, Tornier, 2004, 40 pages.

Latitude EV Total Elbow Prosthesis Surgical Technique, Tornier 2013, 32 pages.

First Office Action issued in connection with corresponding Chinese Patent Application No. 201880029429.X, Mar. 24, 2021, 8 pages.

Latitude EV Total Elbow Arthoplasty, Surgical Technique, Wright, Oct. 2017.

International Search Report and Written Opinion issued in connection with International Patent Application No. PCT/US2018/025737, Sep. 12, 2018, 20 pages.

Amis et al., "Elbow Joint Force Predictions for Some Strenous Isometric Actions", J. Biomech., 1980, vol. 13, pp. 765-775.

Latitude Total Elbow Prosthesis, Surgical Technique, Tornier.

Latitude EV Total Elbow Prosthesis, Surgical Technique, Tornier.

Morrey et al., "Force Transmission through the Radial Head", J. Bone and Joint Surg., Feb. 1988, 70-A, pp. 250-256.

Surgical Technique Total Elbow Prosthesis, Latitude, Tornier Surgical Implants, 2007.

International Search Report and Written Opinion issued in connection with International Patent Application No. PCT/US2019/052852, Nov. 28, 2019, 17 pages.

Office Action issued in connection with corresponding Canadian Patent Application No. 3,114,344, Jul. 22, 2021, 4 pages.

Office Action issued in connection with corresponding Japanese Patent Application No. 2021-518584, Sep. 21, 2021, 2 pages.

\* cited by examiner

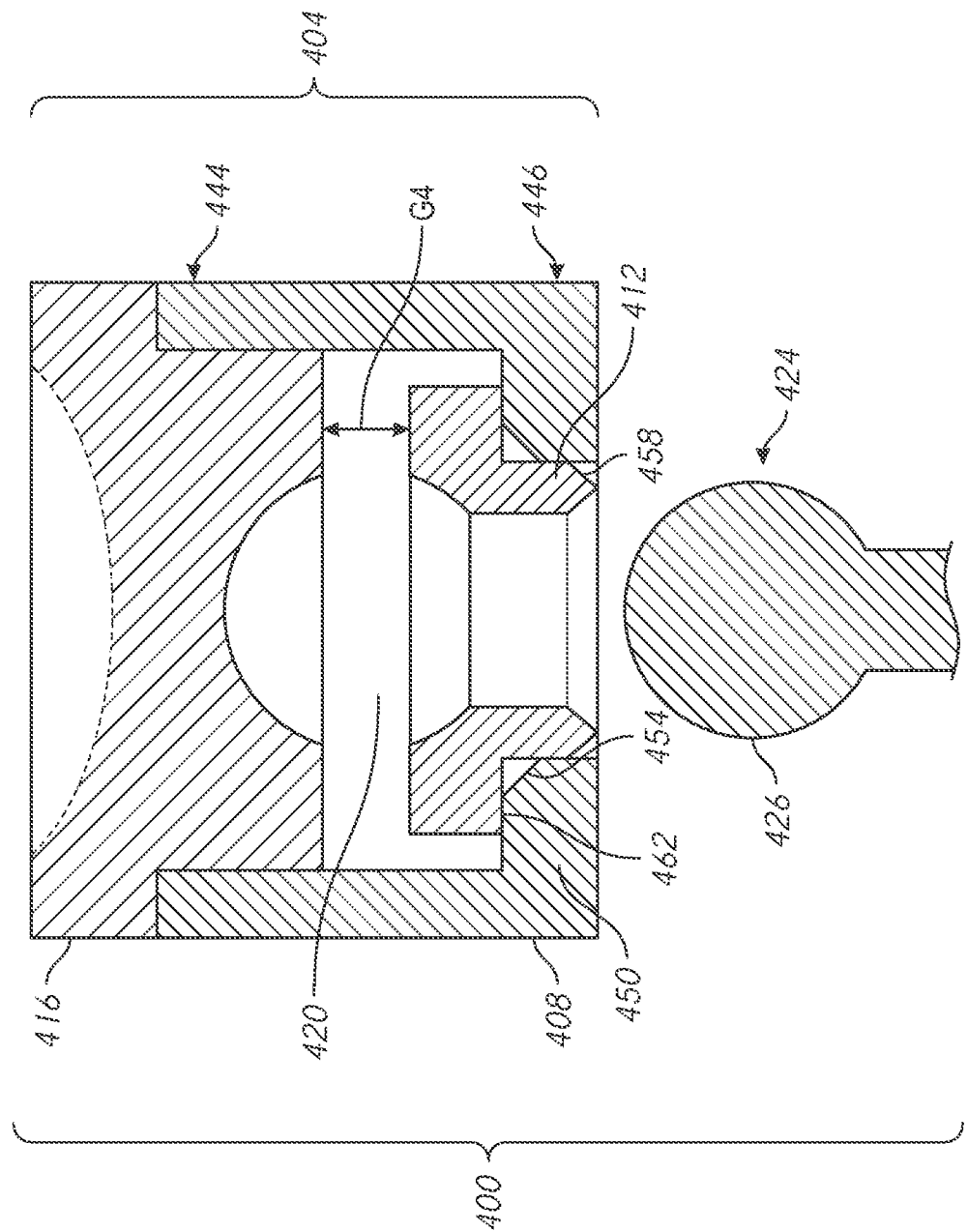

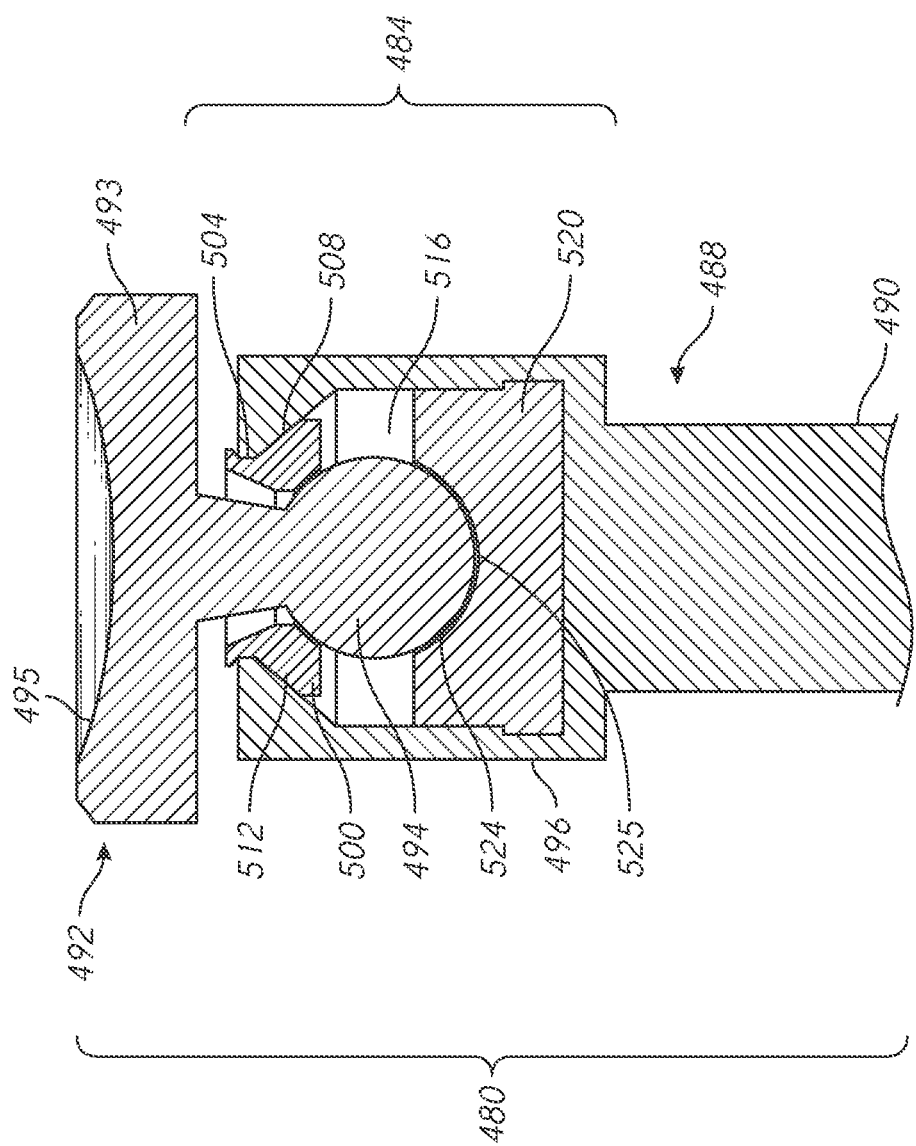

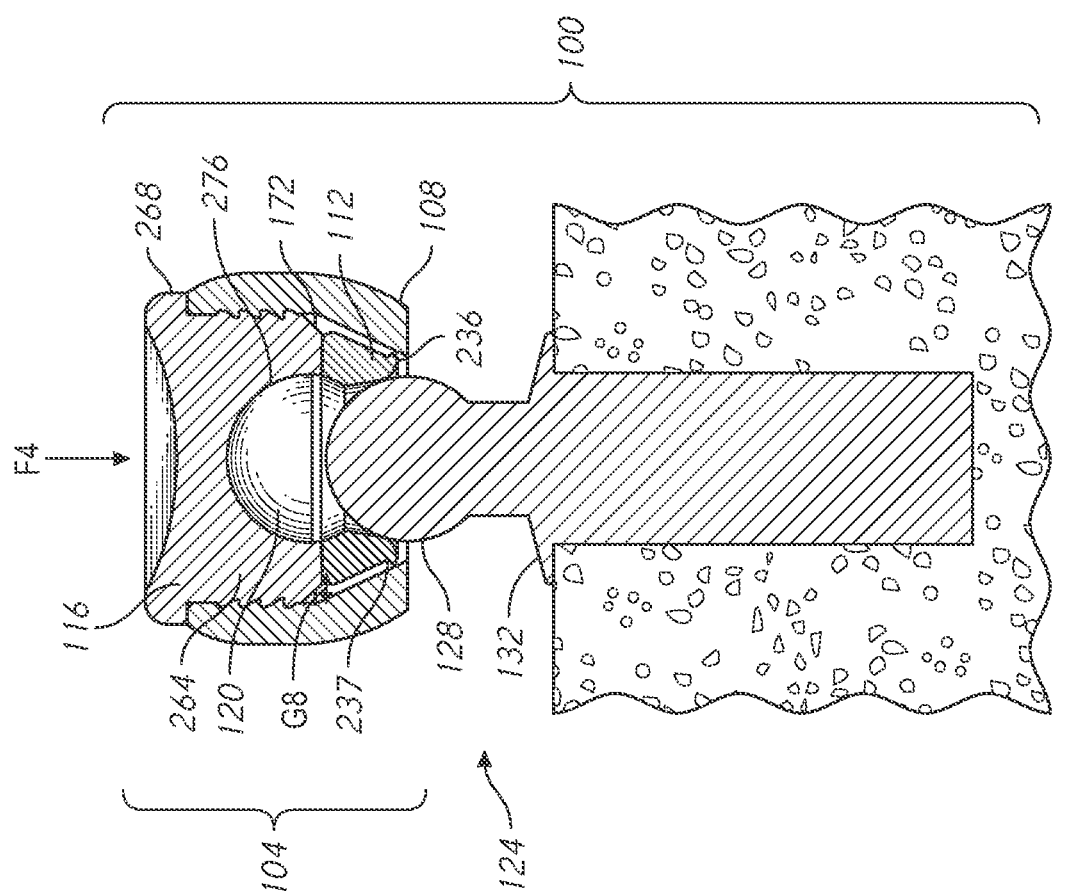

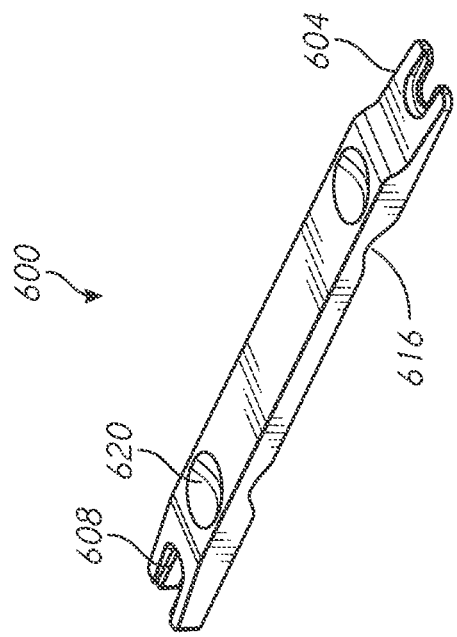
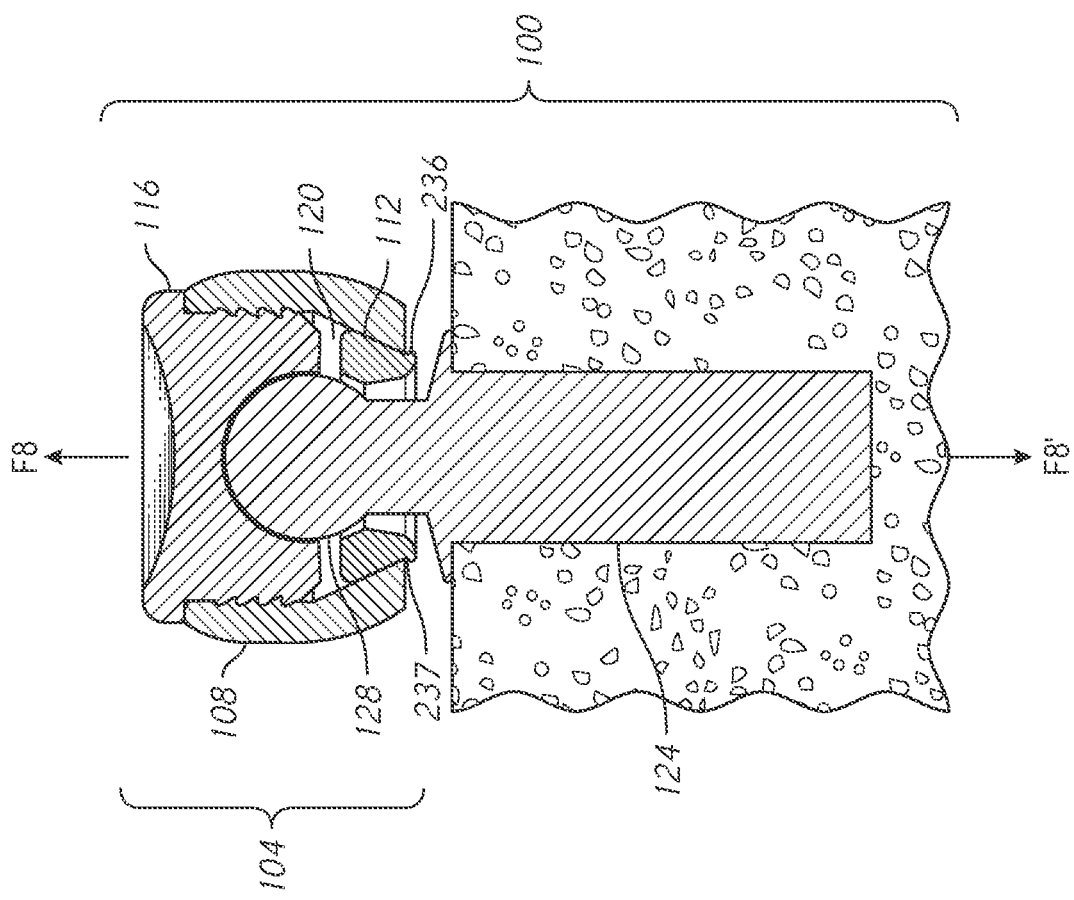

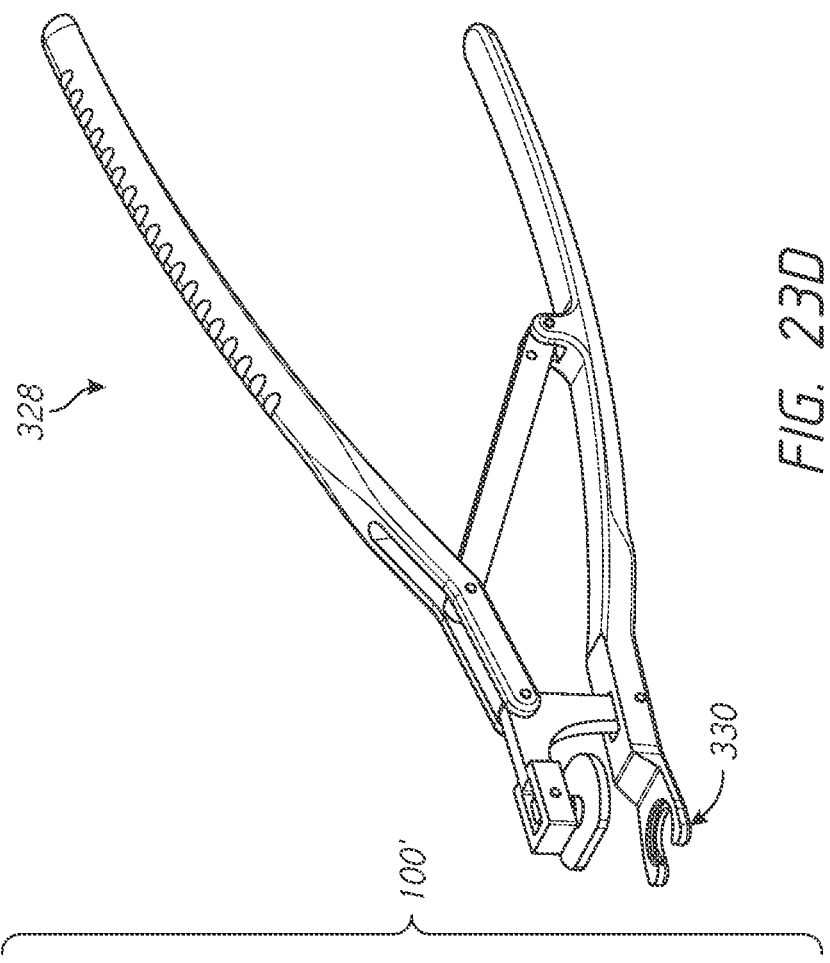
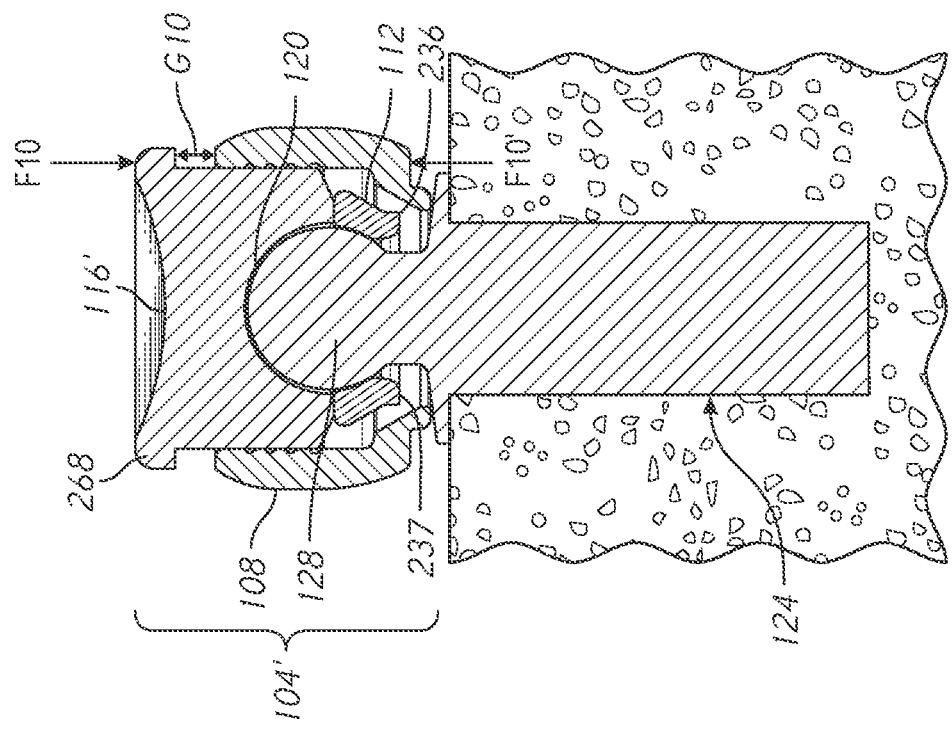
FIG. 23C
FIG. 23D

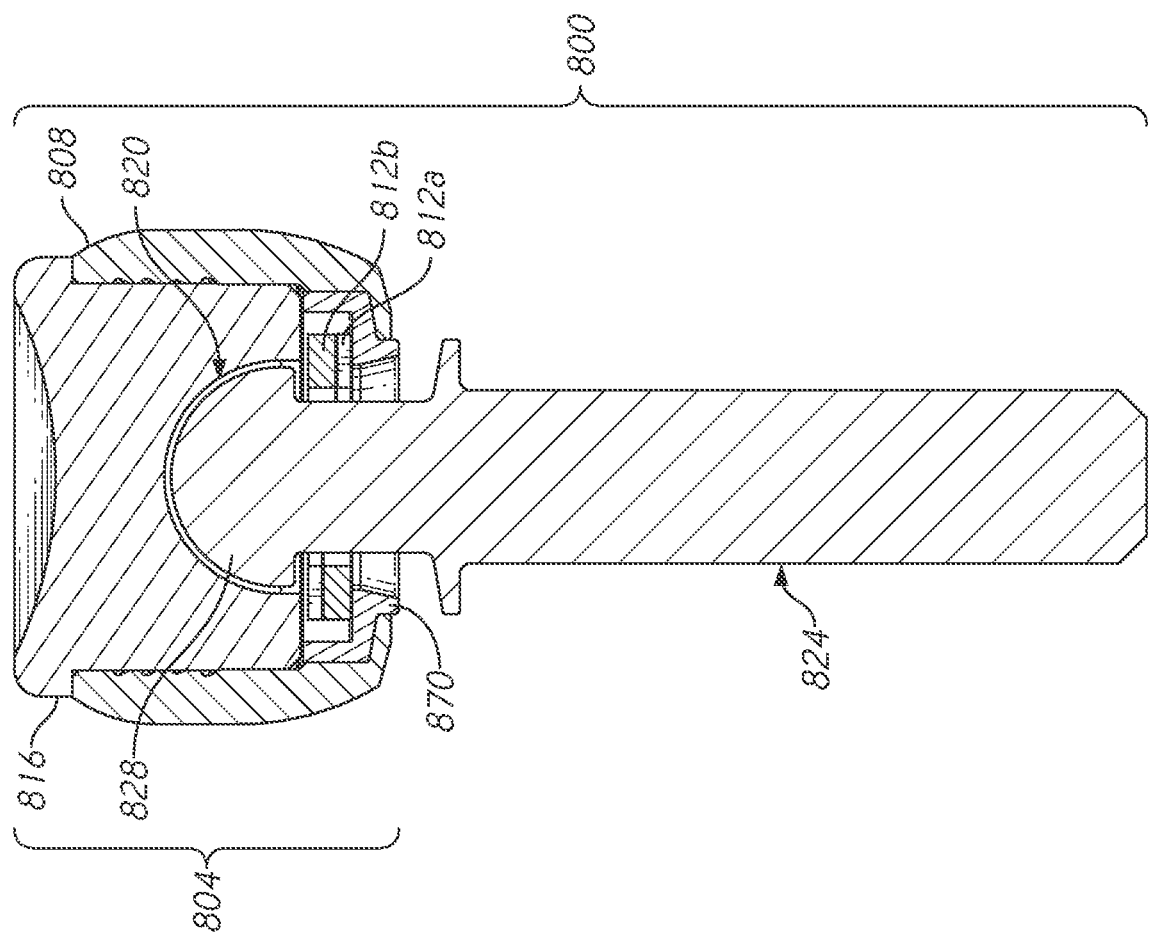

ELBOW JOINT PROSTHESES

INCORPORATION BY REFERENCE

This application is a continuation of co-pending U.S. patent application Ser. No. 17/583,886, filed on Jan. 25, 2022, which is a divisional application of U.S. patent application Ser. No. 17/279,846, filed on Mar. 25, 2021, now U.S. Pat. No. 11,266,507, issued on Mar. 8, 2022, which is a National Stage Application, filed under 35 U.S.C. 371, of International patent Application No. PCT/US2019/052852, filed on Sep. 25, 2019, which claims priority to U.S. Provisional Application No. 62/740,790, filed on Oct. 3, 2018, the entire contents of which are incorporated herein by reference.

BACKGROUND OF THE INVENTION

Field of the Invention

This application relates to an elbow joint prostheses and methods for assembling, fitting and implanting the same.

Description of the Related Art

Elbow prostheses are sometimes implanted in patients with deteriorating elbow joint function. The elbow joint function can deteriorate for a number of reasons, including osteoporosis, cartilage wear, trauma, and other reasons. The elbow is a complex joint involving three bones, with the joint being formed where the distal end of the humerus and the proximal ends of the radius and ulna meet. These bones are smaller than bones found at other joints more commonly replaced. As a result, the individual components are also smaller.

Because the lower arm is highly mobile, artificial elbow joint components must be highly mobile and able to sustain a wide variety of loads without failing.

SUMMARY OF THE INVENTION

In view of the foregoing, improved elbow joint prostheses and components therefore are desired. For example, an improved radial head assembly is desired that can sustain high loads and/or loads over a wider range of directions.

In one embodiment, a radial head assembly is provided that includes a stem, a collar, a locking ring, and an articular member. The stem has a convex articular head on one end thereof. The collar has a collar wall that defines a first collar opening, a second collar opening, and a passage therethrough. The collar wall has an interior collar surface that has an angular portion proximate to the first collar opening. The locking ring has a ring wall. The ring wall has a ring opening. The ring wall has an angular outer surface and a slot configured to permit the ring wall to radially expand. The angular outer surface engages the angular portion of the interior collar surface. The articular member has a base and a projection. The base has an outer rim and a first concave surface. The projection extends from the base and has a second concave surface disposed between the first concave surface and an end of the articular member opposite the first concave surface. The projection has a peripheral surface configured to engage the interior collar surface. The articular member and the locking ring define an articular space within the collar. The articular space is configured to receive the convex articular head.

In another embodiment, an articular assembly is provided that includes an articular portion configured to couple with a stem coupled with a first bone. The articular portion has a concave surface, a collar, and a trapping member. The concave surface is disposed on the articular portion to face a second bone opposite the first bone. The collar has a collar wall that a collar opening opposite the concave surface and an interior trapping surface proximate to the collar opening. A space extends from the collar opening into the interior of the collar. The trapping member has an opening and a mating surface configured to engage the interior trapping surface. The articular assembly has a configuration in which the interior trapping surface engages the mating surface to prevent the trapping member from expanding such that a head of a stem disposed in the articular space can be retained in the articular space.

In another embodiment, a surgical method is provided. In the method, a distal portion of a stem is attached to a first bone. The stem has an articular head on a proximal end of the stem. An opening of an articular assembly is placed on the articular head. The articular assembly has a concave surface and a trapping member. The concave surface is disposed on the articular assembly opposite the opening to face a second bone opposite the first bone. A collar defines the opening. A space extends from the opening into the interior of the articular assembly. An interior trapping surface is disposed proximate to the opening of the articular assembly. The trapping member is disposed in the opening. The trapping member is expanded. The articular head is advanced through the trapping member such that the articular head is disposed between the trapping member and the concave surface. The trapping member is disposed between the articular head and the interior trapping surface.

In another embodiment, a kit is provided that includes a radial head assembly and a removal tool. The radial head assembly includes a collar and a locking ring. The collar has an opening that provides access into an internal space of the collar. An exterior wall extends from the opening. An interior wall extends from the opening. The collar wall has an aperture that extends from the exterior wall toward the interior wall. The locking ring has a flange and an angled surface. The locking ring is positionable in the internal space in a first position in which the flange is spaced away from the opening and in a second position in which the flange spans the opening to cause the locking ring to be securely retained in the opening. The removal tool has a distal end with a projection configured to be inserted through the aperture to compress the locking ring to enable the ring to move from the second position to the first position.

In another embodiment, an articular assembly is provided that includes a first articular member and an articular portion that is configured to couple with a stem coupled with a first bone. The first articular member comprises a concave surface. The concave surface is disposed on the first articular member to face a second bone opposite the first bone. The articular portion has a collar and a trapping member. The collar has a collar wall that defines a collar opening adjacent to the concave surface and an interior trapping surface proximate to the collar opening. A space extends from the collar opening into an interior of the collar. The trapping member has a trapping member opening and a mating surface configured to engage the interior trapping surface. The articular assembly has a configuration in which the interior trapping surface engages the mating surface to prevent the trapping member from expanding such that a head member coupled with the concave surface and disposed in the articular space can be retained in the articular space.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No individual aspects of this disclosure are essential or indispensable.

BRIEF DESCRIPTION OF THE DRAWINGS

These and other features, aspects and advantages are described below with reference to the drawings, which are intended for illustrative purposes and should in no way be interpreted as limiting the scope of the embodiments. Furthermore, various features of different disclosed embodiments can be combined to form additional embodiments, which are part of this disclosure. In the drawings, like reference characters denote corresponding features consistently throughout similar embodiments. The following is a brief description of each of the drawings.

FIG. 17 shows another embodiment of a radial head assembly as disclosed herein;

FIG. 18 illustrated a further embodiment of a radial head assembly as disclosed herein;

FIG. 20A is a schematic view illustrating a portion of a method of implanting a radial head assembly in a radius of a patient adjacent to an elbow joint;

FIG. 20B illustrates a portion of a method of implanting a radial head assembly subsequent to the portion illustrated in FIG. 20A;

FIG. 20C is a perspective view of one embodiment of an assembly tool that can be used to secure an articular assembly to a stem;

FIG. 23C illustrates a portion of a method of implanting a radial head assembly subsequent to the portion illustrated in FIG. 23B;

FIG. 23D is a perspective view of one embodiment of a locking tool that can be used to secure an articular assembly to a stem;

FIG. 27 illustrates a cross-section view of another embodiment of a radial head assembly as disclosed herein;

DETAILED DESCRIPTION

This application is directed to an elbow joint prostheses and methods that can be used in elbow joint replacement procedures, which can be used to correct elbow joint conditions including deformity, wear, osteoarthritis, and trauma. As discussed in greater detail below the apparatuses and methods herein reduce risk of dislocation and decoupling, and also facilitate implantation and removal of the apparatuses during surgical procedures, and provide ranges of sizes to better fit a full range of patients.

I. Elbow Joint Components and Force Dynamics

Figure 1:
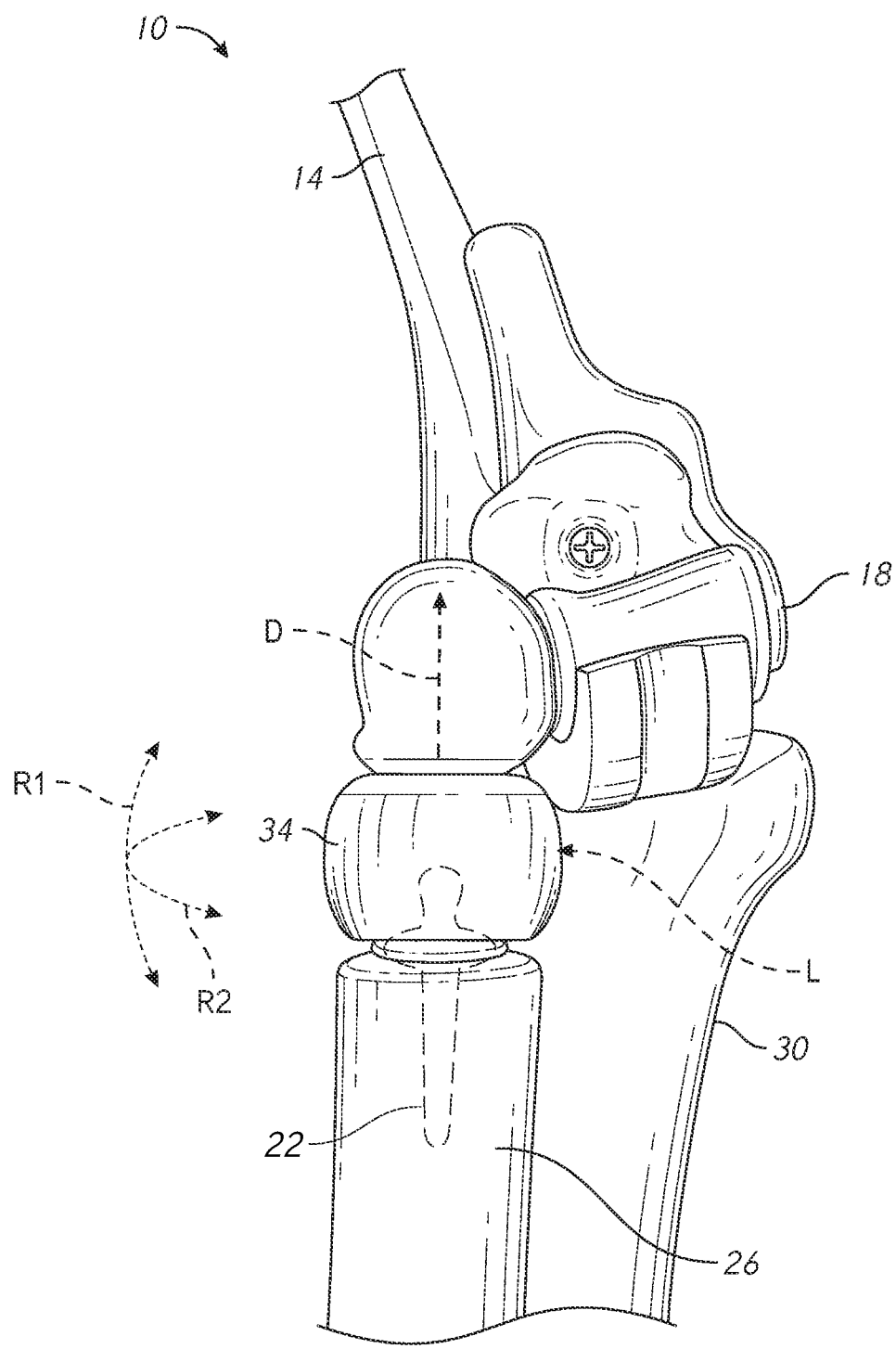
FIG. 1 is a schematic view of an elbow joint prosthesis.

FIG. 1 shows an elbow joint prosthesis 10. The prosthesis 10 has a humeral stem 14, a humeral spool 18, and a radial stem 22. The radial stem 22 is shown embedded in a radius 26. The prosthesis 10 also can have an ulnar stem (not shown) embedded in the ulna 30. A radial head 34 is disposed on the radial stem 22 and is coupled with one end of the humeral spool 18. The radial head 34 can be capable of bipolar articulation. For example, the radial head 34 can rotate around a center of the spherical end of the humeral spool 18, if the humeral stem 14 is held stationary as the radius and ulna are rotated up toward the humerus. This motion corresponds to the direction provided by double arrow R1. Also, where no or minimal rotation in the direction of the arrows R1 occurs, there can still be rotation of the lower arm, e.g., of the radius about a central axis of the lower arm. Such motion can correspond to the motion indicated by the double arrows R2. Moreover, it may be possible in some cases to pivot the radial head 34 relative to the radial stem 22. This rotation can be in the same directions as indicated by arrows R1 and R2 but without motion at the interface between the radial head 34 and the spherical portion of the humeral spool 18.

The radial head 34 is also subject to loading and must remain intact upon such loading. Two loads that can occur are a distraction load indicated by an arrow D and a side load indicated by the arrow L. The distraction load D can be applied at the joint in directions away from the joint toward the shoulder and/or toward the hand. The distraction load D could separate the radial head 34 from the stem 22. The side load L can occur in high ranges of twisting of the lower arm. Such twisting can result when the upper arm is held stationary and the hand is rotated, such as in the motion used to turn a knob. If the radial head 34 contacts a hard surface, such as a portion of the stem 22 or the radius 26, during such movement the radial head 34 could be pried off the stem 22. These concerns prompt the need for radial head designs with improved security. While improved security is beneficial, certain embodiments provide for ease of removal as well.

II. Elbow Joint Assemblies with Enhanced Security

Figure 15:
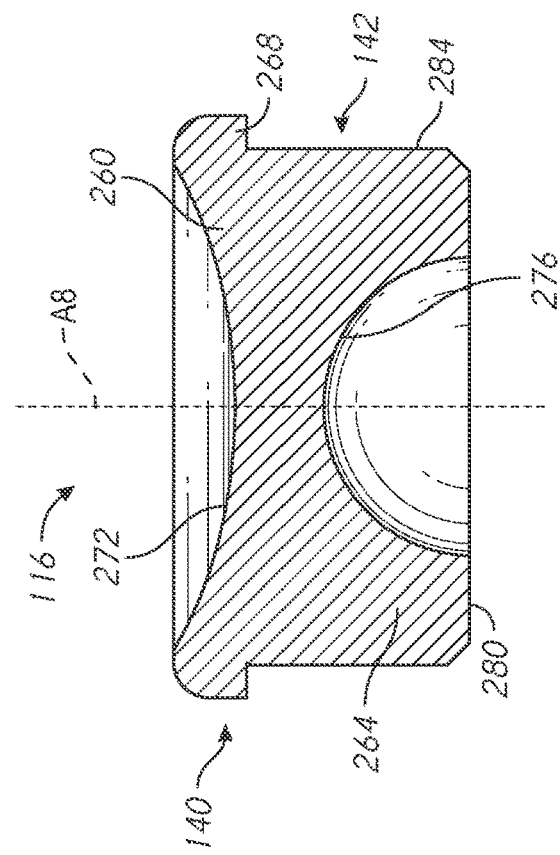
FIG. 15 is a cross-sectional view of the articular member of FIG. 12 taken at the section plane 15-15.
Figure 16A:
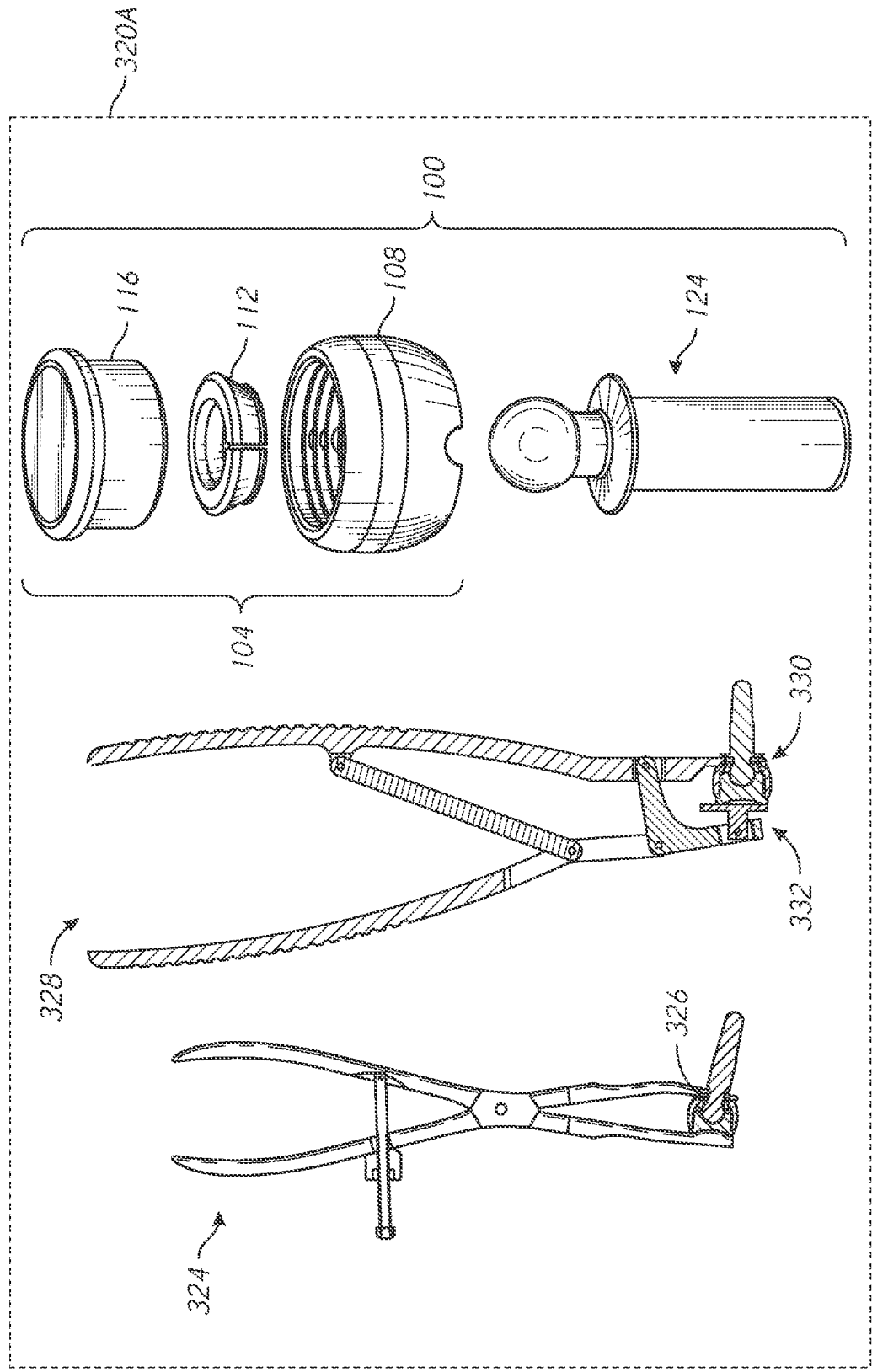
FIG. 16A illustrates a radial head assembly kit according to one embodiment herein.
Figure 16B:
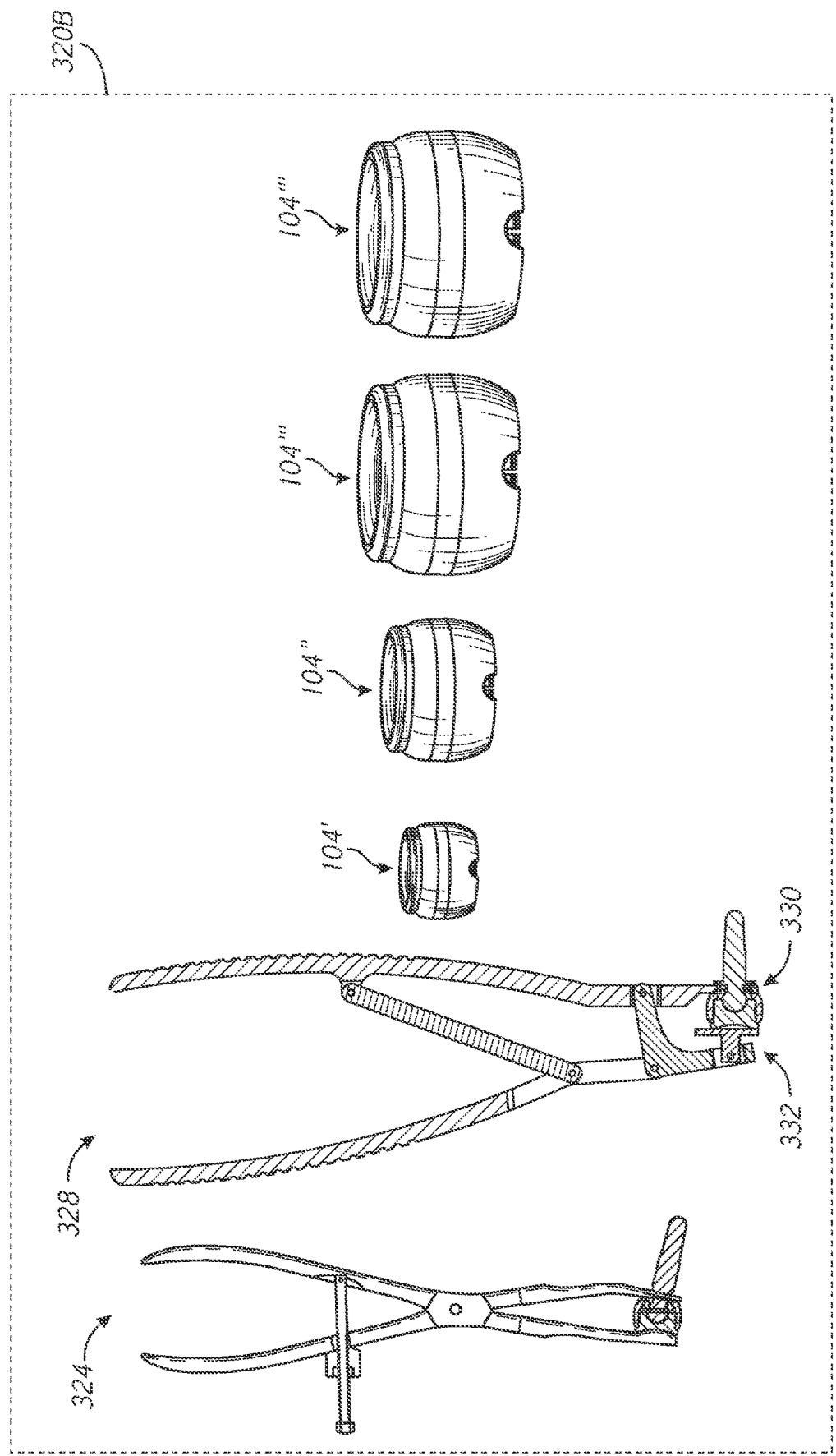
FIG. 16B illustrates another embodiment of a radial head assembly kit as disclosed herein.
Figure 21A:
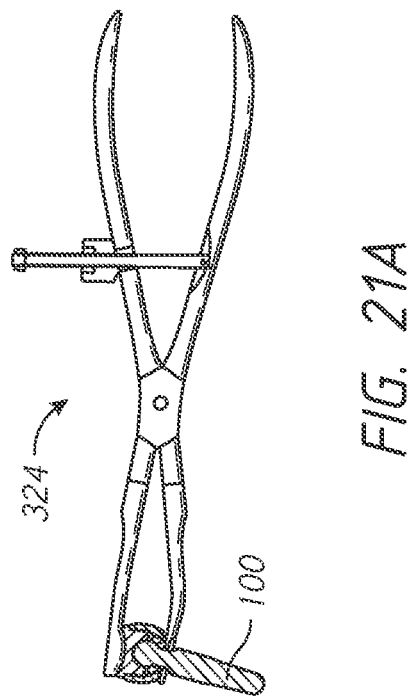
FIG. 21A shows an embodiment of a removal tool that can be used to remove an articular assembly from a stem.
Figure 21:
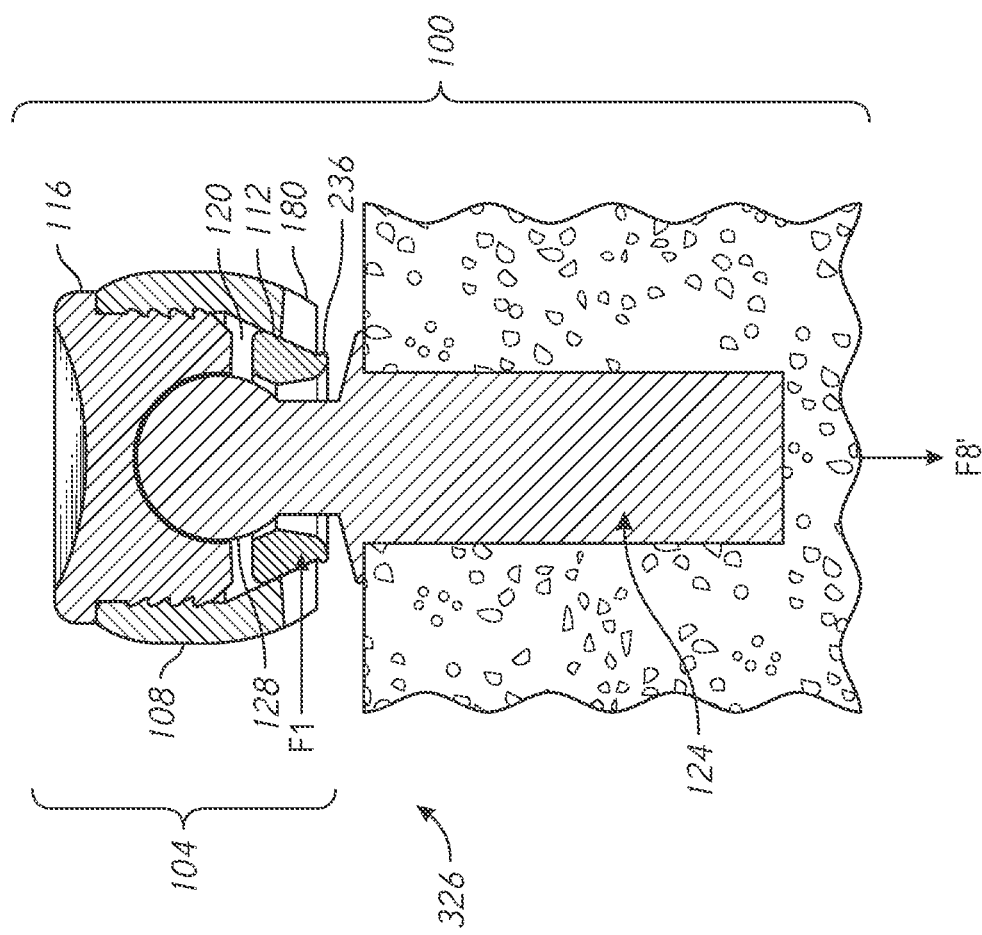
FIG. 21 illustrates a portion of a method of removing a radial head assembly in a radius of a patient adjacent to an elbow joint.
Figure 22:
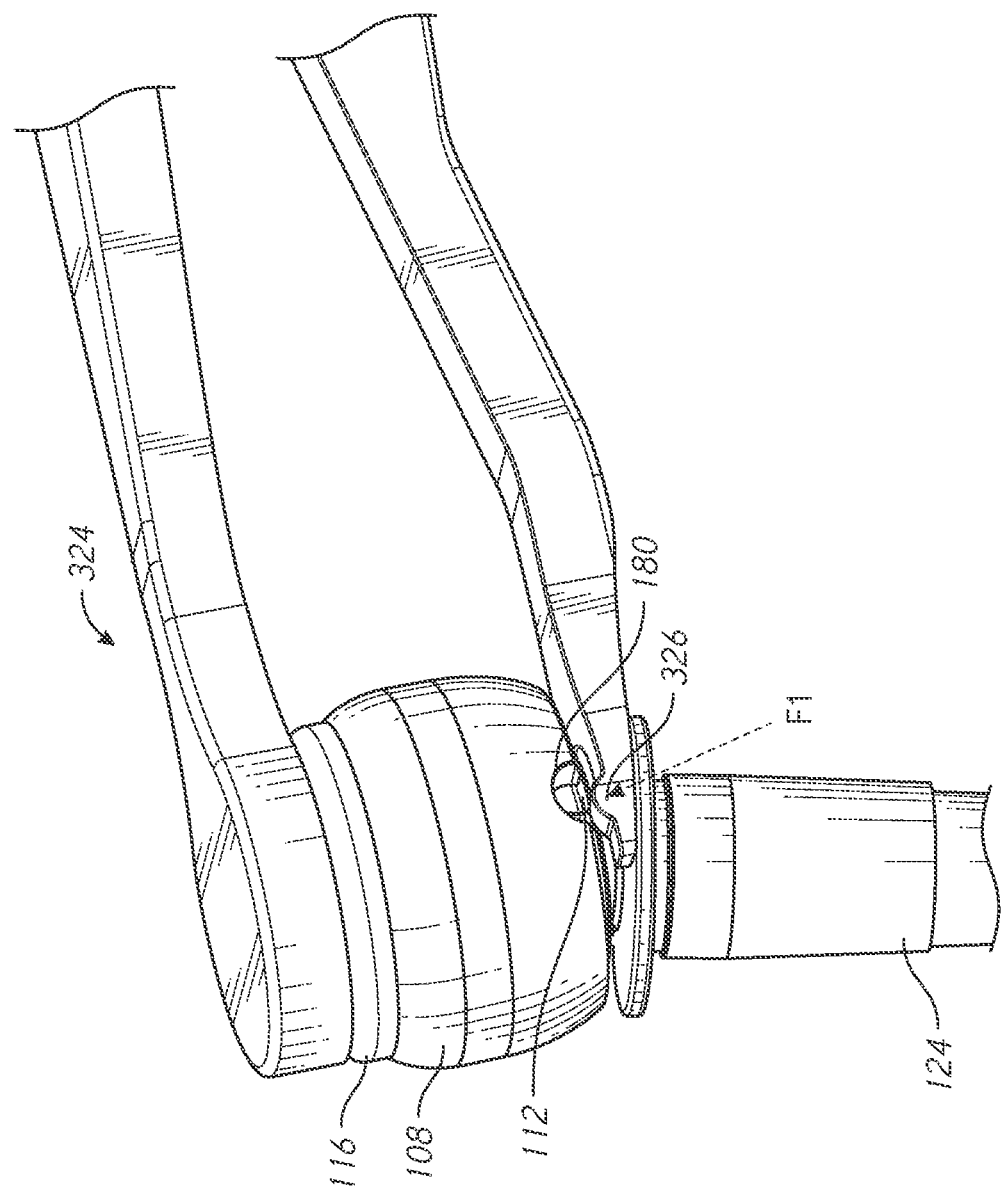
FIG. 22 shows one method of using the removal tool of FIG. 21A.

A variety of elbow joint prosthesis assemblies and components are provided herein that provide enhanced performance, such as enhanced security of assembly over a wide range of anatomic loading and convenience in implantation and removal. Sections II(A) along with FIGS. 2-15, II(C) along with FIG. 17, II(D) along with FIGS. 18 and 19, II(E) along with FIGS. 37-32, II(F) along with FIGS. 37 and 38, II(G) along with FIGS. 39 and 40, and II(H) along with FIG. 41 illustrate various embodiments of radial head assemblies in which anatomic loading security and ease of implantation and removal are provided. Section II(B) along with FIGS. 16A-16B illustrate various useful kits that can be provided to facilitate procedures. Section III(A) along with FIGS. 20A, 20B, and 23A-23E illustrate methods of assembling radial head assemblies on patients. Section III(B) along with FIGS. 21, 21A, and 22 illustrate methods of removing radial head assemblies on patients.

A. Radial Head Assemblies with Enhanced Load Security

Figure 2:
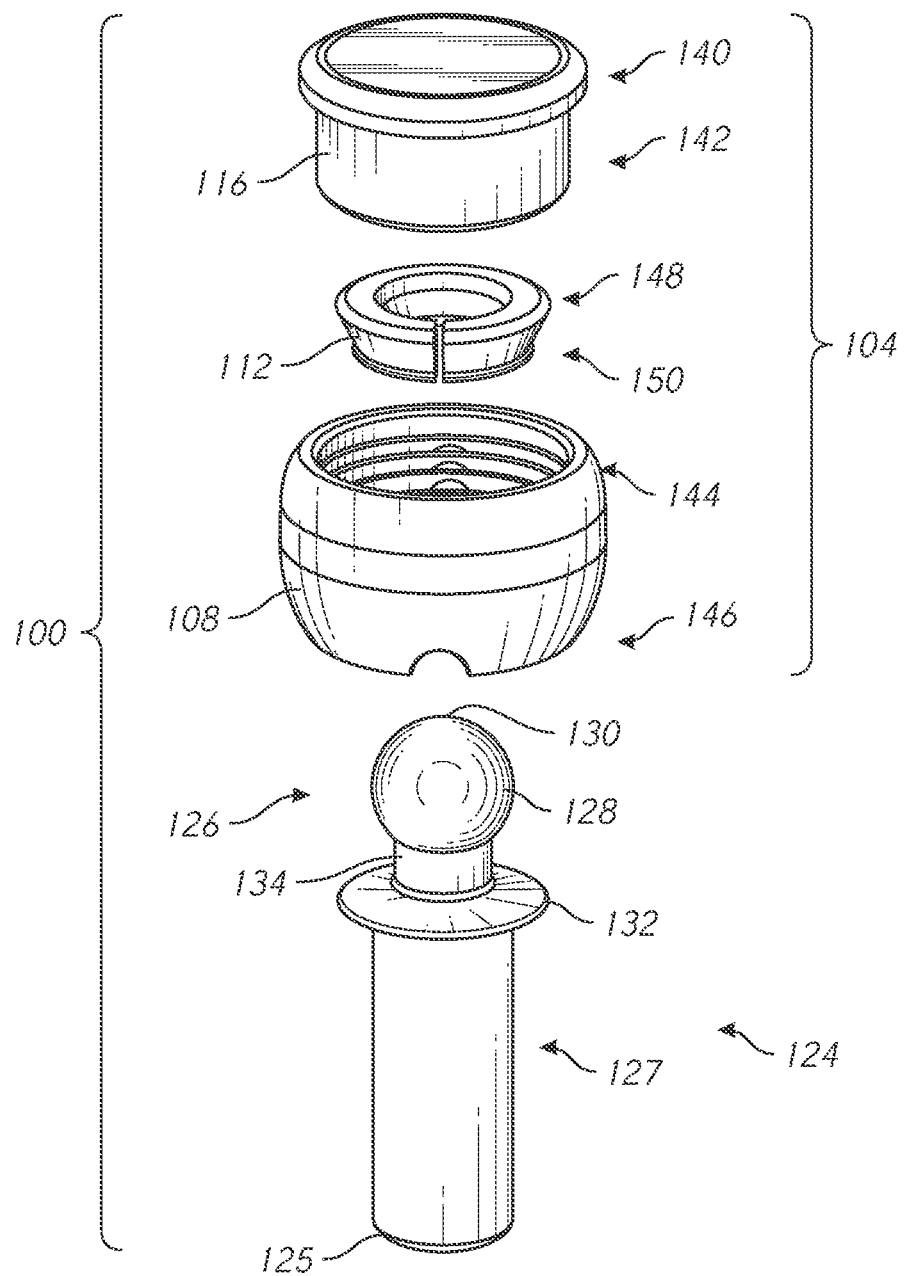
FIG. 2 is an exploded view of a radial head assembly.

FIG. 2 shows an exploded view of one embodiment of a radial head assembly 100. The radial head assembly 100 can form a portion of an elbow joint prosthesis of FIG. 1. The radial head assembly 100 includes an articular assembly 104 and a stem 124. The articular assembly 104 includes a collar 108, a locking ring 112, and an articular member 116.

The stem 124 includes a distal end 125, a proximal portion 126. A distal portion 127 of the stem 124 extends from the distal end 125 toward the proximal portion 126. The distal portion 127 is configured to be embedded in bone, e.g., in the radius bone adjacent to an elbow joint, as discussed above. The distal portion 127 can have a textured surface, a rough surface or other structure or treatment adapted to provide for ingrowth of bone to integrate the stem into a radius bone. The textured surface provides for mechanical grip in bone cement where bone cement is used to secure the stem 124 in the bone. The textured surface also provides for bone ingrowth where the stem 124 is implanted as a press fit system or technique. The proximal portion 126 can include a convex articular head 128. The articular head 128 can be disposed on or extend from a proximal end 130 of the stem 124.

The stem 124 also can include an annular member 132. The annular member 132 can be disposed adjacent to the convex articular head 128. The annular member 132 can have a distal face that extends from adjacent to a proximal end of the distal portion 127 to an outer periphery. The outer periphery of the annular member 132 can be spaced a distance radially or transversely away from the proximal end of the distal portion 127. The distance between the proximal end of the distal portion 127 and the outer periphery of the annular member 132 can correspond to a width of the annular member 132. The width of the annular member 132 can be constant. The annular member 132 can be configured to interface with a proximal end face of a radius bone. In some methods, the annular member 132 provides a positive stop upon insertion of the stem 124 into the radius bone. In some embodiments, a proximal face of the annular member 132 opposite the distal face provides a portion of the radial head assembly 100 that lies between the articular assembly 104 and the proximal face of the radial bone. The annular member 132 can provide protection against impingement on the radius bone by the articular assembly 104.

In one embodiment, the proximal portion 126 includes the convex articular head 128 and an axial portion 134 that extends along a distance between the head 128 and the annular member 132. The axial portion 134 elevates the articular assembly 104 above the proximal face of the annular member 132. The axial portion 134 elevates the articular assembly 104 above the radius bone when the assembly 100 is implanted. Such elevation provides clearance between the articular assembly 104 and the proximal face of the radius bone into which the stem 124 is inserted, as discussed further below.

Figure 4:
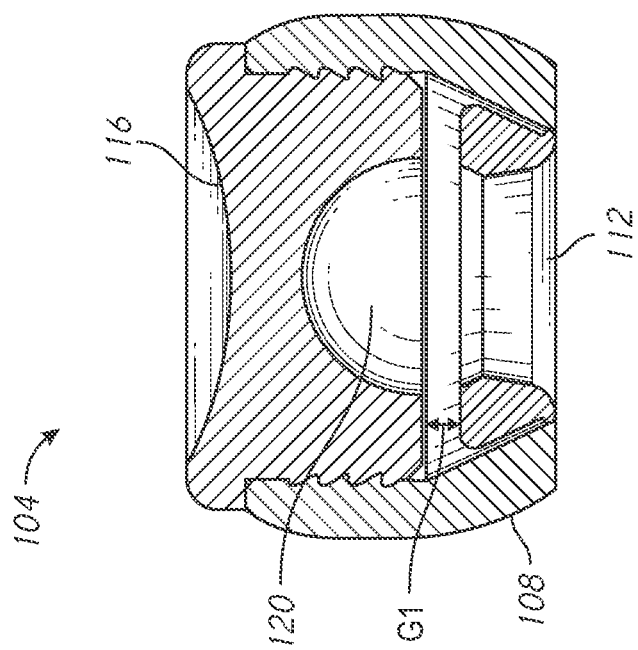
FIG. 4 is a cross-section view of the articular assembly of FIG. 3 taken at section plane 4-4.
Figure 3:
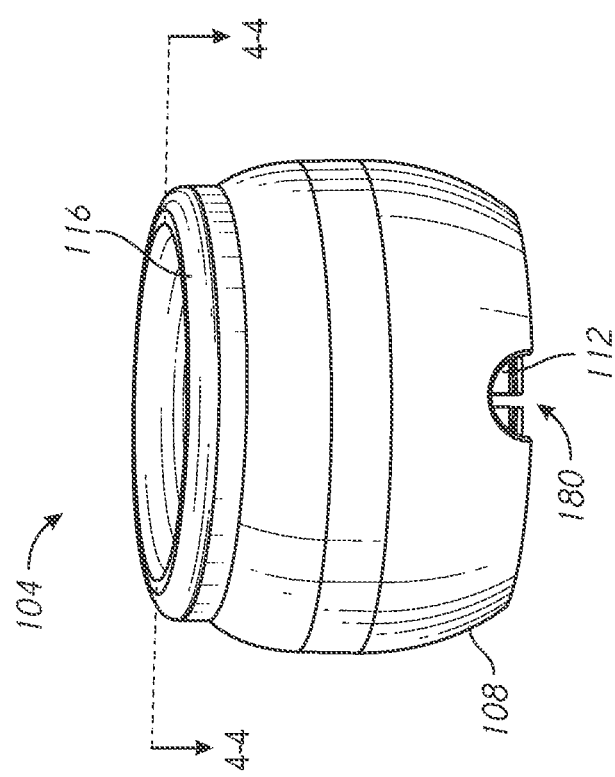
FIG. 3 is a perspective view of one embodiment of an articular assembly shown in FIG. 2.
Figure 4B:
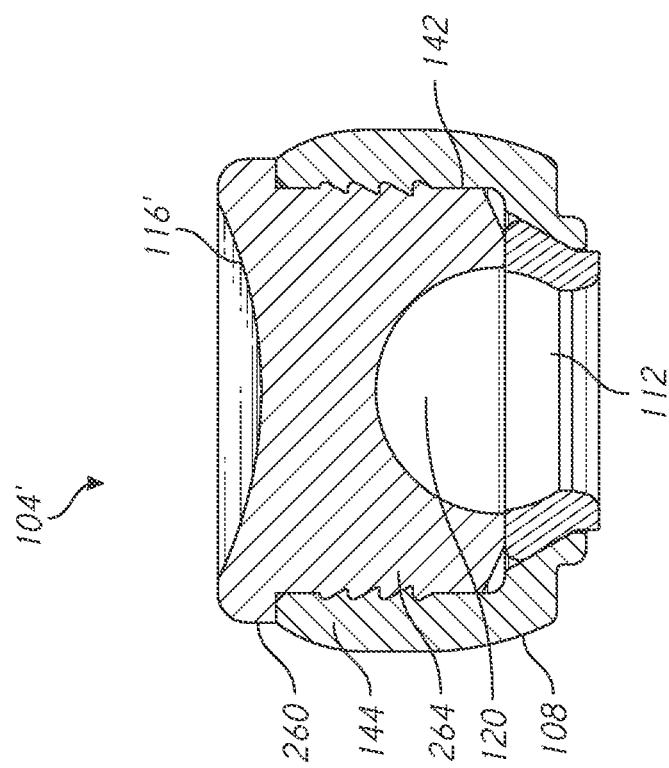
FIG. 4B is a cross-section view of the articular assembly of FIG. 4A in a locked configuration.
Figure 4A:
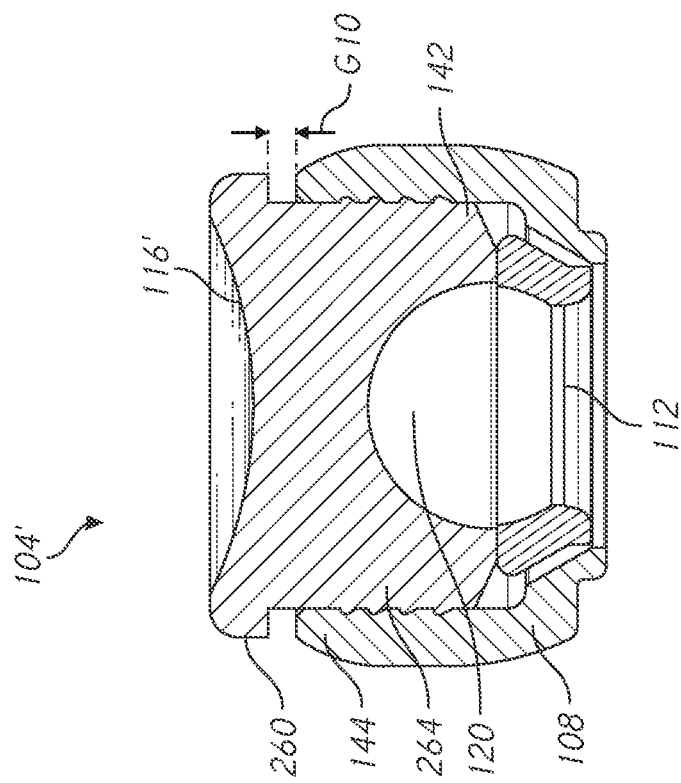
FIG. 4A is a cross-section view of an embodiment of an articular assembly in an unlocked configuration.
Figure 6:
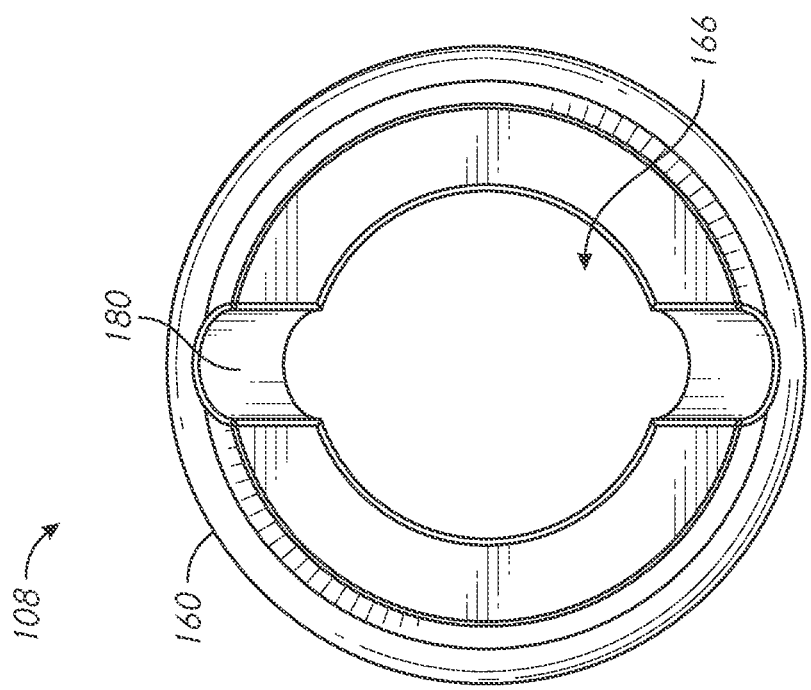
FIG. 6 is a bottom view of the collar shown in FIG. 5.
Figure 7:
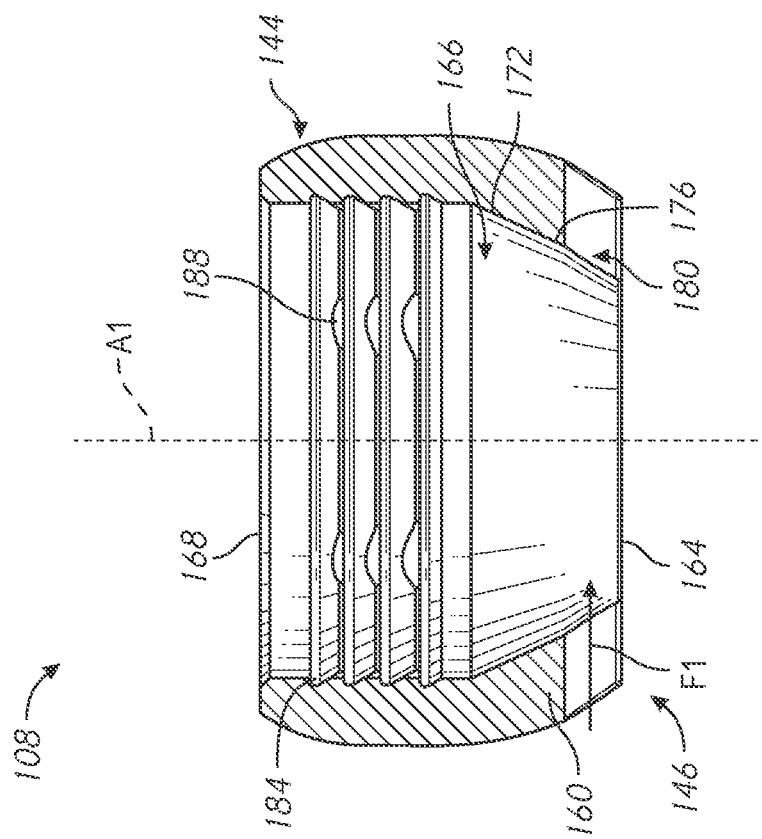
FIG. 7 is a cross-sectional view of the collar shown in FIG. 5 taken at the section plane 7-7.
Figure 8:
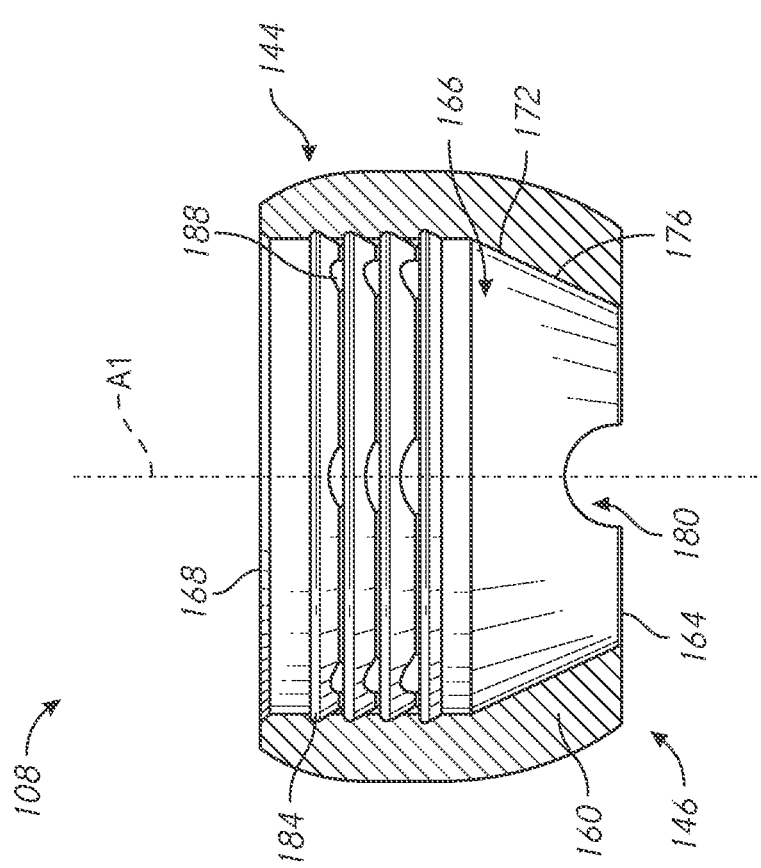
FIG. 8 is a cross-sectional view of the collar shown in FIG. 5 taken at the section plane 8-8.
Figure 14:
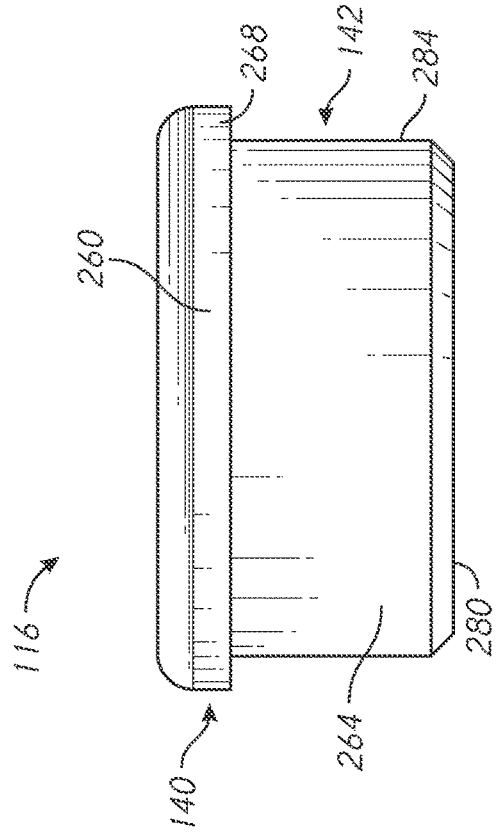
FIG. 14 is a side view of the articular member FIG. 12.

FIGS. 3 and 4 show that in one configuration the locking ring 112, which is an example of a trapping member disclosed herein, is disposed within the collar 108 and the articular member 116 is partially disposed within the collar 108. The articular member 116 can include a proximal portion 140 and a distal portion 142 (as shown in FIGS. 2, 14, and 15). The proximal portion 140 can include a proximal surface of the articular assembly 104. The proximal portion 140 can be exposed outside of a proximal portion 144 of the collar 108 (as shown in FIGS. 2, 7, and 8). The distal portion 142 of the articular member 116 can be configured to be advanced into the collar 108. The distal portion 142 is disposed distally of the proximal portion 144 of the collar 108 in FIG. 4. The distal portion 142 can be disposed inside the collar 108. The axial length of the collar 108, e.g., along the direction from the proximal end to the distal end thereof, can be greater than the axial length of the distal portion 142 of the articular member 116 such that a distal end, or face, of the articular member 116 is proximal of a distal end of the collar 108. FIG. 4 shows that the distal end of the distal portion 142 of the articular member 116 can be advanced more than half way into the collar 108. FIG. 4 shows that the distal end of the distal portion 142 can be disposed well short of the distal end of the collar 108, which provides a range of motion of the locking ring 112, as discussed further below. In some embodiments, as illustrated in FIGS. 4A and 4B, respectively, the distal portion 142 of an articular member 116' can be disposed against the locking ring 112 when the articular assembly 104' is in the unlocked configuration and/or locked configuration.

FIG. 4 illustrates that the articular member 116 mates with the collar 108. In one embodiment, the proximal portion 140 comprises a base 260 of the articular member 116 (as shown in FIGS. 14 and 15). The proximal portion 140 can have a dimension that is greater at least in part than an opening at the proximal portion 144 of the collar 108. This configuration allows the articular member 116 to be inserted until an outer rim 268 (as shown in FIGS. 14 and 15) of the proximal portion 140 is disposed over a proximal portion, e.g., a proximal wall, of the collar 108. The outer rim 268 can abut the proximal portion 144 of the collar 108. The abutment of the proximal portion 140 with the proximal portion 144 provides a positive stop for the articular member 116 as it the articular member 116 is inserted into the collar 108. The distal portion 142 can comprise a projection 264 of the articular member 116 (as shown in FIGS. 14 and 15). The projection 264 can project from the base 260 of the articular member 116. The distal portion 142 can be secured within the interior of the collar 108 with an interference fit, as discussed in greater detail below. For example, a peripheral surface or outer periphery of the articular member 116 can be larger than at least a portion of the interior surface, e.g., the inner periphery, of the collar 108 when the articular member 116 is separate from the collar 108. As such, at least some deformation of the distal portion 142 or compression of a portion of the inner periphery of the collar 108 can occur upon mating the articular member 116 with the collar 108. The compression or deformation creates sufficient friction to prevent the articular member 116 from inadvertently being separated from the collar 108, e.g., under operational loading in the elbow joint space.

In one embodiment, the articular member 116 is formed of a material, including a polymer such as polyethylene, PEEK, ceramics such as pyrocarbon, and the collar 108 is formed of a durable metal, such as cobalt chromium, titanium, or other similarly biocompatible durable material. Differences in the material properties of these materials may enable the articular member 116 to be deformed, e.g., compressed, upon insertion to create an interference fit.

Figure 11:
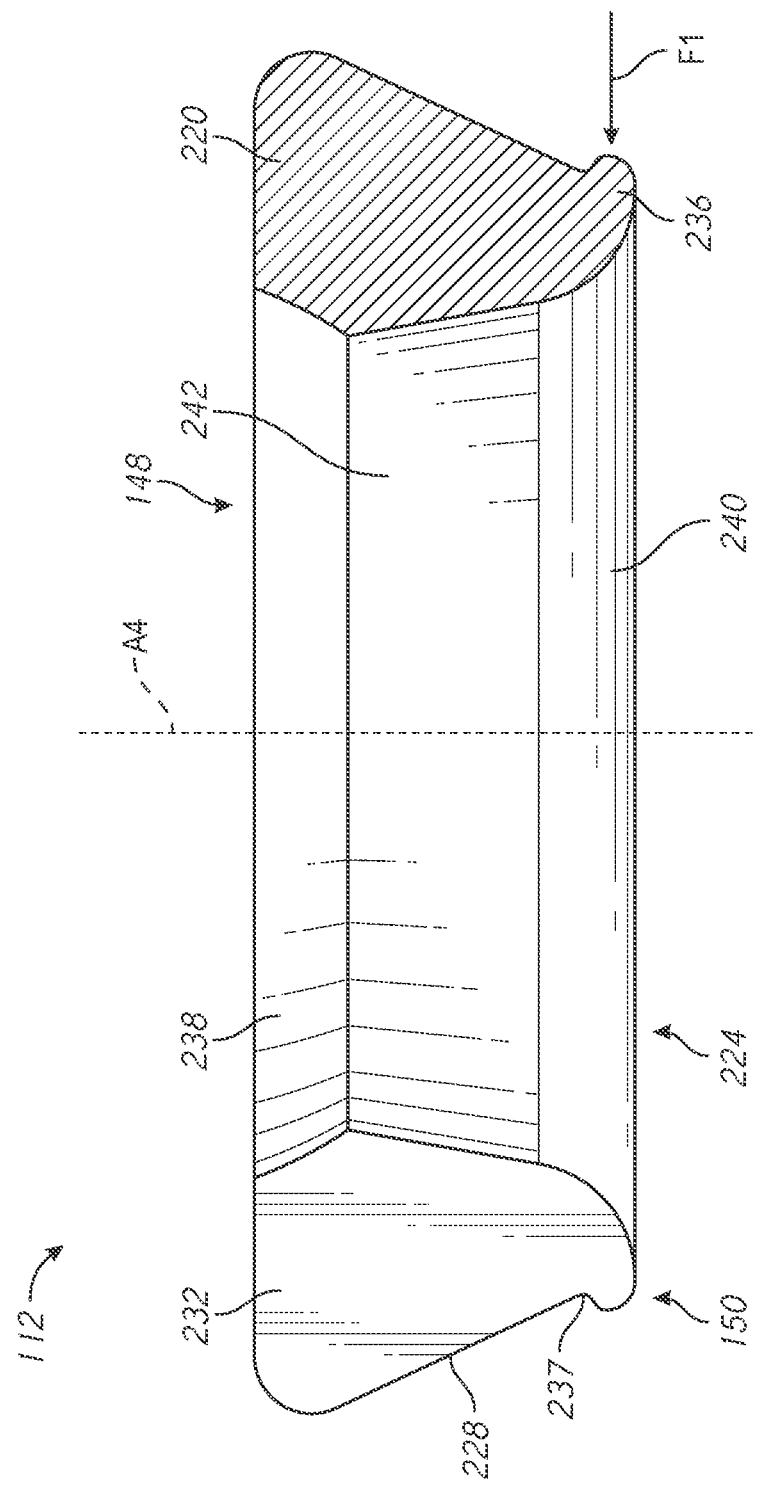
FIG. 11 is a cross-sectional view of the locking ring of FIG. 9 taken at the section plane 11-11.
Figure 13:
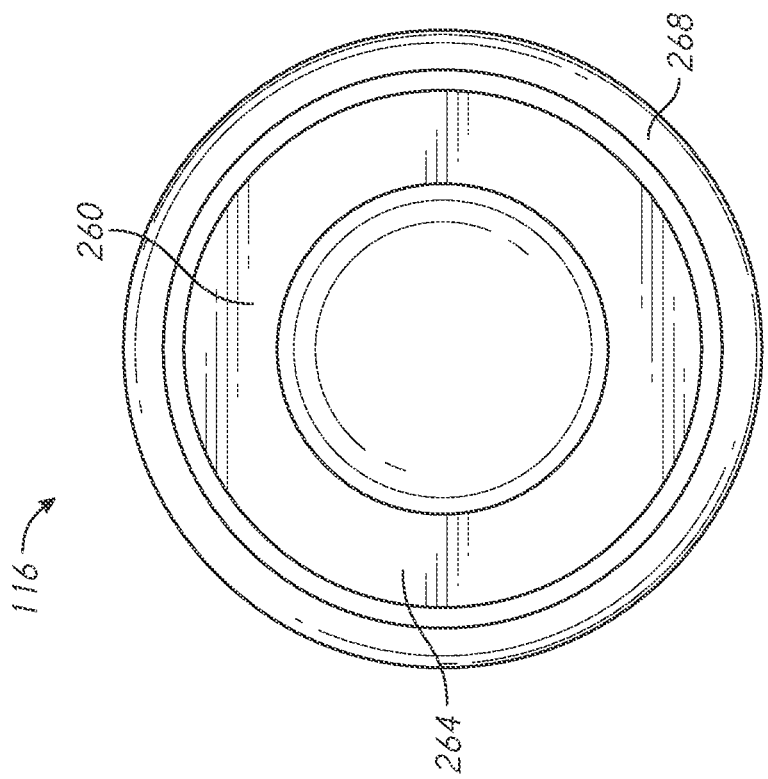
FIG. 13 is a bottom view of the articular member of FIG. 12.
Figure 12:
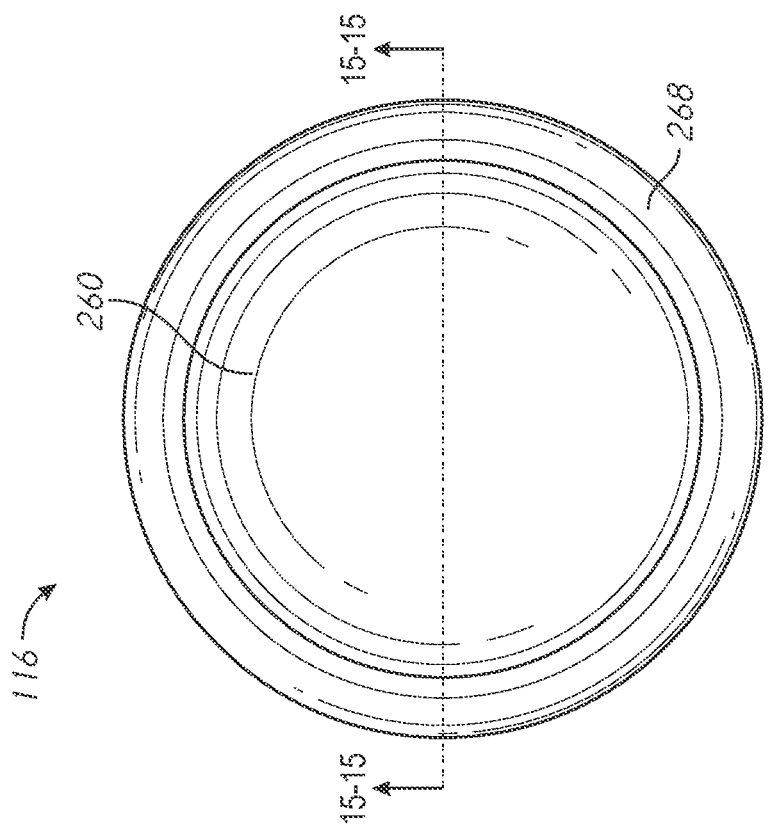
FIG. 12 is a top view of an articular member of the articular assembly of FIG. 3.

The locking ring 112 has a proximal portion 148 and a distal portion 150 illustrated in FIGS. 2 and 11. FIGS. 3 and 4 show a configuration of the articular assembly 104 where the locking ring 112 is disposed within the collar 108. For example, the proximal portion 148 and the distal portion 150 can be disposed between a proximal end and a distal end of the collar 108. FIG. 4 shows that in certain embodiments, the locking ring 112 can be disposed between a distal end of the articular member 116 and the distal end of the collar 108. FIG. 4 shows that when the distal end of the locking ring 112 is disposed at the same position as the distal end of the collar 108 there is a gap G1 between the proximal end of the locking ring 112 and the distal end of the articular member 116. The gap G1 corresponds to positions of the locking ring 112 along a range of motion of the locking ring 112 in an axial direction within the collar 108. In this context, the axial direction corresponds to the direction along the longitudinal axis of the stem 124 (see FIG. 20A). Motion of the locking ring 112 in the axial direction decreasing the magnitude of the gap G1 advantageously allows the locking ring 112 to move from a locked configuration in which the locking ring 112 is confined or constrained by the collar 108 to a free configuration in which the locking ring 112 is relatively less constrained or confined. Reducing the confinement or constraint imposed by the collar 108 on the locking ring 112 allows the ring 112 to expand. For example, movement of the locking ring 112 toward the articular member 116 reduces the magnitude of the gap G1. Movement of the locking ring 112 away the articular member 116 increases the magnitude of the gap G1. If the locking ring 112 is moved into contact with the articular member 116 the gap G1 is eliminated. This is one example of a free configuration of the locking ring 112. When in the free configuration, a gap G8 (see FIG. 20A) is disposed between an outer periphery of the locking ring 112 and the interior of the collar 108. The gap G8 and the flexibility of the locking ring 112 enables the locking ring 112 to expand. When the gap G1 is largest, the locking ring 112 is in a locked configuration and is engaged over an opening of the collar 108. The locked configuration prevents the stem 124 from being inadvertently dislodged from the articular assembly 104, as discussed further below.

FIGS. 4A and 4B show that, in certain embodiments, the projection 264 of the articular member 116' may have a length sufficient to abut against the locking ring 112 when the locking ring 112 is disposed entirely within the collar 108, e.g., when in the unlocked configuration. As such, no gap may exist between the proximal end of the locking ring 112 and the distal end of the articular member 116'. In some embodiments, the articular member 116' may have an unlocked position and a locked position within the collar 108 (as shown in FIGS. 4A and 4B, respectively). For example, FIG. 4A shows that, when the articular assembly 104' is in an unlocked configuration, the articular member 116' may be in proximal position in the collar 108 compared to the position of the articular member 116' in the collar 108 when in a locked position. A gap G10 may exist between a distal end face of a base 260 of the articular member 116' and a proximal end of the proximal portion 144 of the collar 108 when the articular member 116' is in the unlocked configuration. The length of the gap G10 can correspond to positions of the articular member 116' along a range of motion of the articular member 116' in an axial direction within the collar 108 relating to the unlocked and locked positions of the articular member 116'. In this context, the axial direction corresponds to the direction along the longitudinal axis of the stem 124 (see FIG. 23A-23E).

Moving the articular member 116' in an axial direction that decreases the magnitude of the gap G10 advantageously allows the articular member 116' to move from the unlocked configuration to the locked configuration. As the articular member 116' moves from the unlocked configuration to the locked configuration, a distal end face of the articular member 116' abuts against and, in turn, causes the locking ring 112 to also move from an unlocked configuration, in which the locking ring 112 is relatively less constrained or confined (as shown in FIG. 4A), to a locked configuration, in which the locking ring confined or constrained by the collar 108 (as shown in FIG. 4B). As discussed herein, increasing the confinement or constraint imposed by the collar 108 on the locking ring 112 causes the ring 112 to contract. Similar to other embodiments disclosed herein, when in the unlocked configuration, a gap G8 (see FIG. 23A) is disposed between an outer periphery of the locking ring 112 and the interior of the collar 108. The gap G8 and the flexibility of the locking ring 112 enables the locking ring 112 to expand. When the gap G10 is the smallest and/or eliminated as the articular member 116' due to axial movement in a distal direction, the locking ring 112 is in a locked configuration and is engaged over an opening of the collar 108. The locked configuration prevents the stem 124 from being inadvertently dislodged from the articular assembly 104', as discussed further below.

Figure 5:
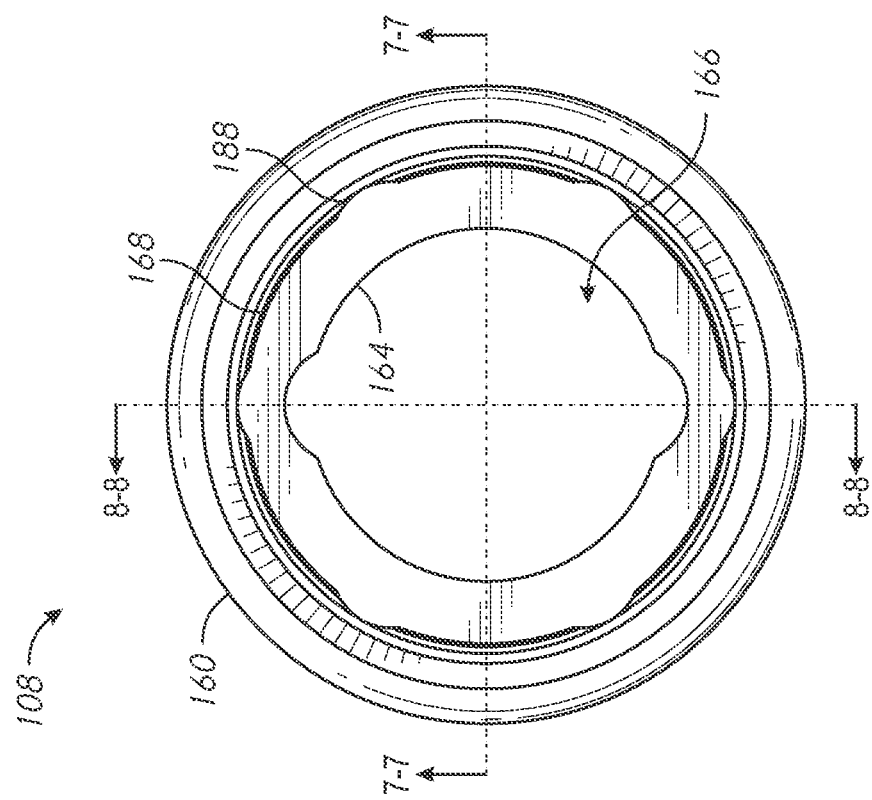
FIG. 5 is a top view of a collar of the articular assembly of FIG. 3.

FIGS. 5-8 show various views of the collar 108 of the articular assembly 104. The collar 108 has a collar wall 160 that extends between an outer periphery of the collar 108 and an inner periphery of the collar 108. The collar wall 160 defines a first collar opening 164, a second collar opening 168, and a passage 166 therethrough. The first collar opening 164 is disposed at the distal end of the collar 108. The second collar opening 168 is disposed at the proximal end of the collar 108. The collar wall 160 has an interior collar surface 172. The interior collar surface 172 can have an angular portion 176 proximate to the first collar opening 164. The angular portion 176 is configured such that a distal portion thereof is closer to a central longitudinal axis A1 of the collar 108 than is a proximal portion thereof. The distal portion of the angular portion 176 is disposed adjacent to the first collar opening 164. The angular portion 176 can have a symmetrical configuration about the axis A1. FIGS. 7 and 8 show that the angular portion 176 can have a linear profile in cross-section to provide a frusto-conical portion of the passage 166. FIG. 5 shows that in some embodiments, the second collar opening 168 is larger than the first collar opening 164.

As discussed further below, a secure connection is provided in at least one configuration of the articular assembly 104 between the collar 108 and the locking ring 112. The collar 108 preferably is configured to facilitate disengagement of the locking ring 112 from the collar 108 where appropriate. For example, the collar 108 can include an aperture 180 to provide access to a portion of the locking ring 112 disposed within the collar 108. The aperture 180 can be disposed in the distal portion 146 of the collar 108. For example, the aperture 180 can be located at the distal end of the collar 108 and can be extend proximally therefrom. The aperture 180 can have a semicircular shape with a diameter thereof located at the distal end of the collar 108. The aperture 180 can comprise a shape that matches the shape of a working end of a removal tool 324, discussed below in connection with FIGS. 16A and 21. While the aperture 180 has a semicircular shape, it is also contemplated the aperture 180 can have any suitable shape and/or configuration capable of interaction with the removal tool 324.

FIGS. 3, 8, 16A, and 21 show that the aperture 180 is configured to permit the removal tool 324 to be advanced into the aperture 180 and to disengage the locking ring 112 from the collar 108. FIG. 3 shows that the aperture 180 provides access to the locking ring 112 in the configuration illustrated therein. FIGS. 20B and 21 show the locking ring 112 in the locked configuration, in which the locking ring 112 is secured by being advanced distally relative to the collar 108. In this configuration, a distal portion of the locking ring 112 is disposed over the first collar opening 164 and interference is provided between the distal portion 150 of the locking ring 112 and a distal portion of the collar wall 160 to secure the locking ring 112 to the collar 108. In the locked configuration, the locking ring 112 remains accessible through the aperture 180. FIG. 8 shows that a compressive force F1 can be applied through the aperture 180 by the removal tool 324. The force F1 can be directed inward, e.g., transverse to the longitudinal axis of the stem 124. The force F1 can be directed axially, e.g., generally proximally and/or distally or generally aligned to the longitudinal axis of the stem 124. The force F1 can be sufficient to compress the locking ring 112 to allow it to move proximally into the collar 108, e.g., to the position of FIG. 3 or to the free configuration at a position even closer to the articular member 116 where the gap G1 is smaller than depicted in FIG. 4.

FIGS. 7 and 8 show that in some embodiments the interior collar surface 172 has at least one collar connection feature 184 for attachment to the articular member 116. The connection feature 184 can be disposed adjacent to the second opening 168. The connection feature 184 is configured to engage the peripheral surface of the articular member 116 to retain the member 116 in the collar 108. The collar connection feature 184 can include a peg, a barb, a thread, or other protruding structure configured to receive or be received by the articular member 116 by a screw fit, snap fit, interference fit, or otherwise. The connection feature 184 can include at least one anti-rotational feature 188 configured to prevent rotational displacement of the articular member 116 relative to the collar 108 when the articular member 116 and the collar 108 are engaged. The anti-rotation features 188 can include a groove, a scallop, a notch, a cavity, or other receding structure configured to receive or be received by the articular member 116. FIGS. 5 and 8 show that the anti-rotation feature 188 can includes an array of such scallops that extend outward into the collar wall 160. In one embodiment, the array of anti-rotation feature 188 includes a plurality of such features disposed along an axis of insertion of the articular member 116 (e.g., a proximal-distal axis of the articular assembly 104). In one embodiment, the array of anti-rotation feature 188 includes a plurality of such features disposed about the inner circumference of the collar, e.g., about the wall 172 at any one position along the axis of insertion of the articular member 116 (e.g., the proximal-distal axis of the articular assembly 104). In one embodiment, the array of anti-rotation feature 188 includes a plurality of such features disposed along the axis of insertion of the articular member 116 and about the inner circumference of the collar, e.g., about the wall 172 at any one position along the axis of insertion of the articular member 116. The connection feature 184 is configured to engage the projection or the distal portion 142 of the articular member 116 by interference fit or otherwise to prevent axial movement (e.g., the proximal-distal direction) or rotation (e.g., about the proximal-distal direction) of the member 116 in the collar 108.

Figure 25:
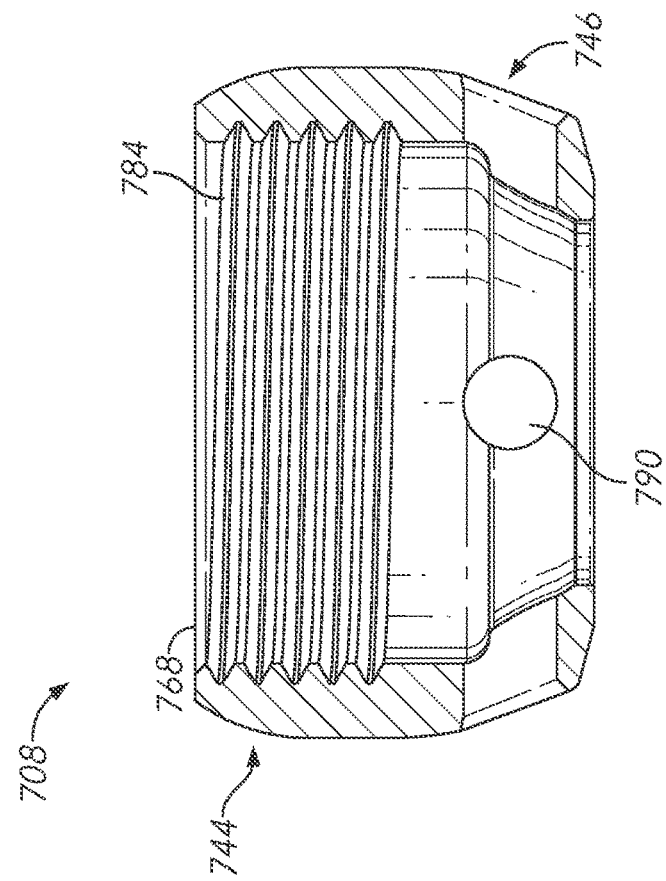
FIG. 25 illustrates a cross-section view of a collar of the articular assembly of FIG. 24.
Figure 24:
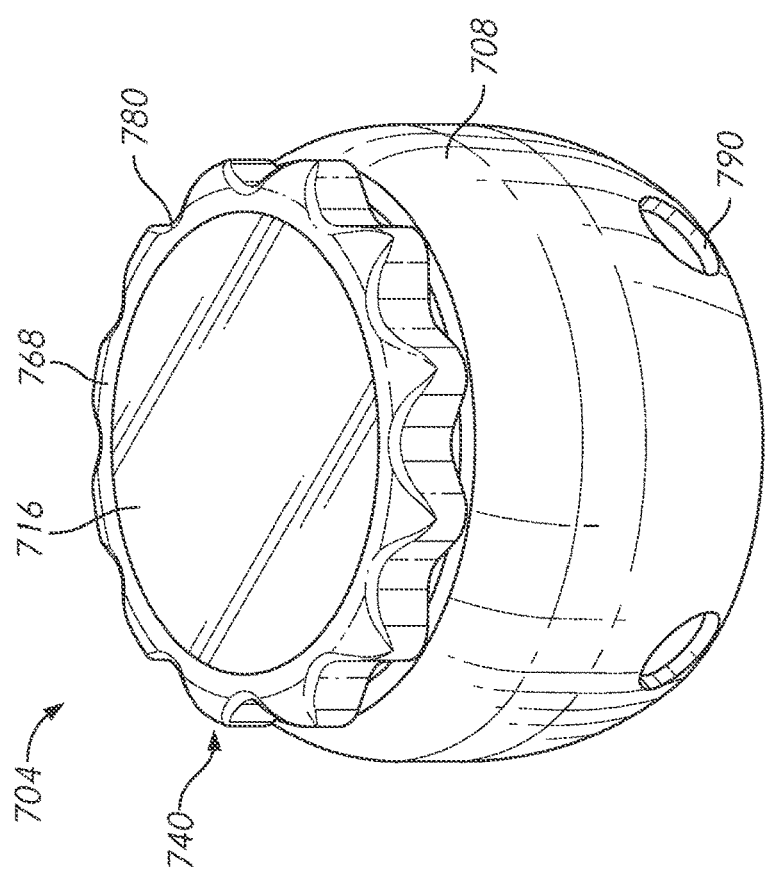
FIG. 24 illustrates a perspective view of another embodiment of an articular assembly as disclosed herein.
Figure 26:
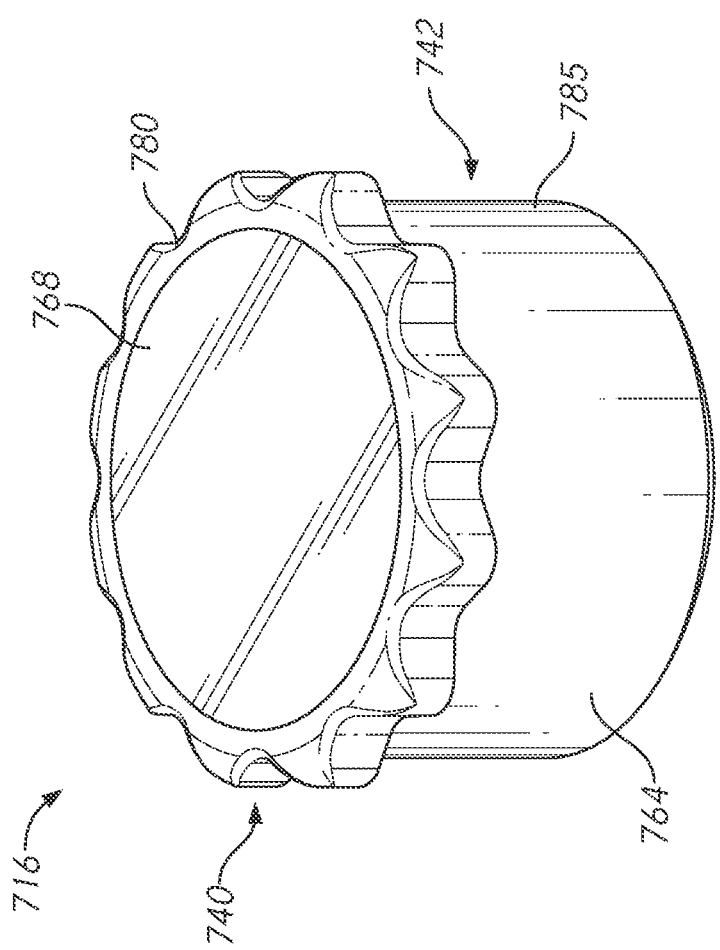
FIG. 26 illustrates a perspective view of an articular member of the articular assembly of FIG. 24.

FIGS. 24-26 show that, in certain embodiments, a collar connection feature 784 of a collar 708 for attachment to an articular member 716 may comprise one or more threads (see FIG. 25). FIGS. 24-26 are various views of an articular assembly 704 for an elbow joint prosthesis, according to some embodiments. Unless otherwise noted, similar reference numerals in FIGS. 24-26 refer to components that are the same as or generally similar to the components in other figures discussed herein with similar features. It will be understood that the features described with reference to articular assembly 704 shown in FIGS. 24-26 can be used with any of the embodiments described and/or contemplated herein. It will also be understood that any feature, structure, material, step, or component of any embodiment described and/or illustrated herein can be used with or instead of any other feature, structure, material, step, or component of any embodiment of the articular assembly 704 shown in FIGS. 24-26.

In some embodiments, the one or more threads of the collar 708 can be disposed adjacent to the second opening 768 of the collar 708 and be configured to engage the peripheral surface 785 (as shown in FIG. 26) of the articular member 716, e.g., as the articular assembly 704 transitions from an unlocked configuration to a locked configuration. In some embodiments, the articular member 716 may have an unlocked position and a locked position within the collar 708. For example, FIG. 24 is a perspective view showing that, when the articular assembly 704 is in a locked position, at least a portion of the projection 764 of the articular member 716 may be engaged with the one or more threads (not shown in FIG. 24) of the collar 708. In this manner, the articular member 716 may be rotated relative to the collar 708 to facilitate engagement of the peripheral surface 785 of the articular member 716 with the one or more threads.

Rotating the articular member 716 relative to collar 708 advantageously allows the articular member 716 to engage with and/or translate along the one or more threads to move the articular member 716 from the unlocked configuration to the locked configuration. The peripheral surface 785 of the articular member 716, in certain embodiments, can be engaged with the one or more threads with an interference fit. The articular member 716, in some embodiments, can comprise a semi-rigid material capable of deformation when a force is applied. This can advantageously allow the peripheral surface 785 of the articular member 716 to temporarily and/or permanently deform when the peripheral surface 785 interacts with the collar connection feature 784 (e.g., one or more threads) of the collar 708. In some embodiments, the articular member 716 can comprise a rigid material that is sufficiently pliable to permit the peripheral surface 785 to engage with a portion of the collar 708. For example, an outer periphery of the peripheral surface 785 of the articular member 716 can be larger than an inner periphery of the one or more threads such that at least some deformation of the peripheral surface 785 of the articular member 716 occurs upon engaging the articular member 716 with the collar 708. The material of the articular member 716 and/or the collar 708 may enable the articular member 716 to be deformed, e.g., compressed, upon engagement with the one or more threads to create an interference fit.

In some instances, the articular member 716 may comprise corresponding threads along at least a portion of the peripheral surface 785 of the articular member 716 configured to interact with the threads 74 of the collar 708. For example, the articular member 716 may be rotated clockwise or counterclockwise to engage the one or more threads of the collar 708 with corresponding threads of the articular member 716. After engagement, the articular member 716 may remain engaged to the collar 708.

To facilitate rotation of the articular member 716 relative to the collar 708, in certain embodiments, at least a portion of the articular member 716 can be configured to be gripped during attachment or screwing of the articular member 716 onto the collar 708. For example, in some embodiments (as illustrated in FIGS. 24 and 26), an outer surface and/or outer rim of a base 768 of the articular member 716 can comprise a one or more gripping elements 780 configured to increase friction and/or provide one or more surfaces on which a finger, palm, or tool can exert a rotational force to facilitate attachment or removal of the articular member 716 from the collar 708. The gripping element 780 can include one or more grooves, scallops, notches, cavities, or other structure configured to facilitate rotation of the articular member 716 relative to the collar 708. FIGS. 24 and 26 show that the gripping element 780 can includes an array of such notches that extend inwardly into the base 768 of the articular member 716. In one embodiment, the array of gripping elements 780 includes a plurality of such elements disposed along an outer circumference of the articular member 716.

The gripping element 780 and/or outer rim of the base 768 can have a distal face that extends from adjacent to a proximal end of the projection 764 to an outer periphery. The distance between the proximal end of the projection 764 and the outer periphery of the gripping element 780 can correspond to a width of the gripping element 780. The width of the gripping element 780 can be constant. The gripping element 780 and/or outer rim of the base 768 can be configured to interface with the proximal portion 744 of the collar 708, as discussed in reference to other figures discussed herein with similar features.

FIGS. 24 and 25 show that the articular assembly 704 can be configured to interact with a collar locking tool to advantageously facilitate attachment and/or removal of the articular member 716 to the collar 708. The locking tool may have a distal end configured to engage with at least a portion of the collar 708 to prevent rotational movement of the collar 708 as the articular member 716 is being attached to the collar 708. For example, in some embodiments, the collar locking tool may comprise a screwdriver, pliers, or any other tool suitable to interact with the articular assembly 704.

The collar locking tool can be configured to abut against and/or be inserted into a collar aperture 790 disposed within the collar 708. The aperture 790 can be disposed in the distal portion 746 of the collar 708. For example, the aperture 790 can be located at a distal end of the collar 708. In certain embodiments, the collar 708 may comprise a plurality of apertures 790 along a distal portion 746 of the collar 708. The aperture 790 can have a circular shape with a diameter thereof corresponding to a diameter of the looking tool. The aperture 790 can comprise a shape that matches the shape of a working end of the locking tool. While the aperture 790 is illustrated in FIGS. 24 and 25 as having a circular shape, it is also contemplated the aperture 790 can have any suitable shape and/or configuration capable of interaction with the locking tool. When so engaged, maintaining the position of the locking tool can cause the collar 708 to remain substantially stationary while a rotational force is being applied to the articular member 716 to engage and/or disengage the articular member 716 with the collar 708. As the articular member 716 is rotated in an engagement direction relative to the collar 708, the articular assembly 704 transitions from an unlocked configuration to a locked configuration.

Figure 10:
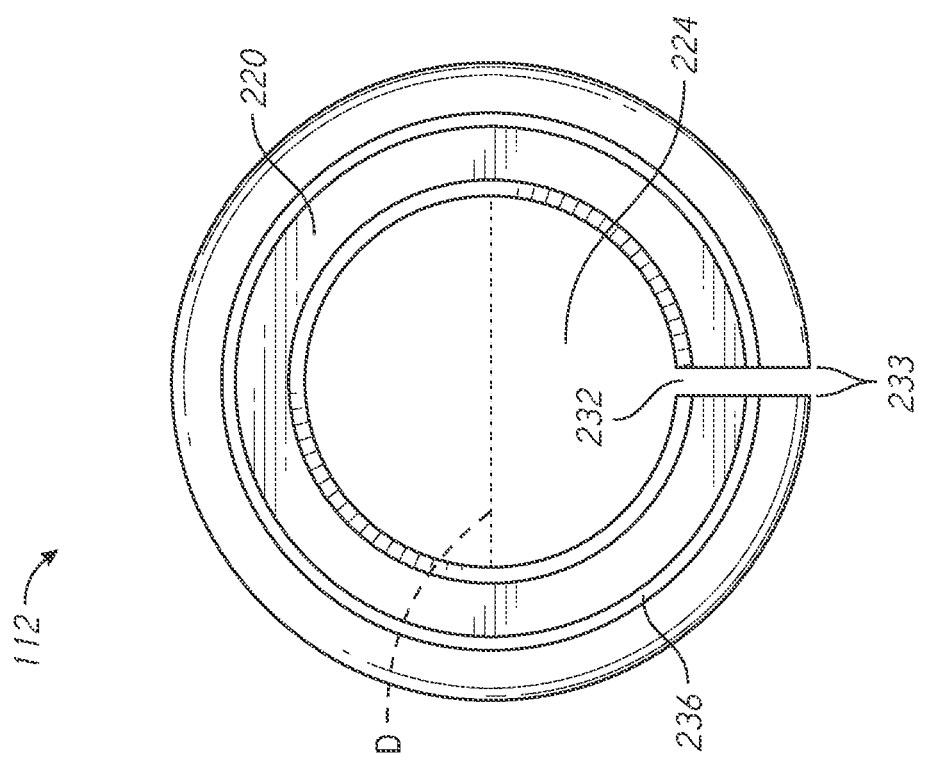
FIG. 10 is a bottom view of the locking ring of FIG. 9.
Figure 9:
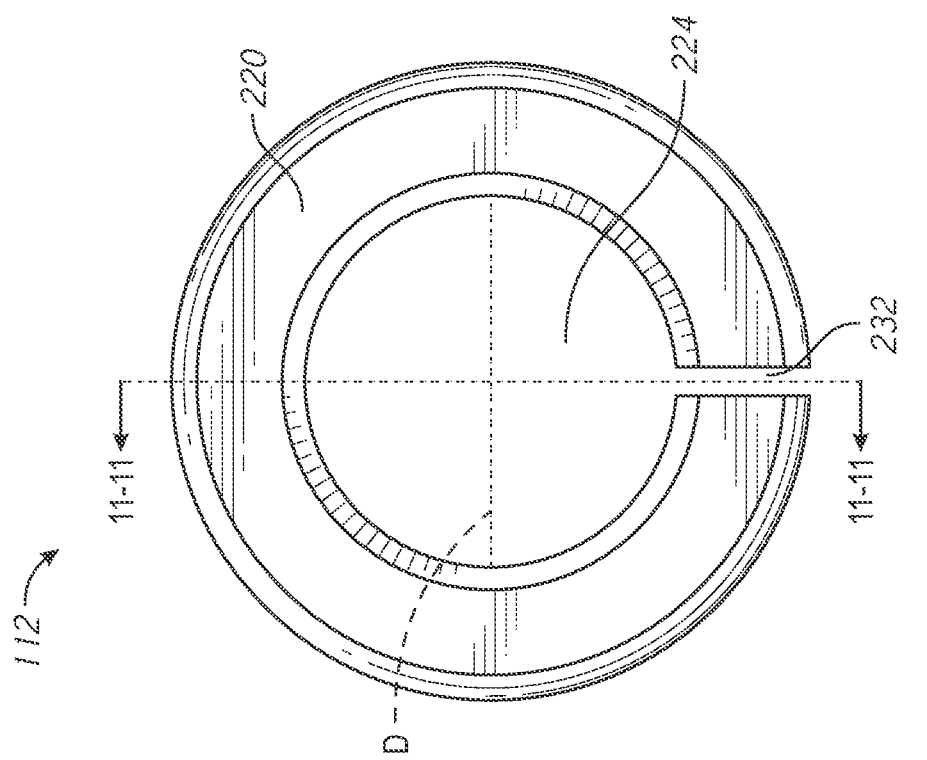
FIG. 9 is a top view of a locking ring of the articular assembly of FIG. 3.

FIGS. 9-11 show various views of the locking ring 112 of the articular assembly 104. The locking ring 112 has a ring wall 220 that extends between an outer periphery of the locking ring 112 and an inner periphery of the locking ring 112. The ring wall 220 defines a ring opening 224. The ring wall 220 can have an angular outer surface 228 and a slot 232 configured to permit the ring wall 220 to expand and to be compressed. The angular outer surface 228 is configured to engage the angular portion 176 of the interior collar surface 172 when the stem 124 is coupled with the articular assembly 104, e.g., when in the locked configuration with the articular head 128 disposed within the assembly 104. The locking ring 112 is configured to expand when in the free configuration to allow the articular head 128 to pass through the ring opening to be disposed within the collar 108. For example, the slot 232 is defined between two free ends 233 of the locking ring 112. The two free ends 233 can move both towards and away from each other in one embodiment when in a free configuration, e.g., when not fully constrained within the collar 108. The free ends 233 are constrained to some extent when the locking ring 112 is in the locked configuration, e.g., when engaged with the collar 108. For instance, in the position shown in FIGS. 3 and 4, the movement of the free ends 233 of the locking ring 112 away from each other is limited by the interior collar surface 172. Greater movement of the free ends 233 of the locking ring 112 away from each other can occur as the locking ring 112 is moved toward the articular member 116 and the gap G1 is decreased. This property of the articular assembly 104 is useful in the coupling thereof with the stem 124. The movement of the free ends 233 of the locking ring 112 away from each other is further constrained in the position of FIGS. 20B and 21, as will be discussed further below. Movement of the free ends 233 of the locking ring 112 toward each other can be enhanced by the aperture 180, as discussed above. In some embodiments the slot 232 is small, with the free ends 233 very close to each other, e.g., with no significant gap between the ends 233, in a free state. In such embodiments, the materials flexibility or deformability or ductility can enable the locking ring 112 to be secured in the collar 108.

The ring wall 220 of the locking ring 112 has an interior ring surface. The interior ring surface includes a proximal portion 238 adjacent to the proximal portion 148 of the locking ring 112. The proximal portion 238 may be tapered. The taper angle and length of the proximal portion can be configured to interface with the articular head 128 of the stem 124 when the stem 124 is coupled with the articular assembly 104, e.g., with the articular head 128 disposed through the locking ring 112. The proximal portion 238 may be shaped to correspond to the shape of the articular head 128 of the stem 124 when the locking ring 112 is in the locked configuration. The proximal portion 238 can include a spherical surface that matches the curvature of the articular head 128. The proximal portion 238 may extend along the entire width of the ring wall 220.

The interior ring surface may have a middle portion 242. The middle portion 242 can be substantially straight or tapered. The middle portion 242 defines an inner diameter D of the locking ring 112. The inner diameter D can increase as the locking ring 112 is expanded to permit insertion of the stem 124 into the articular assembly 104. For example, if the locking ring 112 has free ends 233, the inner diameter D can expand as the free ends 233 move away from each other. When the locking ring 112 is in the free configuration, the inner diameter D may be the same as or smaller than a width of the articular head 128 of the stem 124. When the locking ring 112 is in the locked configuration, the inner diameter D may be smaller than a width of the articular head 128 of the stem 124 to inhibit disengagement of the stem 124 form the locking ring 112.

The interior ring surface can include a distal portion 240 adjacent to the distal portion 150 of the locking ring 112. The distal portion 240 is configured such that a portion thereof adjacent to the middle portion 242 of the interior ring surface is closer to a central longitudinal axis A4 of the locking ring 112 than is a portion thereof adjacent to the distal portion 150 of the locking ring 112. The distal portion 240 can have a symmetrical configuration about the axis A4 providing a conical and/or curved portion of the ring opening 224. In some embodiments, an inner diameter of the distal portion 240 is larger than an inner diameter of the proximal portion 238. The distal portion 240 can have a distally enlarging structure that provide increasing diameter in the free configuration from the middle portion 242 toward the distal portion 150. The range of diameters preferably extends to a diameter larger than the diameter of the articular head 128 so that the distal portion 240 can receive the articular head 128 and rest thereon prior to assembly, as discussed below.

The distal portion 150 of the locking ring 112 may include at least one ring connection feature 236. The ring connection feature 236 can protrude from the ring wall 228 of the locking ring 112. The ring connection feature 236 is disposed adjacent to the distal portion 240. The ring connection feature 236 is configured to engage the collar wall 160 to retain the locking ring 112 in the collar 108. The ring connection feature 236 can include a peg, a barb, a screw, or other protruding structure, configured to engaged the first collar opening 164 by a screw fit, snap fit, interference fit, or otherwise. Each ring connection feature 236 can be configured to inhibit disengagement of the locking ring 112 from the locked configuration. In some embodiments, the ring connection feature 236 is a flange extending radially outward from an end of the ring wall 220. The connection feature 236 can include an external concave structure that can receive a portion of the collar 108, as discussed herein. The external concave structure can include a circumferential groove 237 that extends around the locking ring 112. The circumferential groove 237 can extend entirely around the locking ring 112 between the free ends 233 thereof, in one embodiment.

FIGS. 12-15 show various views of the articular member 116 of articular assembly 104. While the following discussion references articular member 116 as shown in FIGS. 12-15, the articular member 116' shown in FIGS. 4A and 4B is similar to articular member 116 shown in FIGS. 12-15. As such, it will be understood that the features described with reference to articular member 116 can be used with any other articular member described and/or contemplated herein. For example, articular member 116' of FIGS. 4A and 4B may include any feature, structure, material, step, or component described herein with reference to articular member 116 of FIGS. 12-15, unless otherwise noted.

The proximal portion 140 of the articular member 116 has a base 260. The distal portion 142 of the articular member 116 includes a projection 264 that protrudes from the base 260. In some embodiments, the base 260 can include an outer rim 268. The outer rim 268 can be disposed adjacent to the projection 264. The outer rim 268 can have a distal face 269 that extends from adjacent to a proximal end of the projection 264 to an outer periphery. The outer periphery of the outer rim 268 can be spaced a distance radially or transversely away from the proximal end of the projection 264. The distance between the proximal end of the projection 264 and the outer periphery of the outer rim 268 can correspond to a width of the outer rim 268. The width of the outer rim can be constant. The outer rim 268 can be configured to interface with the proximal portion 144 of the collar 108, as discussed previously.

In some embodiments, the base 260 includes a first concave surface 272. The first concave surface 272 can be disposed on a proximal surface of the base 260. For example, the first concave surface 272 can be located at a proximal end of the base 260 and can define recessed surface therein. The first concave surface 272 is configured to receive at least a portion of a corresponding humeral component, e.g., the humeral spool 18. The first concave surface 272 can be rounded, e.g. semicircular shape. The first concave surface 272 can have a smooth surface or other structure or treatment adapted to facilitate rotation along at least a portion of the humeral spool. The first concave surface 272 can be a region of the proximal portion 140. The first concave surface 272 can be disposed on a separate member that is inserted into and retained by the proximal portion 140.

The projection 264 of the articular member 116 extends from the base and can have a peripheral surface 284. The peripheral surface 284 is configured such that the peripheral surface 284 extends substantially parallel to a central longitudinal axis A8 of the articular member 116. The peripheral surface 284 can have a symmetrical configuration about the axis A8. The peripheral surface 284 of the projection 264 can be spaced a distance radially or transversely away from the central longitudinal axis A8. The distance between the peripheral surface 284 and the central longitudinal axis can correspond to a radius of the projection 264. The radius, and corresponding width, of the projection 264 can be substantially constant. The projection 264 can be configured to interface with the interior collar surface 172 of the collar 108. In some embodiments, the peripheral surface 284 includes at least one projection connection feature to facilitate attachment to the interior collar surface 172. Each projection connection feature can be a peg, a barb, a thread, or other protruding structure configured to receive or be received by the interior collar surface 274 by a screw fit, snap fit, interference fit, or otherwise. For example, the width of the projection 264 can be larger than the periphery of the interior collar surface 172, such that at least some deformation of the projection 264 occurs upon mating the articular member 116 with the collar 108. In some instances, the projection connection feature can include a threaded portion to threadably engage the interior collar surface 172.

The projection 264 may have a second concave surface 276. The second concave surface 276 can be disposed on a distal face of the projection 264. For example, the second concave surface 276 can be located between the first concave surface 272 and a distal end surface 280 of the articular member 116 opposite the first concave surface 272. The second concave surface 276 is configured to receive at least a portion of the articular head 128 of the stem 124 when the stem 124 is coupled with the articular assembly 104. The second concave surface 276 may be shaped to correspond to the shape of the articular head 128. The second concave surface 276 can be rounded, e.g. semicircular shape. The second concave surface 276 can have a smooth surface or other structure or treatment adapted to facilitate rotation along at least a portion of the articular head 128.

The distal portion 142 of the articular member 116 extends proximally from the distal end surface 280 of the articular member 116. The distal end surface 280 may be tapered. The taper angle and length of the distal end surface 280 can be configured to facilitate insertion of the articular member 116 into the collar 108. The taper may extend along at least a portion of the end surface 280. The distal end surface can have a symmetrical configuration about the axis A8 providing a curved portion extending along an outer periphery of the second concave surface 276.

The articular member 116 and the locking ring 112 at least partially define an articular space 120 within the collar 108 when the articular assembly 104 is fully assembled (as shown in FIGS. 3-4B, 20B, 21, and 23E). The articular space is configured to receive and retain the articular head 128 of the stem 124. For instance, the articular space 120 can have a generally spherical shape to permit the articular assembly 104 to pivot about the stem 124, particularly when the radial head assembly 100 experiences a side load. The spherical space can be made up of spherical surfaces on the locking ring 112 and the articular member 116.

The articular assembly 104 is capable of bipolar articulation when the articular head 128 is inserted within the articular space 120, e.g., when the articular assembly 104 is in the locked configuration. Bipolar articulation can provide for rotation of the articular member 116 over the articular head 128 and articulation of the articular member 116 over the spherical portion of the humeral spool 18. The engagement mechanism though which the articular assembly 104 interacts with the articular head 128, e.g., including the manner in which the locking ring 112 engages the collar 108, as described herein, provides an enhanced attachment security. The enhanced security reduces the risk of dislocation and/or decoupling as the radial head assembly 100 may become subject to a variety of radial motions and loading forces.

B. Radial Head Assembly Kits for Implanting and/or Removing an Articular Assembly FIG. 16A shows an elbow joint prosthesis kit 320A that can be provided. The kit 320A includes an articular assembly 104, a stem 124, a removal tool 324 and a locking tool 328. During a normal elbow joint replacement procedure, the stem 124 may be used to anchor the articular assembly 104 to the radius when they are assembled into the radial head assembly 100, as discussed herein. It may be advantageous to provide for the removal of the articular assembly 104 through the inclusion of a removal tool 324 in kit 320A.

FIG. 16A illustrates an example of the removal tool 324. The removal tool 324 may have a distal end with a projection 326. The projection 326 can be configured to be inserted through the aperture 180. When so inserted, acting on the proximal end of the tool 324 can cause the force F1 (as shown in FIGS. 21 and 22) to be applied to the locking ring 112 to disengage the locking ring 112 from the collar 108. When in the locked configuration, the locking ring 112 engages the collar wall 160 to retain the locking ring 112 in the collar 108, as discussed above. For example, an edge of the collar 108 is received by the ring connection feature 236 securing the locking ring 112 and the articular head 128 in position. The removal tool 324 can apply a compressive force F1 (as shown in FIGS. 8, 11, and 21) through the aperture 180 to at least a portion of the locking ring 112. The compressive force F1 compresses the locking ring 112 and causes the two free ends 233 to move towards each other. As the two free ends 233 move toward each other, a width of the locking ring 112 decreases and the ring connection feature 236 can disengage from the edge of the collar wall 160. Once disengaged from the collar wall 160, the locking ring 112 may be advanced toward the articular member 116 from a position in the locked configuration to another second position in the free configuration. The free configuration permits the locking ring 112 to expand and the articular head 128 to pass through the locking ring 112. As such, the articular assembly 104 can be removed from the stem 124.

With continued reference to FIG. 16A, the kit 320A may comprise a locking tool 328. The locking tool 328 may have a distal end with a collar engagement portion 330 and an articular member engagement portion 332. The collar engagement portion 330 can be configured to abut against a distal end face of the collar 108, and the articular member engagement portion 332 can be configured to abut against a proximal end face of the articular member 116'. The collar engagement portion 330 and/or the articular member engagement portion 332 can, in some instances, be configured to engage any other portion of the radial head assembly 100' to transition the articular assembly 104' from an unlocked configuration to a locked configuration. When so engaged, acting on the proximal end of the locking tool 328 can cause the forces F10 and F10' (as shown in FIG. 23C) to be applied to the articular assembly 104' to move the articular member 116' and the locking ring 112 in a distal direction relative to the collar 108. As the articular member 116' and the locking ring 112 are distally displaced, the articular assembly 104' transitions from an unlocked configuration to a locked configuration. As discussed herein, when in the locked configuration, the locking ring 112 engages the collar wall 160 to retain the locking ring 112 in the collar 108. For example, an edge of the collar 108 is received by the collar engagement portion 330 securing the collar 108 in position. The locking tool 328 can apply one or more compressive forces F10 and F10' (as shown in FIGS. 23C and 23E) to the articular member 116' through the articular member engagement portion 332. The compressive forces F10, F10' causes the articular member 116' to move distally relative to the collar 108, contact a proximal face of the locking ring 112, and, in turn, moves the locking ring 112 in a distal direction relative to the collar 108. As the locking ring 112 is moved, the locking ring 112 engages with the collar 108 to enter a locked configuration.

Elbow joint prosthesis kits, according to some embodiments, may include multiple articular assemblies 104 of different sizes to better fit a full range of patients. In some embodiments of a kit the stem 124 comes in varying sizes, such as with different heights for the head 128. FIG. 16B illustrates a kit 320B including a plurality of, e.g., at least four, articular assemblies 104 of various sizes and at least one removal tool 324. The various articular assemblies 104 permit the implantation of an articular assembly that matches the patient's anatomy. More or fewer than four sizes can be provided. More than one removal tool 324 can be provided if the aperture 180 is modified based on the size. In some embodiments, a removal tool can be configured to be used on more than one size, such as by having tapered working ends and/or multiple working features as shown in FIG. 20C.

The articular assembly 104 for the elbow joint prostheses may be selected and implanted according to a range of one or more sizes for a given corresponding humeral spool 18. For example, FIG. 16B illustrate three different sizes of articular assembly 104. FIG. 16B shows an articular assembly 104', an articular assembly 104" that is larger than articular assembly 104'; and an articular assembly 104''' that is larger than articular assembly 104". The different sizes of articular assemblies 104', 104", 104''' permit the articular assembly to correspond with the respective humeral spool in the elbow joint. In some embodiments, the kit may include a multiplicity of articular assemblies 104 of the same size. For example, FIG. 16B illustrates a kit 320B with at least two large articular assemblies 104".

As discussed above, the inclusion of the removal tool 324 permits the removal of the articular assembly 104 following implantation. If an implanted articular assembly 104 is determined to not be the proper size for the patient, the removal tool 324 may be used to remove and replace the implanted articular assembly 104 with one of a different size included in the kit 320B. This is superior to existing radial head assemblies which often have a fixed assembly size that may not be removed and/or replaced after the articular assembly is implanted.

C. Radial Head Assemblies with an Alternative Locking Ring Engagement Mechanism

FIG. 17 shows another embodiment of a radial head assembly 400. The radial head assembly 400 resembles or is similar to the radial head assembly 100 except as described differently below. Accordingly, numerals used to identify features of the radial head assembly 100 shown in FIGS. 2-15 are incremented by a factor of 300 to identify similar features of the radial head assembly 400 shown in FIG. 17. The foregoing descriptions can be combined with the specific discussion below in other various embodiments.

The radial head assembly 400 includes an articular assembly 404 and a stem 424. The articular assembly 404 includes a collar 408, a locking ring 412, and an articular member 416. FIG. 17 shows that in one configuration the locking ring 412 is disposed within the collar 408 and the articular member 416 is at least partially disposed within the collar 408. The locking ring 412 can be configured to be advanced into the collar 408, e.g., with at least a portion of the locking ring 412 being disposed within a first opening of the collar 408, as discussed in further detail below.

The collar 408 has a collar wall that extends between an outer periphery of the collar 408 and an inner periphery of the collar 408. The collar wall defines the first collar opening, a second collar opening, and a passage therethrough. The first collar opening is disposed at a distal end 446 of the collar 408. The second collar opening is disposed at the proximal end 444 of the collar 408. The collar wall can have an interior collar surface configured to couple with the locking ring 412.

In some embodiments, the interior collar surface has an inner rim 450. The inner rim 450 can be disposed adjacent to a distal end of the collar wall. The inner rim 450 can have an inner face that extends from adjacent to a distal end of the collar wall to an inner periphery. The inner periphery of the inner rim 450 can be spaced a distance radially or transversely away from the distal end of the collar wall. The distance between the distal end of the collar wall and the inner periphery of the inner rim 450 can correspond to a width of the inner rim 450. The width of the inner rim 450 can be constant. The inner rim 450 can be configured to interface with a mating surface 462 of the locking ring 412, discussed in further detail below. The inner rim 450 is configured to abut the locking ring 412 when the locking ring 412 is inserted into the collar 408. In this configuration, the inner rim 450 engages the locking ring 412 and prevents the locking ring 412 from expanding radially such that an articular head 426 of the stem 424 coupled with the articular assembly 404 can be retained within an articular space 420.

The inner rim 450 can have an angular portion 454 proximate to the first collar opening. The angular portion 454 of the inner rim 447 may correspond with a distal end 458 of the locking ring 412. The distal end 458 also can have an angular portion. The angular portion 454 may facilitate expansion of the locking ring 412 as the locking ring 412 is advanced proximally within the collar 408. Also, the angular portion 454 can facilitate compression by the sliding of the angular portion of the distal end 458 over the angular portion 454. Specifically, the angular portion 454 forces the ring inward as the angular portion of the distal end 458 moves over the angular portion 454.

The locking ring 412 has a proximal portion and a distal portion. The proximal portion can include a mating surface 462 configured to engage the inner rim 450, as shown in FIG. 17. The mating surface 462 can have a dimension that is greater at least in part than an inner periphery of the inner rim 450. This configuration allows the locking ring 412 to be inserted until the mating surface 462 abuts the inner rim 450. The abutment of the mating surface 462 with the inner rim 450 provides a positive stop for the locking ring 412, preventing the ring 412 from pulling out upon application of a force away from the articular member 416. In some embodiments, the distal portion of the locking ring 412 can be secured within the first collar opening with an interference fit. For example, an outer periphery of the distal portion of the locking ring 412 can be larger than an inner periphery of the first collar opening such that at least some deformation of the distal portion occurs upon mating the locking ring 412 with the collar 408. The material of the locking ring 412 and/or the collar 408 may enable the locking ring 412 to be deformed, e.g., compressed, upon insertion to create an interference fit.

The axial length of the locking ring 412, e.g., along the direction from the proximal portion to the distal portion thereof, can be greater than the axial length of the inner rim 450 such that the distal end 458 of the locking ring 412 is proximal of a distal end of the collar 408 while the proximal end of the locking ring 412 is proximal of the inner rim 450. FIG. 17 shows that the distal end 458 of the locking ring can be advanced more than half way into the first collar opening. A proximal end of the locking ring 412 may be disposed well short of a distal end of the articular member 416, which provides a range of motion of the locking ring 412.

FIG. 17 further shows that when the distal end of the locking ring 412 is disposed at the same position as the distal end of the collar 408 there is a gap G4 between the proximal end of the locking ring 412 and the distal end of the articular member 416. The gap G4 corresponds to one position of the locking ring 112 along a range of motion of the locking ring 412 in an axial direction within the collar 408. Motion of the locking ring 412 in the axial direction advantageously allows the locking ring 412 to move from a position in the collar 408 in which the ring 412 is confined or constrained by the collar 408, e.g., by radially inwardly facing features of the inner rim 450 (as shown in FIG. 17) to a position in which it is relatively less constrained or confined. Reducing the confinement or constraint imposed by the collar 408, e.g., by the inner rim 450, on the locking ring 412 allows the locking ring 412 to expand. For example, movement of the locking ring 412 toward the articular member 416 reduces the gap G4 but moves the locking ring 412 to a position at which the distal end 458 of the locking ring is disposed proximal to the inner rim 450. In the portion of the collar 408 proximal to the inner rim 450, a larger transverse width is provided, which is sufficient to allow the ring 412 to expand to allow the head 426 of the stem 424 to be withdrawn from the collar 408.

D. Radial Head Assemblies with an Articular Portion Coupled to a Stem

Figure 19:
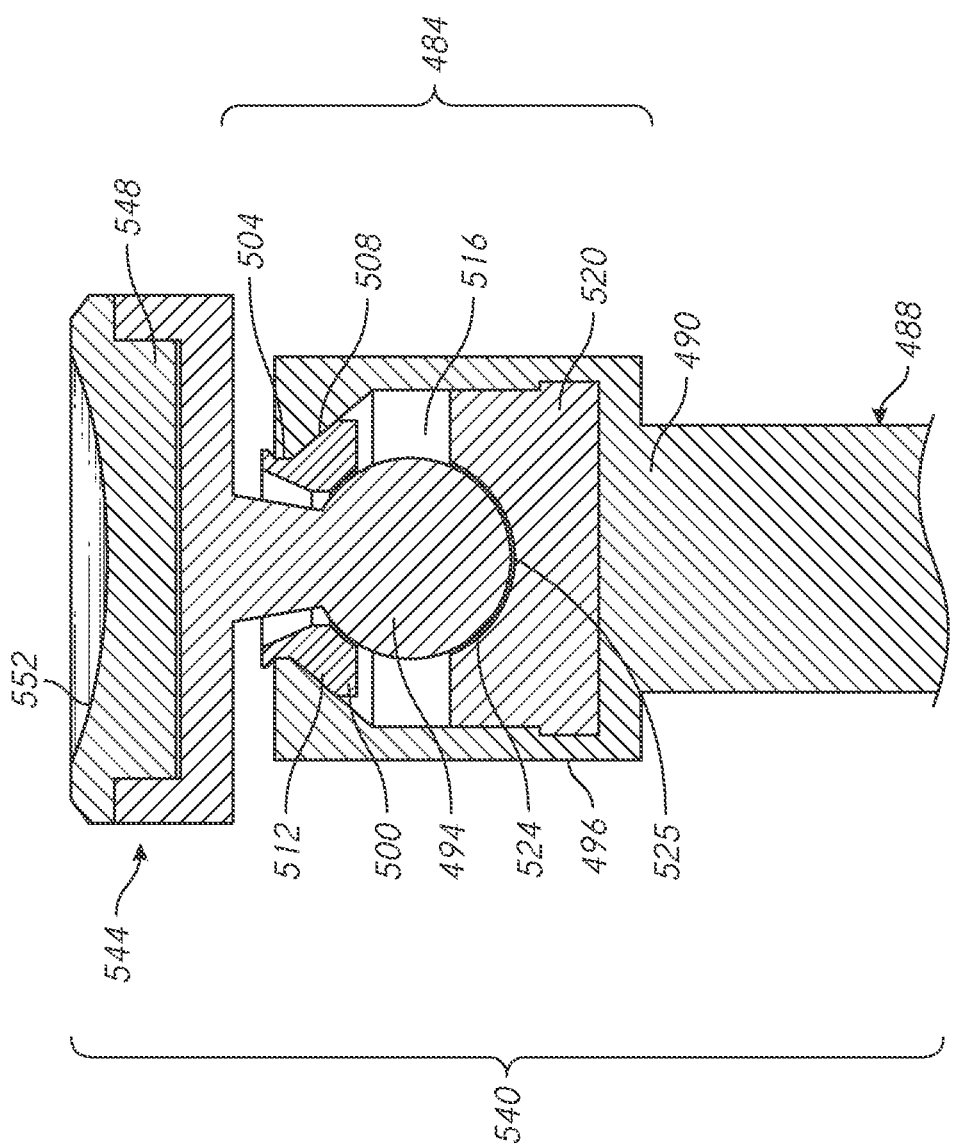
FIG. 19 illustrated a further embodiment of a radial head assembly as disclosed herein.

FIGS. 18 and 19 show other embodiments of a radial head assembly that is similar to the radial head assembly 100, except as described differently below. The foregoing descriptions can be combined with the specific discussion below in other various embodiments.

In another embodiment, an articular assembly 480 includes a first articular member 492 and an articular portion 484 that is configured to couple with a stem 488 coupled with a first bone. The articular portion 484 has a collar 496 and a trapping member 500. The stem 488 includes a proximal portion 490 and a distal portion. The distal portion of the stem 488 extends from the proximal portion 490 toward a distal end of the stem 488. The distal portion 490 is configured to be embedded in bone, e.g., in the radius bone adjacent to an elbow, as discussed above. The proximal portion 490 can include the articular portion 484. The articular portion 484 can be disposed on or extend from a proximal end of the stem 488.

The first articular member 492 has a proximal portion and a distal portion. The proximal portion has a base 493. The proximal portion can include an outer rim disposed adjacent to the distal portion. The outer rim can have a distal face that extends from adjacent to a proximal end of the distal portion to an outer periphery. The outer periphery of the outer rim can be spaced a distance radially or transversely away from the proximal end of the distal portion. The distance between the distal portion and the outer periphery of the outer rim can correspond to a width of the base 493. The width of the base 493 can be constant. The base 493 can be configured to interface with a proximal portion of the collar 496, as discussed previously.

In some embodiments, a first concave surface 495 is disposed on the base 493 of the first articular member 492 to face a second bone opposite the first bone. The first concave surface 495 can be disposed on a proximal surface of the base 493. For example, the first concave surface 495 can be located at a proximal end of the base 493 and can define recessed surface therein. The first concave surface 495 is configured to receive at least a portion of a corresponding humeral spool. The first concave surface 495 can be rounded, e.g. semicircular shape. The first concave surface 495 can have a smooth surface or other structure or treatment adapted to facilitate rotation along at least a portion of the humeral spool. The distal portion of the first articular member 492 includes a convex articular head 494. The articular head 494 can be configured to interface with the articular assembly 484.

The collar 496 has a collar wall that defines a collar opening 504 and an interior trapping surface 508 proximate to the collar opening 504. A space extends from the collar opening 504 into an interior of the collar 496. The trapping member 500 has a trapping member opening and a mating surface 512 configured to engage the interior trapping surface 508. The radial head assembly 480 has a configuration in which the interior trapping surface 508 engages a mating surface 512 of the collar 496 to prevent the trapping member 500 from expanding such that the articular head 494 disposed in an articular space 516 can be retained in the articular space 516.

The articular portion 484 may comprise a second articular member 520. The second articular member 520 may be disposed within the collar 496 and have a second concave surface 524. The second concave surface 524 can be disposed on a distal face 525 of the second articular member 520. The second concave surface 524 is configured to receive at least a portion of the articular head 494 of the first articular member 492 when the first articular member 492 is coupled with the collar 496. The second concave surface 524 may be shaped to correspond to the shape of the articular head 494. The second concave surface 524 can be rounded, e.g. semicircular shape. The second concave surface 524 can have a smooth surface or other structure or treatment adapted to facilitate rotation along at least a portion of the articular head 494.

FIG. 19 shows another embodiment of a radial head assembly with an articular portion coupled to a stem. Radial head assembly 540 is similar to the radial head assembly 480 of FIG. 18, except as described differently. FIG. 19 illustrates an embodiment of the radial head assembly 540 wherein the base 548 is removably engaged with the first articular member 544. In some instances, it may become necessary to remove the base 548 from the first articular member 544, for example, if at least one of the first articular member 544 and the first concave surface 552 begins to wear. Any suitable technique for joining the articular member 544 to the base 548 can be provided, including interference fit, mating tapers, barbs or hooks, locking rings, threads or other trapping features.

E. Radial Head Assemblies with Multiple Locking Rings

FIGS. 27-32 show that, in certain embodiments, a radial head assembly 800 may comprise two or more locking rings 812a, 812b. FIGS. 27-32 are various views of an articular assembly 804 for an elbow joint prosthesis, according to some embodiments. The radial head assembly 800 is similar to the radial head assembly 100, except as described differently below. Accordingly, unless otherwise noted, similar reference numerals in FIGS. 27-32 refer to components that are the same as or generally similar to the components of the assembly 100 or in the remaining figures discussed herein with similar features. It will be understood that the features described with reference to radial head assembly 800 shown in FIGS. 27-32 can be used with any of the embodiments described and/or contemplated herein. It will also be understood that any feature, structure, material, step, or component of any embodiment described and/or illustrated herein can be used with or instead of any other feature, structure, material, step, or component of any embodiment of the radial head assembly 800 shown in FIGS. 27-32.

FIG. 27 shows a cross-section view of an embodiment of a radial head assembly 800. The radial head assembly 800 can include an articular assembly 804 and a stem 824. The articular assembly 804 includes a collar 808, an articular member 816, a trapping member 870, and at least two locking rings 812a, 812b. In some embodiments, the proximal portion of the stem 824 can include a convex articular head 828 (as shown in FIG. 27). In the illustrated embodiment, the convex articular head 828 is semicircular.

Figure 29:
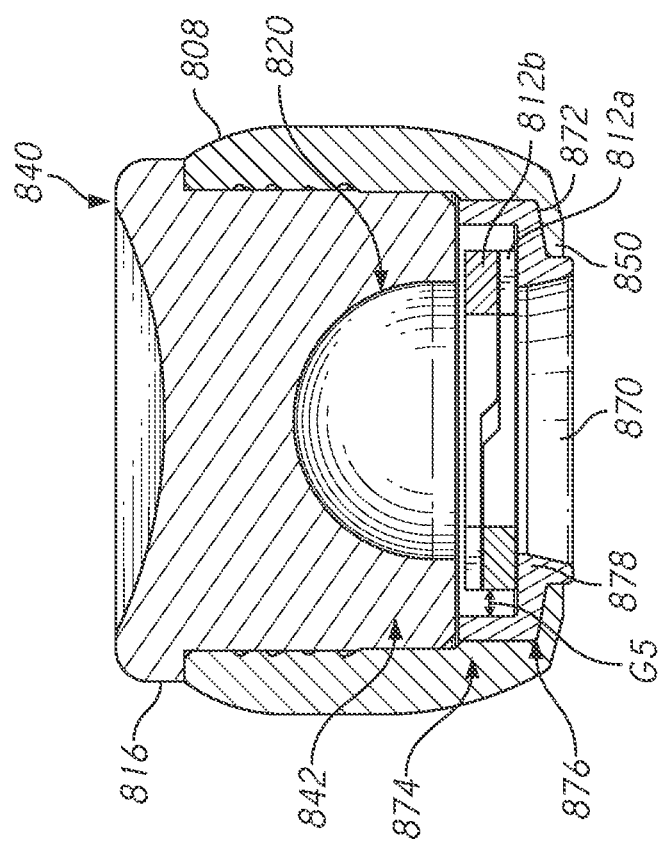
FIG. 29 illustrates a cross-section view of the articular assembly of FIG. 28.
Figure 28:
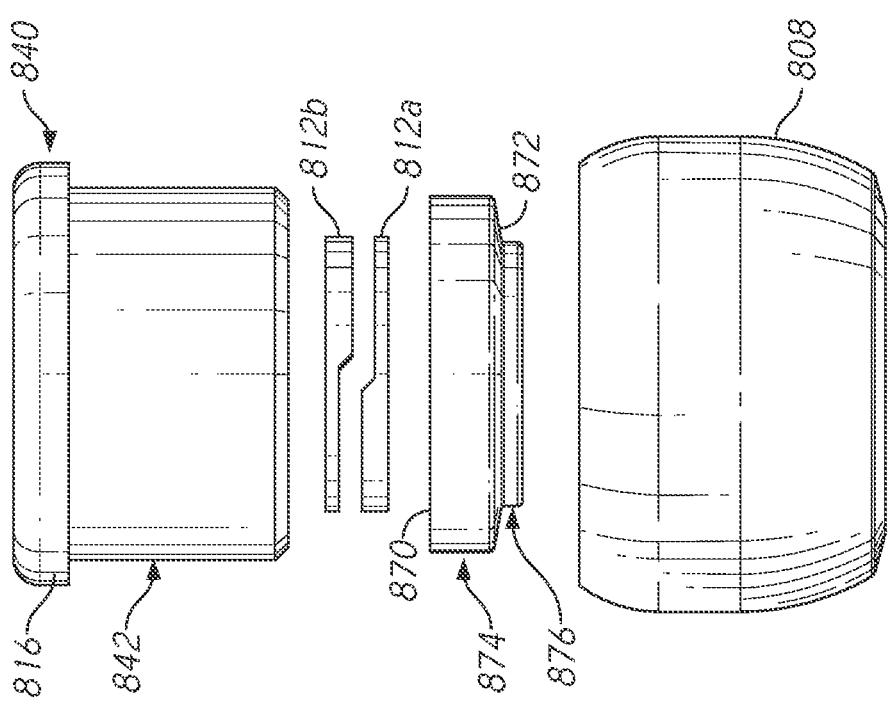
FIG. 28 illustrates an exploded view of an articular assembly of the radial head assembly of FIG. 27.

FIGS. 27 and 29 show that the trapping member 870 and the locking rings 812a, 812b is disposed within the collar 808 and the articular member 816 is partially disposed within the collar 808 when the articular assembly 804 is in the locked configuration. The articular member 816 can include a proximal portion 840 and a distal portion 842 (as shown in FIGS. 28 and 29). In some embodiments, as illustrated in FIG. 29, the distal portion 842 of an articular member 816 can be disposed against the trapping member 870 when the articular assembly 804 is in the locked configuration and prevents the trapping member 870 from moving such that a head 828 of the stem 824 can be inserted into an articular space 820 and coupled with the articular assembly 804.

In some embodiments, an interior collar surface has an inner rim 850 (as shown in FIG. 29). The inner rim 850 can be disposed adjacent to a distal end of the collar wall. The inner rim 850 can have an inner face that extends from adjacent to a distal end of the collar wall to an inner periphery. The inner periphery of the inner rim 850 can be spaced a distance radially or transversely away from the distal end of the collar wall. The distance between the distal end of the collar wall and the inner periphery of the inner rim 850 can correspond to a width of the inner rim 850. The width of the inner rim 850 can be constant. The inner rim 850 can be configured to interface with a mating surface 872 of the trapping member 870. The inner rim 850 is configured to abut the trapping member 870 when the trapping member 870 is inserted into the collar 808. In this configuration, the inner rim 850 engages the trapping member 870.

The trapping member 870 has a proximal portion 874 and a distal portion 876. The proximal portion 874 can include a mating surface 872 configured to engage the inner rim 850, as shown in FIG. 29. The mating surface 872 can have a dimension that is greater at least in part than an inner periphery of the inner rim 850. This configuration allows the trapping member 870 to be inserted until the mating surface 872 abuts the inner rim 850. The abutment of the mating surface 872 with the inner rim 850 provides a positive stop for the trapping member 870, preventing the trapping member 870 from pulling out upon application of a force away from the articular member 816. In some embodiments, the distal portion 876 of the trapping member 870 can be secured within the first collar opening with an interference fit. For example, an outer periphery of the distal portion 876 of the trapping member 870 can be larger than an inner periphery of the first collar opening such that at least some deformation of the distal portion 876 occurs upon mating the trapping member 870 with the collar 808. The material of the trapping member 870 and/or the collar 808 can enable the trapping member 870 to be deformed, e.g., compressed, upon insertion to create an interference fit.

The axial length of the trapping member 870, e.g., along the direction from the proximal portion 874 to the distal portion 876 thereof, can be greater than the axial length of the inner rim 850 such that at least a portion of the distal portion 876 of the trapping member 870 is proximal of a distal end of the collar 808 while the proximal portion 874 of the trapping member 870 is proximal of the inner rim 850. FIG. 29 shows that the distal portion 876 of the trapping member 870 can be advanced or positioned more than half way into the first collar opening.

Figure 31:
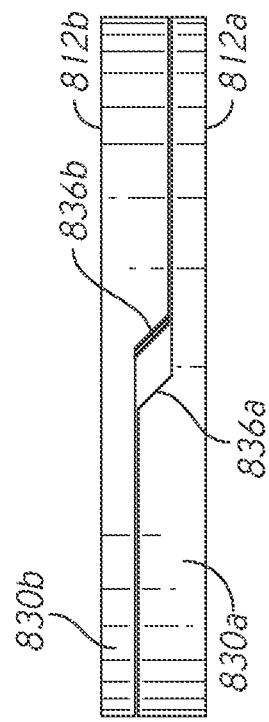
FIG. 31 illustrates a side view of the locking rings of FIG. 30.
Figure 30:
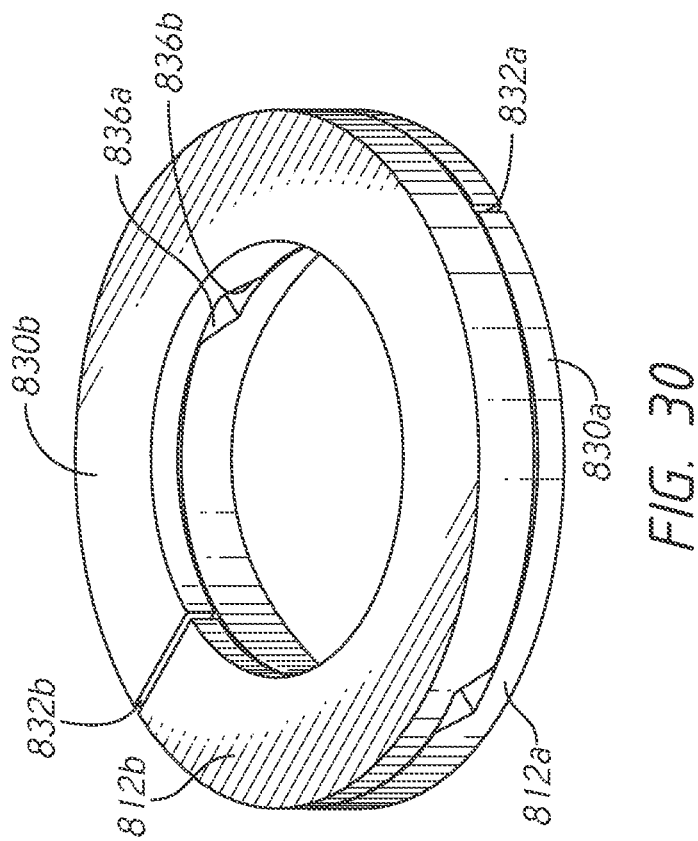
FIG. 30 illustrates a perspective view of locking rings of the radial head assembly of FIG. 27.
Figure 32:
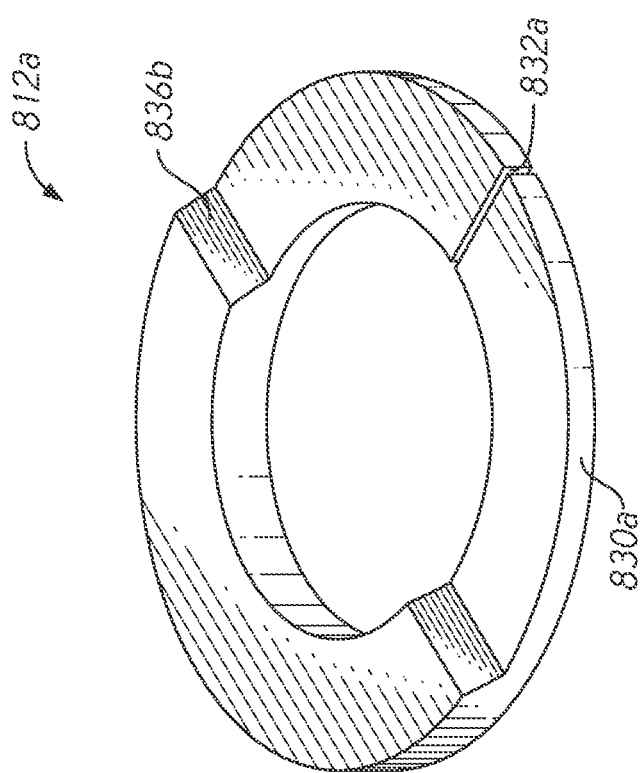
FIG. 32 illustrates a perspective view of a locking ring of the articular assembly of FIG. 27.
Figure 34:
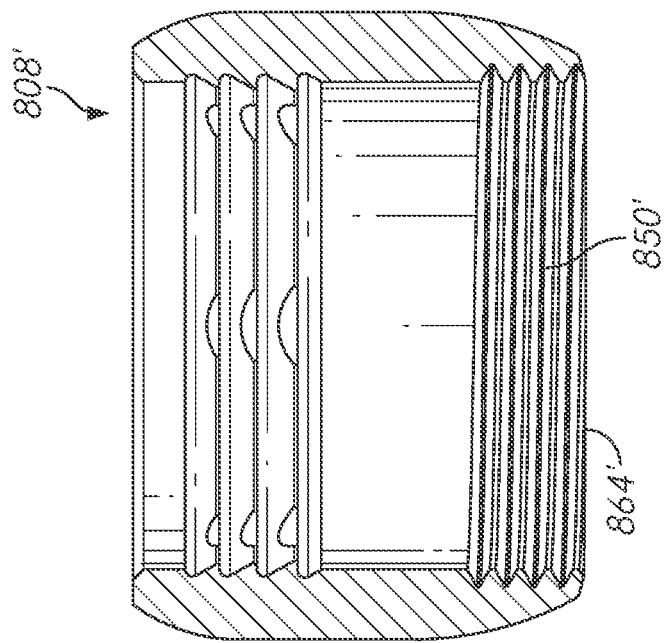
FIG. 34 illustrates a cross-section view of a collar of the articular assembly of FIG. 33.

The articular assembly 804 can comprise two or more locking rings 812a, 812b. As shown in FIGS. 30-32, each locking ring 812a, 812b has a ring wall 830a, 830b that extends between an outer periphery of the locking ring 812a, 812b and an inner periphery of the locking ring 812a, 812b. The ring wall 830a, 830b defines a ring opening. The ring wall 830a, 830b can have a slot 832a, 832b configured to permit the ring wall 830a, 830b to expand from the illustrated configuration. Elasticity of the rings 812a, 812b can enable the rings to be compressed following expansion in some embodiments.

Each of the locking ring 812a, 812b are configured to expand to allow the articular head 828 to pass through the ring opening to be disposed within the collar 808 and the articular space 820. For example, each of the slots 832a, 832b are defined between two free ends of each of the respective locking rings 812a, 812b. The two free ends can move both towards and away from each other in one embodiment.

FIGS. 27-29 illustrate that each of the locking rings 812a, 812b can be sized and shaped to be placed within the proximal portion 870 of the trapping member 870. In some embodiments, an interior trapping member surface has an inner shelf 878 disposed between the proximal portion 874 and the distal portion 876. The inner shelf 878 of the trapping member 870 can be configured to maintain the locking rings 812a, 812b within the proximal portion 870 of the trapping member 870 when the trapping member 870 and locking rings 812a, 812b are inserted into the collar 808. In some instances, the inner shelf 878 can be configured to interface with at least one of the locking rings 812a, 812b and/or to abut at least one of the locking 812a, 812b when the locking rings 812a, 812b are inserted into the trapping member 870. The abutment of the locking rings 812*a*, 812*b* with the inner shelf 878 provides a positive stop for the locking rings 812*a*, 812*b*, preventing the locking rings 812*a*, 812*b* from pulling out of the collar 808 upon application of a force away from the articular member 816.

The proximal portion 874 of the trapping member 870 can define an inner diameter of the proximal portion 874. The inner diameter can have a dimension that is greater at least in part than an outer periphery of the ring walls 830*a*, 830*b* of the locking rings 812*a*, 812*b*. This configuration can provide a range of motion, e.g., radial expansion, of the locking rings 812*a*, 812*b*. For example, this can allow the locking rings 812*a*, 812*b* to expand toward the inner surface of the collar 808 while the locking rings 812*a*, 812*b* are disposed within the collar, e.g., within the trapping member 870.

FIG. 29 shows that when the locking rings 812*a*, 812*b* are disposed within the proximal portion 874 of the trapping member 870 there is a gap G5 between the outer periphery of the locking rings 812*a*, 812*b* and an inner surface of the proximal portion 874 of the trapping member 870. The gap G5 corresponds to or provides the range of motion and/or expansion of the locking rings 812*a*, 812*b* that is permitted within the proximal portion 874 of the trapping member 870. As discussed herein, motion (e.g., expansion) of each of the locking rings 812*a*, 812*b* advantageously allows the head 828 of the stem 824 to be inserted into the collar 808 through the ring openings. The elastic nature of the rings 812*a*, 812*b*, in some embodiments, provide that the rings can return to a relaxed state with an inner periphery smaller than the width of the convex articular head 828.

With reference to FIGS. 30-32, each locking ring 812*a*, 812*b* can include at least one ring index feature 836*a*, 836*b*. The ring index feature 836*a*, 836*b* can protrude from and/or be receded within the ring wall 830*a*, 830*b* of the locking ring 812*a*, 812*b*. The ring index feature 836*a*, 836*b* can be disposed along a first surface of the locking ring 812*a*, 812*b*. The ring index feature 836*a* of the locking ring 812*a* is configured to engage the other ring index feature 836*b* of the locking ring 812*b* when the first locking ring 812*b* is placed on top of and/or aligned with the second locking ring 812*a*. Each ring index feature 836*a*, 836*b* can be configured to prevent rotation of locking ring 812*a* relative to locking ring 812*b* when the locking rings 812*a*, 812*b* are placed within the trapping member 870. The ring index features 836*a*, 836*b* can include any feature suitable to interact with the other of the ring index feature 836*a*, 836*b* to prevent rotation. For example, the ring index features 836*a*, 836*b* can comprise a peg, a barb, a screw, or other protruding structure, configured to engaged the other ring index feature 836*a*, 836*b* by an interaction fit, screw fit, snap fit, interference fit, or otherwise.

In some embodiments, as illustrated in FIGS. 30-32, the ring index features 836*a*, 836*b* is an angular outer, top, or bottom surface configured to engage with the angular outer, top or bottom surface of the other ring index feature 836*a*, 836*b*. At least one of the ring index features 836*a*, 836*b* can include an external concave structure that can receive an external convex structure of the other ring index feature 836*a*, 836*b*.

The locking rings 812*a*, 812*b* can be placed within the collar 808 and/or the trapping member 870 in a position that the slot 832*b* of the first locking ring 812*b* is not rotationally aligned with the slot 832*a* of the second locking ring 812*a*. The misalignment of the slot 832*a*, 832*b* when the locking rings 812*a*, 812*b* are inserted within the trapping member 870 can inhibit accidental disassembly and/or removal of the head 828 from the articular space 820 once inserted. In some instances, the ring index features 836*a*, 836*b* are configured such that when the first ring index feature 836*b* of the first locking ring 812*b* engages with the second ring index feature 836*a* of the second locking ring 812*a*, slot 832*b* is not rotationally aligned with slot 832*a*. For example, the ring index features 836*a*, 836*b* can be configured such that the slots 832*a*, 832*b* are located on diametrically opposite sides of the locking rings 812*a*, 812*b* when the ring index features 836*a*, 836*b* engage each other (as illustrated in FIG. 30).

FIGS. 33-36 show that, in certain embodiments, a trapping member 870' can be attached to a collar 808' through a collar connection feature 850'. The collar connection feature 850' is configured to engage the proximal portion 874' of the trapping member 870' to retain the trapping member 870' at least partially within the collar 808'. The collar connection feature 850' can include a peg, a barb, a thread, or other protruding structure configured to receive or be received by the trapping member 870' by a screw fit, snap fit, interference fit, or otherwise. In some embodiments, the collar connection feature 850' can comprise one or more threads. FIGS. 33-36 are various views of an articular assembly 804' for an elbow joint prosthesis, according to some embodiments. Unless otherwise noted, similar reference numerals in FIGS. 33-36 refer to components that are the same as or generally similar to the components in other figures discussed herein with similar features. It will be understood that the features described with reference to articular assembly 804' shown in FIGS. 33-36 can be used with any of the embodiments described and/or contemplated herein. It will also be understood that any feature, structure, material, step, or component of any embodiment described and/or illustrated herein can be used with or instead of any other feature, structure, material, step, or component of any embodiment of the articular assembly 804' shown in FIGS. 33-36.

Figure 33:
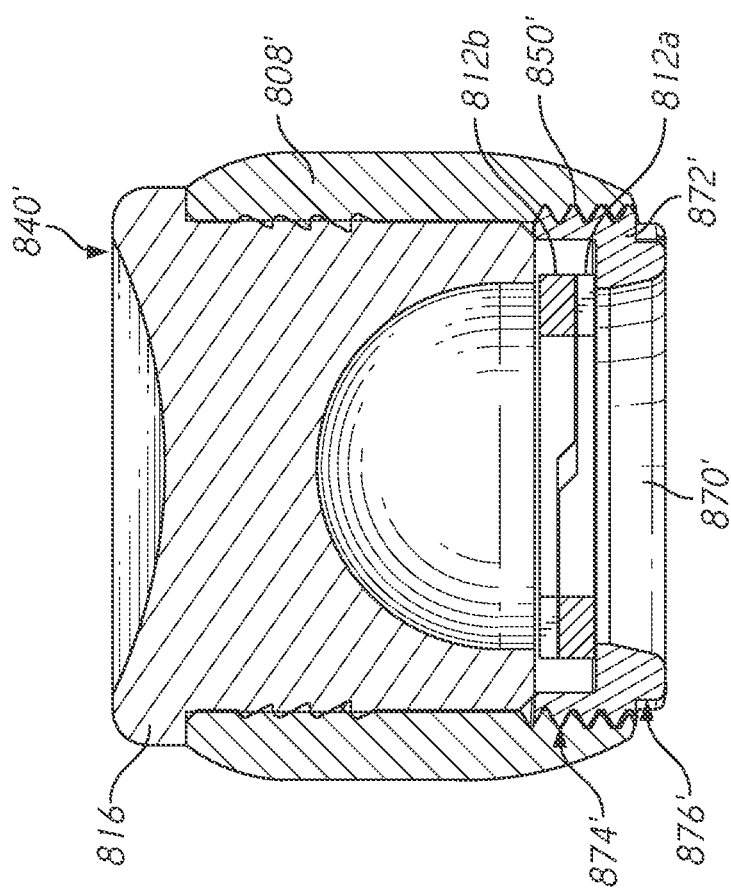
FIG. 33 illustrates a cross-section view of another embodiment of an articular assembly as disclosed herein.

In some embodiments, the one or more threads of the collar 808' can be disposed adjacent to the first opening 864' of the collar 808' and be configured to engage an outer surface of the proximal portion 874' of the trapping member 870'. For example, FIG. 33 shows that, when the trapping member 870' is engaged with the collar 808', the proximal portion 874' of the trapping may be engaged with the one or more threads of the collar 808'. In this manner, the trapping member 870' can be rotated relative to the collar 808' to facilitate engagement of the proximal portion 874' of the trapping member 870' with the one or more threads.

Rotating the trapping member 870' relative to collar 808' advantageously allows the trapping member 870' to engage with and/or translate along the one or more threads to attach the trapping member 870' to the collar 808'. The proximal portion 874' of the trapping member 870', in certain embodiments, can be engaged with the one or more threads with an interference fit. The trapping member 870', in some embodiments, can comprise a semi-rigid material capable of deformation when a force is applied. This can advantageously allow the proximal portion 874' of the trapping member 870' to temporarily and/or permanently deform when the proximal portion 874' interacts with the collar connection feature 850' (e.g., one or more threads) of the collar 850'.

Figure 36:
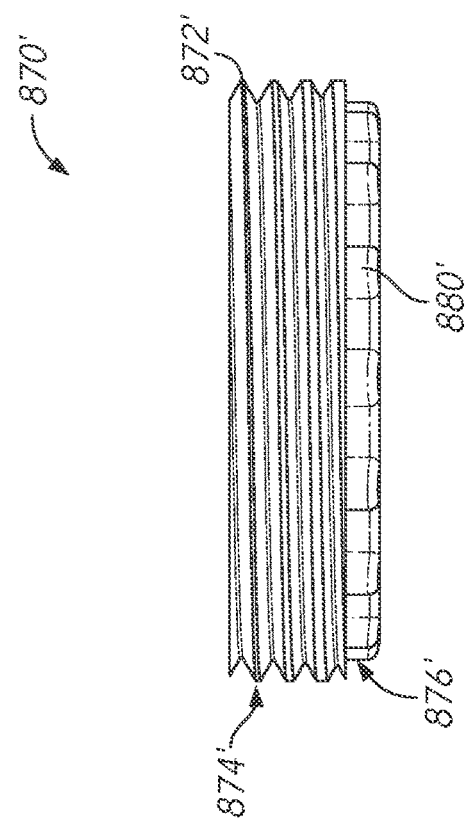
FIG. 36 illustrates a side view of the trapping member of FIG. 35.
Figure 35:
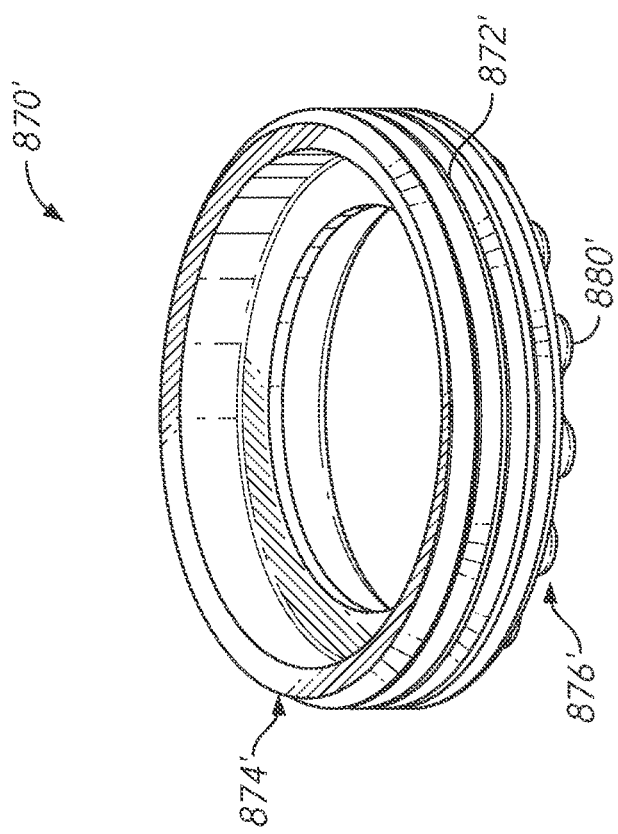
FIG. 35 illustrates a perspective view of a trapping member of the articular assembly of FIG. 33.

With reference to FIGS. 35 and 36, in some instances, the trapping member 870' may comprise corresponding threads 872' along at least a portion of the proximal portion 874' of the trapping member 870' that are configured to interact with the threads the collar 808'. For example, the trapping member 870' can be rotated clockwise or counterclockwise to engage the one or more threads of the collar 808' with corresponding threads 872' of the trapping member 870'. After engagement, the trapping member 870' can remain attached to the collar 808'.

To facilitate rotation of the trapping member 870' relative to the collar 808', in certain embodiments, at least a portion of the trapping member 870' can be configured to be gripped during attachment or screwing of the trapping member 870' onto the collar 808'. For example, in some embodiments (as illustrated in FIGS. 35 and 36), an outer surface of the distal portion 876' of the trapping member 870' can comprise a one or more gripping elements 880' configured to increase friction and/or provide one or more surfaces on which a finger, palm, or tool can exert a rotational force to facilitate attachment or removal of the trapping member 870' from the collar 808'. The gripping element 880' can include one or more grooves, scallops, notches, cavities, or other structure configured to facilitate rotation of the trapping member 870' relative to the collar 808'. FIGS. 35 and 36 show that the gripping element 880' can includes an array of ribs and/or grooves that extend inwardly into the distal portion 876' of the trapping member 870'. In one embodiment, the array of gripping elements 880' includes a plurality of such elements disposed along an outer circumference of the distal portion 876' of the trapping member 870'.

Figure 38:
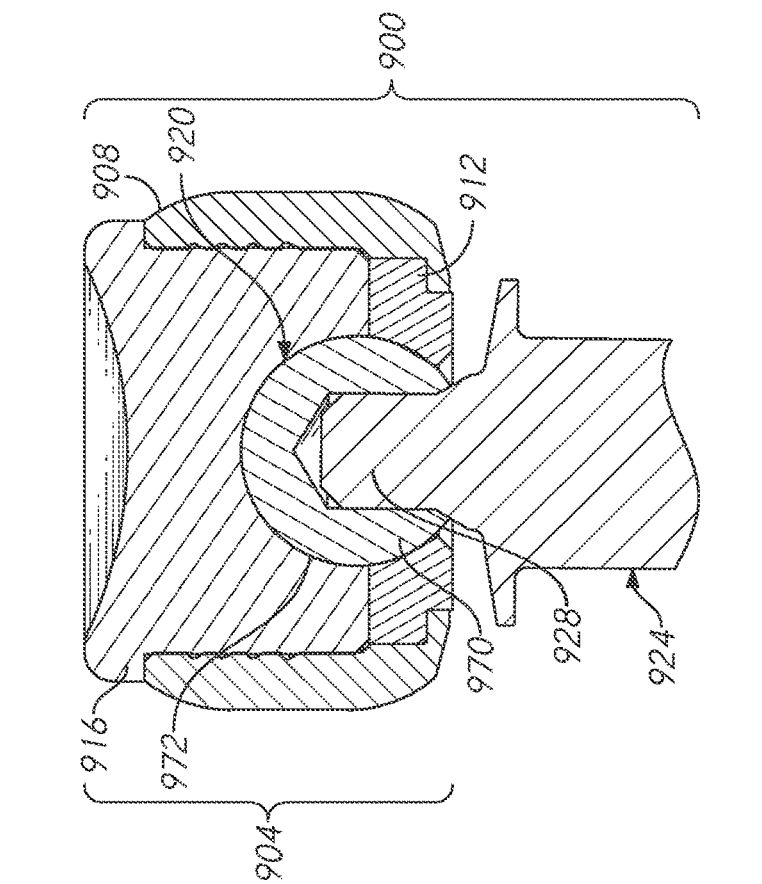
FIG. 38 illustrates a cross-section view of the radial head assembly of FIG. 37 in a locked configuration.
Figure 37:
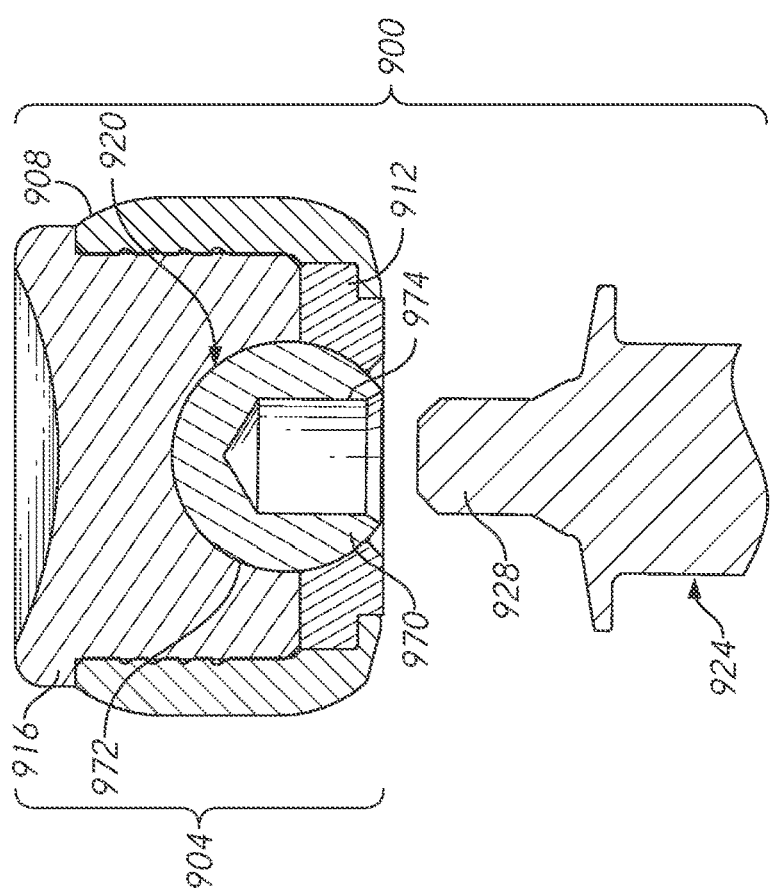
FIG. 37 illustrates a cross-section view of another embodiment of a radial head assembly as disclosed herein.

F. Radial Head Assemblies with Integrated Articular Head Component Configured to Engage Stem FIGS. 37 and 38 show that, in certain embodiments, a radial head assembly 900 may comprise an articular head component 970 that is configured to engage a distal portion 928 of a stem 924. FIGS. 37 and 38 are various views of radial head assembly 900 for an elbow joint prosthesis, according to some embodiments. The radial head assembly 900 is similar to the radial head assembly 100, except as described differently below. Accordingly, unless otherwise noted, similar reference numerals in FIGS. 37 and 38 refer to components that are the same as or generally similar to the components of assembly 100 or in other figures discussed herein with similar features. It will be understood that the features described with reference to radial head assembly 900 shown in FIGS. 37 and 38 can be used with any of the embodiments described and/or contemplated herein. It will also be understood that any feature, structure, material, step, or component of any embodiment described and/or illustrated herein can be used with or instead of any other feature, structure, material, step, or component of any embodiment of the radial head assembly 900 shown in FIGS. 37 and 38.

FIG. 37 shows a cross-section view of an embodiment of a radial head assembly 900. The radial head assembly 900 can include an articular assembly 904 and a stem 924. The articular assembly 904 includes a collar 908, an articular member 916, a locking ring 912, and an articular head component 970. In some embodiments, the proximal portion of the stem 924 can include a distal end portion 928 configured to engage with the articular head component 970 of the articular assembly 904.

FIGS. 37 and 38 show that the articular head component 970 can be disposed within an articular space 920 at least partially defined by the articular member 916, the locking ring 912, and/or the collar 908. The articular member 916 and the locking ring 912 at least partially define an articular space 920 within the collar 908 when the articular assembly 904 is fully assembled. The articular space 920 is configured to receive the articular head component 970. For instance, the articular space 920 can have a generally spherical shape to permit the articular head component 970 to pivot about the remainder of the articular assembly 904, particularly when the articular head component 970 is engaged to the distal portion 928 of the stem 924 (as shown in FIG. 38). The articular space 920 can be defined by spherical surfaces on the locking ring 912 and the articular member 816.

In some embodiments, as described herein, the articular space 920 can be defined by one or more concave surfaces of the articular member 916 and/or the locking ring 912. The one or more concave surfaces defining the articular space 920 can be configured to interface with an external mating surface 972 of the articular head component 970. The articular member 916 and/or the locking ring 912 are configured to abut the articular head component 970 when the articular head component 970 is inserted into the articular space 920. In this configuration, the articular head component 970 can be shaped to correspond to the shape of the articular space 920. The articular head component 970 can be rounded, e.g. circular shape. The mating surface 972 of the articular head component 970 can have a smooth surface or other structure or treatment adapted to facilitate rotation along at least a portion of the articular member 916.

The mating surface 972 can have a dimension (e.g. a diameter) that is less at least in part than an outer periphery of the articular space 920. This configuration allows the articular head component 970 to reside and rotate within the articular space 920. In certain embodiments, the articular head component 970 can have width greater than at least the ring opening of the locking ring 912. In this manner, the articular head component 970 would reside and/or abut against a proximal portion of the ring wall of the locking ring 912 when in the articular head component 970 is inserted within the collar 908. The abutment of the articular head component 970 with the locking ring 912 provides a positive stop for the articular head component 970, preventing the articular head component 970 from pulling out upon application of a force away from the articular member 916 and/or locking ring 912.

FIG. 37 shows that the articular head component 970 can include a concave surface 974. The concave surface 974 can be disposed on a distal face of the articular head component 970. For example, the concave surface 974 can be located between the mating surface 972 and a distal end of the articular head component 970 opposite the mating surface 972. The concave surface 974 is configured to receive at least a portion of the distal portion 928 of the stem 924 when the stem 924 is coupled with the articular assembly 904. For instance, the concave surface 974 can be shaped to correspond to the shape of the distal portion 928 such that the articular head component 970 is configured to receive and retain the distal portion 928 of the stem 924 within the articular head component 970. For instance, the concave surface can define a space having a size and shape corresponding to the size and shape of the distal portion 928 of the stem 924. The concave surface 974 can be elongated, e.g. a cylindrical and/or frusto-conical shape. The concave surface 974 can have a smooth surface or other structure or treatment adapted to facilitate attachment to at least a portion of the distal portion 928 or the stem 924. A Morse taper connection can be provided between the distal portion 928 and the concave surface 974 of the articular head component 970, in one embodiment.

In some instances, the distal portion 928 of the stem 924 can be secured within the articular head component 970 with an interference fit. For example, an outer periphery of the distal portion 928 of the stem 924 can be slightly larger than an inner periphery of the concave surface 974 of the articular head component 970 such that at least some deformation of the distal portion 928 occurs upon mating the stem 924 with the articular head component 970 and the articular assembly 904. The material of the articular head component 970 and/or the distal portion 928 of the stem 924 can enable the articular head component 970 to be deformed, e.g., compressed, upon insertion of the distal portion 928 of the stem 924 to create an interference fit. For example, in some embodiments as illustrated in FIG. 38, the distal portion 928 of the stem 924 can be disposed against and at least partially within the articular head component 970 when the articular assembly 904 is in the locked configuration to prevent the stem 924 from moving relative to the articular head component 970. As such, the distal portion 928 of the stem 924 is coupled with the articular assembly 904.

In some instances when the distal portion 928 of the stem 924 is coupled to the articular assembly 940 (e.g., when the articular assembly 904 is in the locked configuration), the articular assembly 904 is capable of bipolar articulation. Bipolar articulation can provide for rotation of the articular member 116 relative to the articular head component 970 and the stem 924 and, furthermore, articulation of the articular member 916 over a spherical portion of a humeral spool.

G. Radial Head Assemblies with Multi-Part Collar Portions

Figure 40:
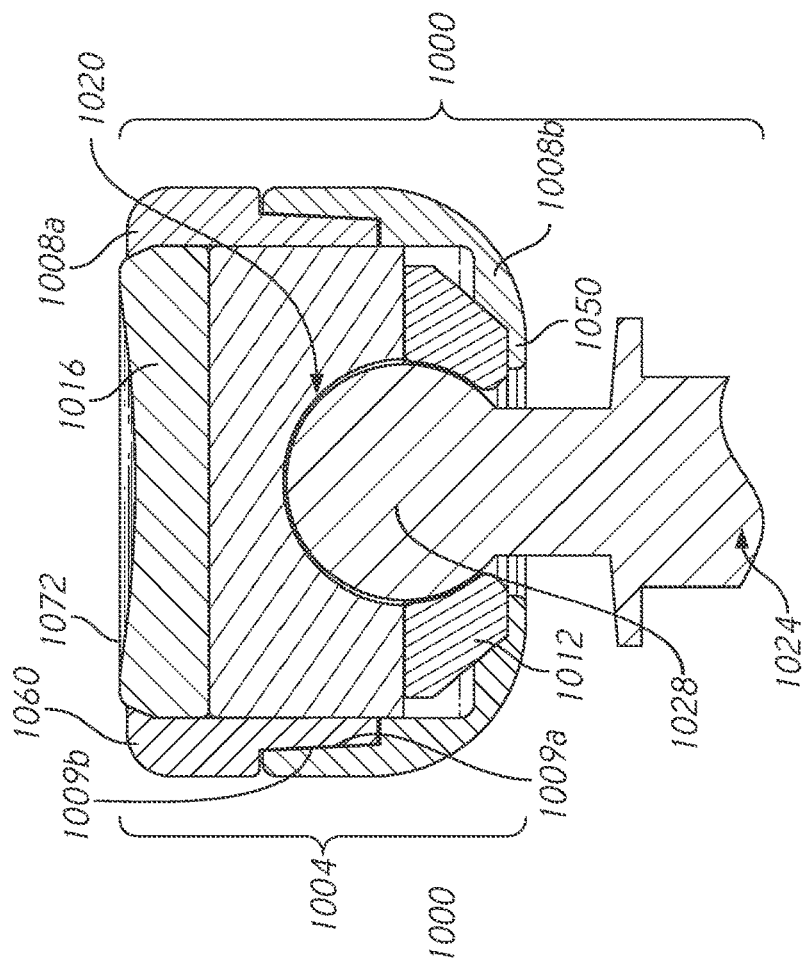
FIG. 40 illustrates a cross-section view of the radial head assembly of FIG. 39.
Figure 39:
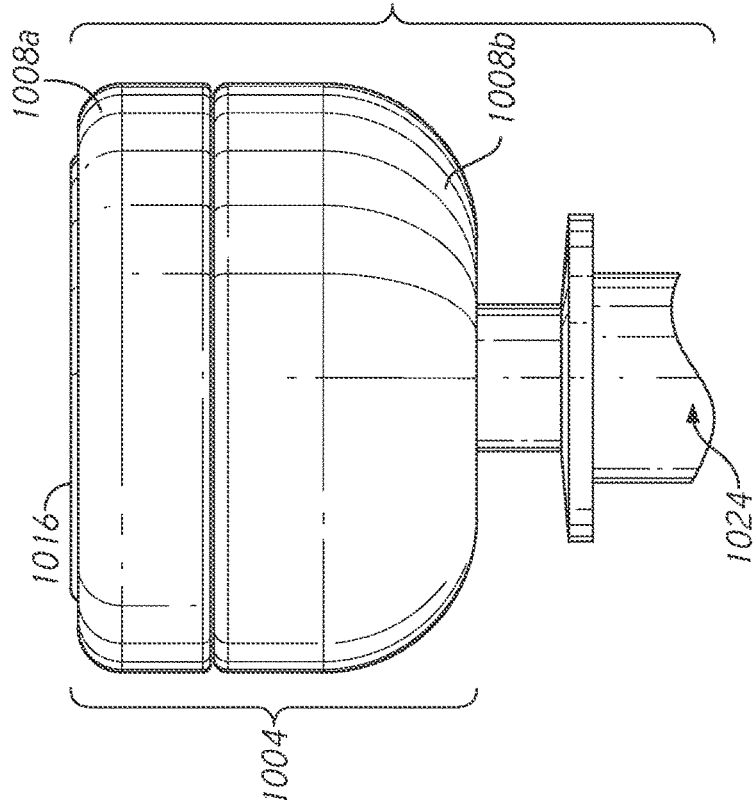
FIG. 39 illustrates a side view of another embodiment of a radial head assembly as disclosed herein.
Figure 41:
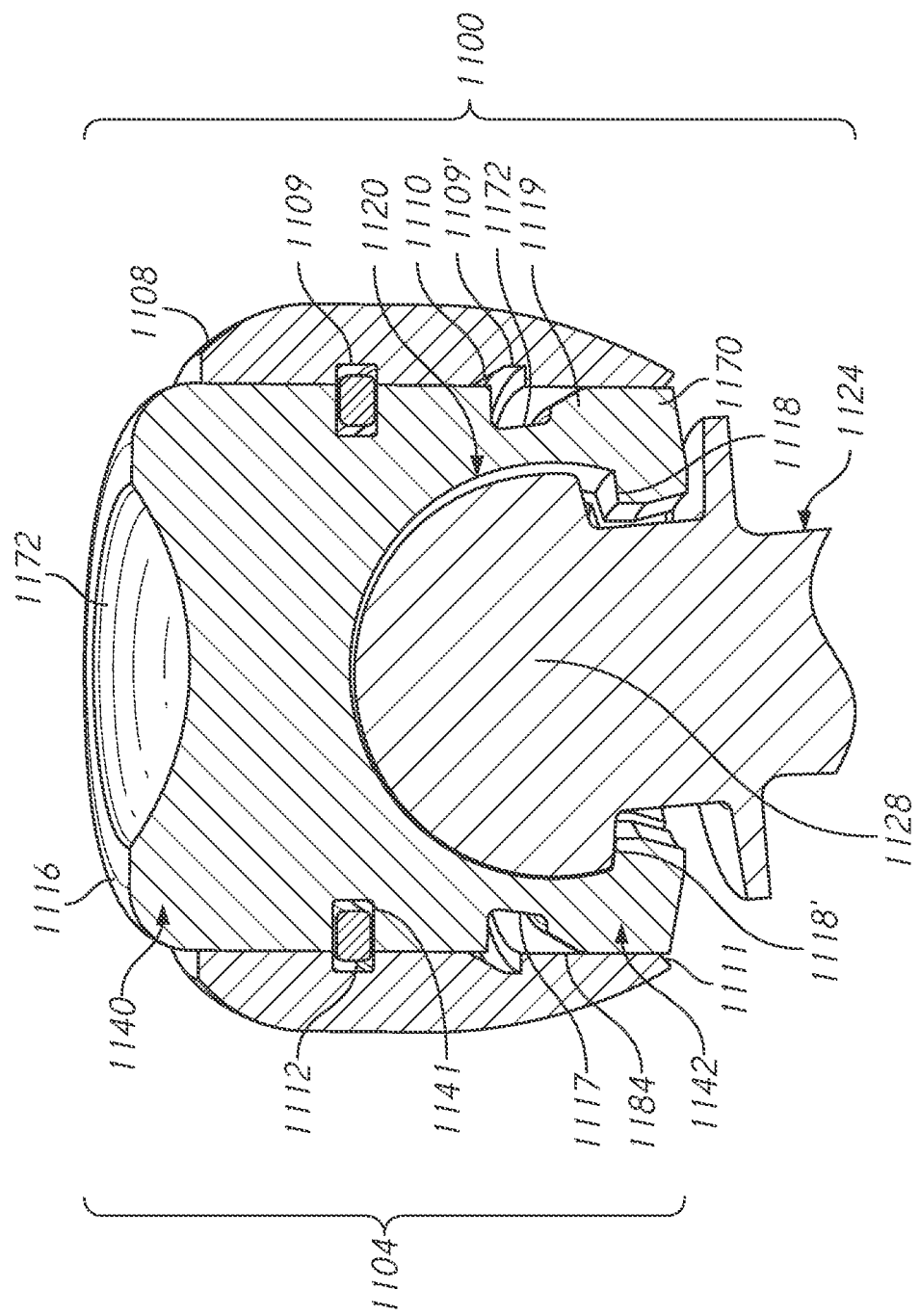
FIG. 41 illustrates a cross-section view of another embodiment of a radial head assembly as disclosed herein.

FIGS. 39 and 40 show that, in certain embodiments, a radial head assembly 1000 that had a multi-part collar, e.g., with two or more collar portions 1008a, 1008b. FIGS. 39 and 40 are various views of radial head assembly 1000 for an elbow joint prosthesis, according to some embodiments. The radial head assembly 1000 is similar to the radial head assembly 100, except as described differently below. Accordingly, unless otherwise noted, similar reference numerals in FIGS. 39 and 40 refer to components that are the same as or generally similar to the components of assembly 100 or in other figures discussed herein with similar features. It will be understood that the features described with reference to radial head assembly 1000 shown in FIGS. 39 and 40 can be used with any of the embodiments described and/or contemplated herein. It will also be understood that any feature, structure, material, step, or component of any embodiment described and/or illustrated herein can be used with or instead of any other feature, structure, material, step, or component of any embodiment of the radial head assembly 1000 shown in FIGS. 39 and 40.

FIG. 40 shows a cross-section view of an embodiment of a radial head assembly 1000. The radial head assembly 1000 can include an articular assembly 1004 and a stem 1024. The articular assembly 1004 includes an articular member 1016, a locking ring 1012, and at least two collar portions 1008a, 1008b. In some embodiments, the proximal portion of the stem 1024 can include a convex articular head 1028.

As shown in FIGS. 39 and 40, each of the first collar portion 1008a and second collar portion 1008b has a collar wall that extends between an outer periphery of each of the collar portions 1008a, 1008b and an inner periphery of each of the collar portions 1008a, 1008b. Each of the collar portions 1008a, 1008b can be configured to receive and/or maintain at least a portion of the articular member 1016, the locking ring 1012, and/or the articular head 1028 within the collar when in the locked configuration. In some instances, the second collar portion 1008b can be configured to interface with and/or to abut against at least one of the locking ring 1012 and a portion of the articular member 1016 when the locking ring 1012 and/or articular member 1016 is inserted into the second collar portion 1008b. In some instances, the first collar portion 1008a can be configured to interface with and/or to abut against the articular member 1016.

A proximal portion of the second collar member 1008b can define an inner diameter of the proximal portion having a dimension that is greater at least in part than an outer periphery of the locking ring 1012. As described herein with reference other figures with similar features, this configuration can provide a range of motion, e.g., radial expansion, of the locking ring 1012. For example, this can allow the locking ring 1012 to expand toward the inner surface of the proximal portion of the second collar member 1008b while the locking ring 1012 is disposed within the proximal portion of the second collar portion 1008b. In some instances, when the first collar portion 1008a is not fully engaged with the second collar portion 1008b, this range of motion and/or expansion of the locking ring 1012 is permitted within the proximal portion of the second collar portion 1008b. As discussed herein, motion (e.g., expansion) of each of the locking ring 1012 advantageously allows the articular head 1028 to be inserted into the second collar portion 1008b through the locking ring opening.

A secure connection is provided in at least one configuration of the articular assembly 1004 between the first collar portion 1008a and the second collar portion 1008b. The first collar portion 1008a is configured to removably engage the second collar portion 1008b to transition from an unlocked configuration to a locked configuration of the radial head assembly 1000 when the locking ring 1012, the articular member 1016, and the articular head 1028 are at least partially inserted within the first collar portion 1008a and/or the second collar portion 1008b. For example, each collar portion 1008a, 1008b can include at least one collar engagement feature 1009a, 1009b. The collar engagement features 1009a, 1009b can each protrude from and/or be receded within the collar wall of each of the respective collar portions 1008a, 1008b. For example, the collar engagement feature 1009a can be disposed along a distal portion of the first collar portion 1008a and the collar engagement feature 1009b can be disposed along a proximal portion of the second collar portion 1008b. In this manner, the collar engagement feature 1009a of the first collar portion 1009a is configured to engage the other collar engagement feature 1009b of the second collar portion 1009b when the first collar portion 1009a is placed on top of and/or aligned with the second collar portion 1009b. Each collar engagement feature 1009a, 1009b can be configured to prevent unintentional disconnection of the first collar portion 1009a from the second collar portion 1009b when the articular assembly 1004 is in the locked configuration. The collar engagement features 1009a, 1009b can include any feature suitable to interact with the other of the collar engagement features 1009a, 1009b to prevent disconnection. For example, the collar engagement features 1009a, 1009b can comprise a peg, a barb, a screw, or other protruding structure, configured to engage the other collar engagement features 1009a, 1009b by an interaction fit, screw fit, snap fit, interference fit, or otherwise. At least one of the collar engagement features 1009a, 1009b can include an external concave structure that can receive an external convex structure of the other collar engagement features 1009a, 1009b. By way of another example, each of the collar engagement features 1009a, 1009b can include one or more threads configured to engage with the one or more threads of the other collar engagement features 1009a, 1009b.

FIGS. 39 and 40 show that the articular member 1016 and the locking ring 1012 are at least partially disposed within a first collar portion 1008a and a second collar portion 1008b when the articular assembly 1004 is in the locked configuration. The first collar portion 1008a can be configured to engage the second collar portion 1008b such that the articular member 1016, the locking ring 1012, and the articular head 1028 are maintained at least partially within the first collar portion 1008a and the second collar portion 1008b. In some embodiments, as discussed in reference to other figures discussed herein, the articular member 1016 can be disposed against the locking ring 1012 and the articular head 1028 when the articular assembly 1004 is in the locked configuration. In this manner, the articular member 1016 can prevent the locking ring 1012 from moving and/or expanding such that the articular head 1028 of the stem 1024 cannot be removed from an articular space 1020 and remains coupled with the articular assembly 1004.

In some embodiments, an interior collar surface of the second collar portion 1008b has an inner lower rim 1050 (as shown in FIG. 40). The inner lower rim 1050 can be disposed adjacent to a distal end of the collar wall of the second collar portion 1008b. The inner lower rim 1050 can have an inner face that extends from adjacent to a distal end of the collar wall to an inner periphery. The inner periphery of the inner lower rim 1050 can be spaced a distance radially or transversely away from the distal end of the collar wall of the second collar portion 1008b. The inner lower rim 1050 can be configured to interface with a mating surface of the locking ring 1012. The inner lower rim 1050 is configured to abut the locking ring 1012 when the locking ring 1012 is inserted into the second collar portion 1008b and the second collar portion 1008b engages the first collar portion 1008a. In this configuration, the inner lower rim 1050 engages the locking ring 1012 to maintain the locking ring 1012 at least partially within the collar. This configuration allows the locking ring 1012 to be inserted until the mating surface of the locking ring 1012 abuts the inner lower rim 1050. The mating surface of the locking ring 1012 and/or the inner lower rim 1050 can be the same as or generally similar to the components in other the remaining figures discussed herein with similar features. For example, the abutment of the mating surface with the inner lower rim 1050 provides a positive stop for the locking ring 1012, preventing the locking ring 1012 and/or the articular head 1028 from pulling out of the second collar portion 1008b upon application of a force away from the articular member 1016. In some embodiments, a distal portion of the locking ring 1012 can be secured within a first collar opening of the second collar portion 1008b with an interference fit.

An interior collar surface of the first collar portion 1008a, in some embodiments, has an inner upper rim 1060 (as shown in FIG. 40). The inner upper rim 1060 can be disposed adjacent to a proximal end of the collar wall of the first collar portion 1008a. The inner upper rim 1060 can have an inner face that extends from adjacent to a proximal end of the collar wall to an inner periphery. The inner periphery of the inner upper rim 1060 can be spaced a distance radially or transversely away from the proximal end of the collar wall of the first collar portion 1008a. The inner upper rim 1060 can be configured to interface with a mating surface of the articular member 1016. The inner upper rim 1060 can be configured to abut the articular member 1016 when the articular member 1016 is inserted into the first collar portion 1008a and the first collar portion 1008a engages the second collar portion 1008b. In this configuration, the inner upper rim 1060 engages the articular member 1016 to maintain the articular member 1016 at least partially within the collar. The mating surface of the articular member 1016 and/or the inner upper rim 1060 can be the same as or generally similar to the components in other the remaining figures discussed herein with similar features.

The axial length of the articular member 1016, e.g., along the direction from a proximal portion to a distal portion thereof, can be greater than the axial length of the first collar portion 1008a such that at least a portion of the proximal portion of the articular member 1016 is proximal of a proximal end of the first collar portion 1008a while the articular member 1016 is placed within the first collar portion 1008a. For example, FIGS. 39 and 40 shows that the inner upper rim 1060 (e.g., a first concave surface 1072) of the articular member 1016 can extend in a proximal direction beyond the first collar portion 1008a when the articular assembly 1004 is in the locked configuration such that the first concave surface 1072 is configured to receive at least a portion of a corresponding humeral component.

The articular assembly 1004 has certain advantageous features and enables advantageous assembly methods. The collar portions 1008a, 1008b are separable. As such, the articular member 1016 can be inserted into the collar portion 1008a from the end configured to mate with the collar portion 1008b. The articular member 1016 can be advanced into the interior of the collar portion 1008a until the articular member 1016 is adjacent to or contacts the inner upper rim 1060. The inner upper rim 1060 has an inner periphery that is smaller in size than the outer periphery of articular member 1016. Thus, the inner upper rim 1060 effectively restrains and can prevent the articular member 1016 from being ejected out of the collar portion 1008a. The articular member 1016 need not be interference fit along the outer periphery thereof due to the inner upper rim 1060 containing the articular member 1016. This can make insertion by hand or with less forceful tools possible or much easier. By enabling lower force assembly the articular surfaces of the articular member 1016 can be protected. The locking ring 1012 also can more easily be assembled to the stem 1024. The locking ring 1012 can be positioned away from the inner lower rim 1050 where expansion of the ring is less or un-constrained. In this position, the head 1028 can be advanced through the locking ring 1012 with less force. This again protects the convex articular surface of the head 1028. Thereafter, the collar portions 1008a, 1008b can be brought together and thereafter secured, as discussed above.

H. Radial Head Assemblies with Expandable Articular Member Locking Mechanism

FIG. 41 shows that, in certain embodiments, a radial head assembly 1100 may comprise an articular member 1116 including one or more trapping members 1170 configured to receive an articular head 1128. The radial head assembly 1100 is similar to the radial head assembly 100, except as described differently below. Accordingly, unless otherwise noted, similar reference numerals in FIG. 41 refer to components that are the same as or generally similar to the components of assembly 100 or in other figures discussed herein with similar features. It will be understood that the features described with reference to radial head assembly 1100 shown in FIG. 41 can be used with any of the embodiments described and/or contemplated herein. It will also be understood that any feature, structure, material, step, or component of any embodiment described and/or illustrated herein can be used with or instead of any other feature, structure, material, step, or component of any embodiment of the radial head assembly 1100 shown in FIG. 41.

FIG. 41 shows a cross-section view of an embodiment of a radial head assembly 1100. The radial head assembly 1100 can include an articular assembly 1104 and a stem 1124. The articular assembly 1104 includes an articular member 1116, a locking ring 1112, and a collar 1108. The articular member 1116 has an unlocked configuration and a locked configuration. For example, the articular member 1116 is configured to move axially relative to the collar 1108 between an unlocked position and a locked position. For example, the articular member 1116 can be located in a distal position relative to the collar 1108 when in an unlocked position and/or a pre-assembled configuration. In this context, distal is toward an end of the collar 1108 where the stem is located. In the unlocked position and/or the pre-assembled configuration, one or more trapping members 1170 of the articular member 1116 are outside of the collar 1108. When outside the collar, the trapping members 1170 can be deflected or can expand away from a central axis of the assembly 1100. When expanded or deflected, the articular member 1116 can receive at least a portion of the stem 1124. By way of another example, the articular member 1116 can move in a proximal direction from the unlocked configuration to transition to a locked configuration such that a collar engagement feature 1184 interacts with the one or more trapping members 1170 to inhibit deflection or expansion of the articular member 1116 which could permit disconnection of the articular member 116 from the stem 1124. In some embodiments, the proximal portion of the stem 1124 can include a convex articular head 1128. In the illustrated embodiment, the convex articular head 1128 is semicircular.

The articular member 1116 can have a proximal portion 1140 and a distal portion 1142. The distal portion 1142 is configured to couple with a convex articular head 1128 of a stem 1124 that is coupled with a first bone. The articular member 1116 can engage with a locking ring 1112 configured to interact with a collar 1108. The proximal portion 1140 can include a first concave surface 1072 configured to receive at least a portion of a corresponding humeral component.

The proximal portion 1140, in some instances, can include an articular member outer surface having an inner channel 1141 in the proximal portion 1140 of the articular member 1116. The inner channel 1141 can have an inner face that extends from the articular member outer surface to an inner periphery. The inner periphery of the inner channel 1141 can be spaced a distance radially or transversely away from the articular member outer surface. The distance between the outer surface and the inner periphery of the inner channel 1141 can correspond to a width of the inner channel 1141. The width of the inner channel 1141 can be constant. The inner channel 1141 can be configured to interface with at least a portion of the locking ring 1112. The inner channel 1141 is configured to maintain the locking ring 1112 at least partially within the inner channel 1141 as the articular member 1116 moves axially relative to the collar 1108 between the unlocked configuration and the locked configuration.

The locking ring 1112 can have a ring wall defining a ring opening and extending along at least a portion of the inner channel 1141 of the articular member 1116. The ring wall can have a slot configured to permit the ring wall to expand between a compressed configuration and an expanded configuration (as shown in FIG. 41). The elasticity of the locking ring can enable the ring to be compressed following expansion in some embodiments. The locking ring 1112 can have a dimension (e.g., a resting diameter) that is greater at least in part than a width of the inner channel 1141. For example, the radial width of the locking ring 1112 when in a resting state can be greater than the radial width of the inner channel 1141 such that at least a portion of the locking ring 1112 extends radially beyond the outer surface of the articular member 1116 when in the expanded configuration. For example, FIG. 41 shows that the locking ring 1112 can extend beyond an outer surface of the articular member 1116 when the locking ring 1112 axially aligns with an interior trapping surface 1109 and/or transition surface 1110 of the collar 1108, as described in further detail herein. This configuration allows the locking ring 1112 to be inserted into the inner channel 1141 of the articular member 1116 and compressed between an inner surface of a collar wall and the inner periphery of the inner channel 1141 as the articular member 1116 is at least partially placed within the collar 1108 until the locking ring 1112 axially aligns against the interior trapping surface 1109 of the collar 1108. As the locking ring 1112 axially aligns with the interior trapping surface 1109, the locking ring 1112 can be configured to expand and abut against at least part of the interior trapping surface 1109 of the collar 1108 and the inner channel 1141 of the articular member 1116. The abutment of the locking ring 1112 with the interior trapping surface 1109 and the inner channel 1141 provides a positive stop for the articular member 1116, preventing the articular member 1116 from further axial movement relative to the collar 1108 and transitioning the articular assembly 1104 into a locked configuration.

In some embodiments, the articular assembly 1104 can be positioned in a pre-assembled configuration prior to implantation of the articular assembly 1104 on the articular head 1128. The articular assembly 1104 can be partially assembled by placing the locking ring 1112 and the articular member 1116 at least partially within the collar 1108. The locking ring 1112 may be placed along the inner channel 1141 of the articular member 1116 and may be inserted into the collar 1108 through a distal opening of the collar 1108. The locking ring 1112, in some instances, can be inserted into the collar 1108 upon circumferential compression of the locking ring 1112. A distal end surface 1111 of the collar 1108 may be tapered. The taper angle and length of the distal end surface 1111 can be configured to facilitate insertion and/or compression of the locking ring 1112 as the locking ring 1112 and the articular member 1116 are inserted into the collar 1108. The articular member 1116 and the locking ring 1112 may be inserted into the collar 1108 until the locking ring 1112 axially aligns with retention portion 1009'. The retention portion 1009' can include a portion of an inner wall of the collar 1108. The inner wall can include a transition surface 1110. The transition surface 1110 can provide a portion of the collar 1108 that can cause the locking ring 1112 to automatically compress upon relative movement between the collar 1104 and the articular member 1116 as discussed below.

When the locking ring 1112 axially aligns with the retention portion 1009', the locking ring 1112 can be configured to expand and abut against at least part of the retention portion 1009' of the collar 1108. The abutment of the locking ring 1112 with the retention portion 1009' and the inner channel 1141 provides a temporary positive stop for the articular member 1116, preventing the articular member 1116 from further axial movement relative to the collar 1108 until further force is applied to the articular member 1116. As the locking ring 1112 abuts the retention portion 1009', the articular assembly 1104 is in the pre-assembled configuration and can be configured for coupling with an articular head 1128 of a stem 1124. While in the pre-assembled configuration, the locking ring 1112 is engaged with the collar 1108 along the retention portion 1009' and may not be confined or constrained by an interior collar surface. The transition surface 1110 can be an angled or tapered surface disposed between located between the retention portion 1009' and the trapping surface 1109. The transition surface 1110 can be configured to facilitate compression of the locking ring 1112 such that the locking ring 1112 may then be advanced within the collar 1108 to a position where the locking ring 1112 is axially aligned with the interior trapping surface 1109 when the articular member 1116 receives the articular head 11128 and transitions to a locked configuration. For example, the transition surface 1110 can comprise a tapered surface disposed about the periphery of the interior of the collar proximal of the retention portion 1109'. The taper angle and length of the proximal portion of the transition surface 1110 can be configured to facilitate insertion and/or compression of the locking ring 1112 as the locking ring 1112 and the articular member 1116 transition from the pre-assembled configuration to the locked configuration. In some instances, a compression sleeve tool or any other suitable tool can be utilized to compress the locking ring 1112 prior to and/or as the locking ring 1112 and the articular member 1116 are inserted into the collar 1108. In some embodiments, a distal portion of the retention portion 1109' between the transition surface 1110 and the distal end surface 1111 can comprise a protrusion from the collar inner surface configured to inhibit movement of the locking ring 1112 and the articular member 1116 in a distal direction relative to the collar 1108 when the articular assembly 1104 is in a pre-assembled configuration.

The collar 1108 has a collar wall that defines a proximal collar opening, a distal collar opening, and an interior trapping surface 1109 proximate to the proximal collar opening. The collar wall, in some instances, can include a generally uniform inner diameter along the collar wall. For example, an inner diameter of the collar wall may not decrease as the collar wall approaches a distal opening of the collar 1108. The interior trapping surface 1109 can have an inner face that extends from a collar inner wall to an outer periphery. The outer periphery of the interior trapping surface 1109 can be spaced a distance radially or transversely away from the collar inner wall. The distance between the inner wall and the outer periphery of the interior trapping surface 1109 can be configured to interface with at least a portion of the locking ring 1112 when the articular assembly 1104 transitions to a locked configuration. As described herein, in some instances, when the locking ring 1112 axially aligns with the interior trapping surface 1109, the locking ring 1112 is configured to radially expand from the inner channel 1141 of the articular member 1116 such that the locking ring 1112 is disposed in the interior trapping surface 1109 of the collar 1108 and the inner channel 1141 of the articular member 1116. In this manner, the articular assembly 1104 is in the locked configuration and the articular member 1116 is unable to move axially relative to the collar 1108 due to the locking ring 1112.

The distal portion 1142 of the articular member 1116 may comprise one or more trapping members 1170. As described in further detail herein, the one or more trapping members 1170 may be at least partially disposed within the collar 1108 when the articular assembly 1104 is in the locked configuration. The one or more trapping members 1170 can be configured to receive at least a portion of the articular head 1128 of the stem when the articular member 1116 is coupled with the stem 1124 in the unlocked configuration. The one or more trapping members 1170 may at least partially define an articular space 1120 that can be shaped to correspond to the shape of the articular head 1128.

As discussed in reference to other figures discussed herein with similar features, the articular space 1120 and/or the articular member 1116 may be sized and shaped to permit bipolar articulation of the articular assembly 1104 when the articular head 1128 is inserted within the articular space 1120, e.g., when the articular assembly 1104 is in the locked configuration. Bipolar articulation can provide for rotation of the articular member 1116 relative to the articular head 1128. For example, the articular member 1116 may engage the articular head with one or more articular engagement features 1118 of the one or more trapping members 1170. The articular engagement features 1118 can interact with the articular head 1128 such that the articular engagement features 1118 inhibits removal of the articular head 1128 form the articular space 1120 while still permitting a degree of rotational movement of the articular head 1128 relative to the articular assembly 1104 when in the locked configuration. For example, in one extent of the range of motion (as shown in FIG. 41), the articular head 1128 may contact a second articular engagement feature 1118' while a gap exists between the articular head 1128 and the articular engagement feature 1118.

Each of the one or more trapping members 1170 are configured to expand to allow the articular head 1128 to pass through an opening defined by the one or more trapping members 1170 in a distal end of the articular member 1016. In this manner, the articular head 1128 can be disposed within the articular member 1116 and the articular space 1120. For example, one or more slots 1117 in the articular member 1116 may exist and be defined along the one or more trapping members 1170. The one or more slots 1117 of the articular member 1116 configured to allow the one or more trapping members 1170 to move both towards and away from each other. For example, in one embodiment, the one or more slots 1117 can permit deflection, expansion, and/or compression of the one or more trapping members 1170 and the opening at the distal end of the articular member 1016. The elastic or deflectable nature of the one or more trapping members 1170, in some embodiments, provide that the one or more trapping members 1170 can return to a relaxed state with or can be compressed or deflected to have an inner periphery smaller than the width of the articular head 1128.

FIG. 41 illustrates that each of the one or more trapping members 1170 can be configured to be placed at least partially within the distal portion of the collar 1108 when in the locked configuration. The articular member 1116 can include a trapping member transition surface 1119 that can facilitate transition of the articular member 1116 from the unlocked configuration towards the locked configuration as the articular member 1116 is inserted within the collar 1108. The trapping member transition surface 1119 can be an angled or tapered surface disposed at a location distal to the one or more slots 1117. The trapping member transition surface 1119 can be configured to facilitate compression of the one or more trapping members 1170 such that the one or more trapping members 1170 may then be advanced within the collar 1108 when the articular member 1116 transitions to a locked configuration. For example, the trapping member transition surface 1119 can comprise a tapered surface disposed about the periphery of the outside surface of the articular member 1116 distal to the one or more slots 1117. The taper angle and length of the proximal portion of the trapping member transition surface 1119 can be configured to facilitate insertion and/or compression of the one or more trapping members 1170 as the articular member 1116 transition from the pre-assembled configuration to the locked configuration.

In some embodiments, a collar inner surface has collar engagement feature 1184 disposed at least partially along the inner collar surface. The collar engagement feature 1184 of the collar 1108 can be configured to maintain the one or more trapping members 1170 within the distal portion of the collar 1108 in a compressed state when the articular member 1116 and the one or more trapping members 1170 are inserted into the collar 1108 and are placed in the locked configuration. The collar engagement feature 1184, in some instances, can interact with the one or more trapping members 1170 to prevent the one or more trapping members 1170 from expanding to inhibit removal of the articular head 1128 from the articular space 1120 when the articular assembly 1104 is in the locked configuration. In some instances, the collar engagement feature 1184 can be configured to interface with a mating surface 1172 of the one or more trapping members 1170 and/or to abut at least one of the one or more trapping members 1170 when the one or more trapping members 1170 are inserted into the collar 1108. The abutment of the one or more trapping members 1170 and/or the mating surface 1172 with the collar engagement feature 1184 provides a positive stop for the one or more trapping members 1170, thereby preventing the one or more trapping members 1170 from expanding and the removal of the articular head 1128 from the articular space 1120.

The collar engagement feature 1184 can define an inner diameter having a dimension that is less than at least in part than an outer periphery of the mating surface 1172 when the one or more trapping members 1170 are in the expanded configuration. FIG. 41 shows that when the mating surface 1172 is disposed against the collar engagement feature 1184 of the collar 1108, the collar engagement feature 1108 abuts directly against the one or more trapping members 1170 and inhibits motion and/or expansion of the one or more trapping members 1170. As discussed herein, preventing the motion (e.g., expansion) of one or more trapping members 1170 advantageously inhibits the removal of the articular head 1128 of the stem 1124 from the articular space 1120 through the distal opening of the articular member 1116.

The collar engagement feature 1184 can include a protrusion from the inner wall of the collar 1108. For example, the collar engagement feature 1184 is configured to engage the mating surface 1172 of the one or more trapping members 1170 when the collar engagement feature 1184 is placed adjacent to and/or aligned with the mating surface 1172. The collar engagement feature 1184 can be configured to prevent radial expansion of the one or more trapping members 1170 when the mating surface 1172 interacts with the collar engagement feature 1184. The collar engagement feature 1184 can include any feature suitable to interact with the mating surface 1172 to prevent expansion. For example, collar engagement feature 1184 can comprise a peg, a barb, a screw, or other protruding structure, configured to engaged the mating surface 1172 by an interaction fit, screw fit, snap fit, interference fit, or otherwise. In some embodiments, as illustrated in FIG. 41, the collar engagement feature 1184 can include an external convex structure that can interact with an external concave structure of the mating surface 1172.

III. Implantation Methods for Enhanced Elbow Joint Assemblies

Referring back to the radial head assembly 100 shown in FIGS. 2-15, in use, the stem 124 can be implanted in the radius before the articular assembly 104 is positioned on the stem 124. The stem 124 is secured to the articular assembly 104 by inserting the articular head 128 of the stem 124 into the articular space 120 of the articular assembly 104. In some cases, the radial head assembly 100 may need to be replaced. The stem 124 can remain coupled to the radius while the articular assembly 104 is replaced. The surgeon may provide a new articular assembly 104 or an articular assembly 104 of a different configuration. FIGS. 20A and 20B show aspects of surgical methods related to the implantation of apparatuses disclosed herein. FIG. 21 shows aspects of surgical methods related to the removal of apparatuses disclosed herein.

A. Methods of Implanting an Articulation Assembly on an Articular Head of a Stem FIGS. 2, 20A, 20B, and 23A-23E show various surgical methods for implanting an elbow joint prosthesis. In the methods, a distal portion of a stem 124 is attached to a first bone with the articular head 128 extending from a proximal end 130 of the stem 124. The joint may be separated or dislocated during the procedure, but the position of the head 128 will be in the joint space between the first bone and a second bone after the procedure. For example, the stem 124 may be attached to a radius bone adjacent to an elbow joint and the articular head 128 may be positioned between the radius bone and a humerus upon completion of the procedure. In some embodiments, the stem 124 includes an annular member 132. The annular member 132 can act as a positive stop upon insertion of the distal portion of the stem 124 into the first bone. The stem 124 may be inserted until the annular member 132 is at a position proximal to the first bone, as shown in FIG. 20A. The annular member 132 can provide protection against impingement on the radius bone by the articular assembly 104.

With reference to FIGS. 2, 20A, and 20B, the articular assembly 104 can be fully assembled prior to implantation of the articular assembly 104 on the articular head 128, as shown in FIG. 20A. The articular assembly 104 can be assembled by placing the locking ring 112 and the articular member 116 at least partially within the collar 108. The locking ring 112 may be inserted into the collar 108 through the second collar opening 168 with little to no compression. The locking ring 112 may be inserted into the collar 108 through the first collar opening 164 upon circumferential compression. The locking ring 112 can be disposed within the collar 108 in the free configuration, as shown in FIG. 20A. While in the free configuration, the locking ring 112 is disengaged with the collar 108 and may not be confined or constrained by the interior collar surface 172. The locking ring 112 is permitted to undergo a range of axial and/or radial motion within the collar 108, as previously discussed. FIG. 20A shows a gap G8 disposed between the locking ring 112 and the interior collar surface 172. Gap G8 permits the locking ring 112 to expand circumferentially or transversely within the collar 108 without confinement by the interior collar surface 172. The locking ring 112 may be placed within the collar 108 in a position that the slot 232 is rotationally aligned with the aperture 180. The locking ring 112 may then be advanced within the collar 108 to a position where the slot 232 is longitudinally aligned with the aperture 180 to facilitate a removal of the locking ring 112, as described herein.

During assembly of the articular assembly 104, the articular member 116 is at least partially inserted within the collar 108. The projection 264 can be advanced into the collar 108 with the outer rim 268 acting as a positive stop upon insertion of the articular member 116 into the collar 108. The proximal portion 140 can be exposed outside a proximal portion 144 of the collar 108, thus leaving the first concave surface 272 located proximal to the second collar opening 168. The projection 264 can be secured within the collar 108 through interaction with at least one of the collar connection feature 184 and the anti-rotational feature 188 (as shown in FIGS. 7 and 8). As discussed previously, the distal end surface 280 can be disposed well short of the distal end of the collar 108, which provides the locking ring 112 with a range of axial and radial motion within the interior of the collar 108.

The collar 108, locking ring 112, and the articular member 116 define an articular space 120 within the interior of the articular assembly 104 when the articular assembly 104 is fully assembled. To insert the articular head 128 into the articular space 120, the first collar opening 164 of the articular assembly 104 is placed on the articular head 128, as shown in FIG. 20A. The articular head 128 interacts with the distal portion 240 of the locking ring 112. The interaction with the articular head 128 may proximally advance the locking ring 112 within the collar 108 to a position abutting a distal end of the articular member 116. A force F4 in the direction of a longitudinal axis of the articular head 128 can be applied to the articular assembly 104. The force F4 may cause the articular assembly 104 to engage the articular head 128 and compress the locking ring 112 between the articular member 116 and the articular head 128. As force F4 is applied the articular head 128 may be advanced to within the ring opening 224 and may then cause the locking ring 112 to expand. The slot 232 permits the two free ends 233 to move away from each other. As such, the inner diameter D of the locking ring 112 is increased within the space provided by gap G8. The expansion of the locking ring 112 permits the articular head 128 to be advanced through the increased diameter D of the locking ring 112. Once inserted through the locking ring 112, the articular head 128 is disposed in the articular space 120 between the locking ring 112 and the second concave surface 276. The locking ring 112 is disposed between the articular head 128 and the angular portion 176 of the interior collar surface 172.

FIG. 20B illustrates a method for placing the locking ring 112 in the locked configuration. When the articular head 128 is disposed within the articular space 120, a distraction force F8 can be applied between the stem 124 and the articular assembly 104 to position the radial head assembly 100 in the locked configuration. A distraction force F8, and a corresponding equal and opposite reactionary force F8', can be applied to the radial head assembly 100. The distraction force F8 causes the proximal portion 238 of the locking ring 112 (as shown in FIG. 11) to interface with the articular head 128. As the distraction force F8 is applied, the articular head 128 may distally advance the locking ring 112 to a position adjacent to the first collar opening 164. The angular outer surface 228 of the locking ring 112 can engage the angular portion 176 of the interior collar surface 172. Movement of the locking ring 112 distally decreases the gap G8 between locking ring 112 and the interior collar surface 172. As the gap G8 decreases, the ability of the locking ring 112 to expand decreases. This prevents the stem 124 from being inadvertently dislodged from the articular assembly 104.

In some embodiments, a continued application of the distraction force F8 to the articular head 128 causes a distal portion 150 of the locking ring 112 to enter the locked configuration disposed distal to the first collar opening 164. The at least one ring connection feature 236 can engage the collar wall 160 to retain the locking ring 112 in the collar 108. As described previously, the ring connection feature 236 can include a groove or flange that can be configured to inhibit disengagement of the locking ring 112 from the collar 108. The collar wall 160 can confine the locking ring 112 and inhibit expansion of the locking ring 112 when in the locked configuration. The locked configuration prevents the articular head 128 from passing through the locking ring 112 and disengaging the articular assembly 104. The locked configuration still allows bipolar articulation, however, providing a great degree of movement to provide natural or near natural joint motion in a prosthesis employing the radial head assembly 100.

FIG. 20C shows another method of confirming the connection between the circumferential groove 237 of the locking ring 112 and the distal portion 146 of the collar 108. An actuator 600 can be provided that has a distal end 604 that is configured to seat the locking ring 112 around the collar 108. The distal end can have a U-shaped configuration that has two opposing tines that can be inserted between the annular member 132 and the distal portion of the locking ring 112. Once inserted into the space between the annular member 132 and the locking ring 112 further insertion and/or rotation about the stem 124 can engage the circumferential groove 237 with the distal portion 146 of the collar 108. The proximal end 608 for the actuator 600 can have another U-shaped portion with tines configured to be similarly inserted. The depth of the tines (as measured from the underside to the upper side of the actuator 600) is greater at the proximal end 608 than at the distal end 604. The tines at the proximal end 608 are suitable for longer stems where the distance from the annular member 132 to the locking ring 112 is greater. The actuator 600 can be configured as an elongate bar member. In a span 412 between the distal and proximal ends 604, 608 gripping portions 616 can be formed on an underside and gripping portions 620 can be formed on an upper side. The gripping portions 616, 620 aid the surgeon in grasping and actuating the actuator 600.

Although this method is described in the context of the radial head assembly 100 shown in FIGS. 2-15, a similar method can be used to implant the radial head assemblies 400, 480 shown in FIGS. 17-19.

FIGS. 23A-23E are various views of surgical method for implanting an elbow joint prosthesis, according to some embodiments. In particular, FIGS. 23A-23E illustrate a surgical method for implanting an articular assembly 104' including articular member 116' discussed herein with reference to FIGS. 4A and 4B. Unless otherwise noted, identical reference numerals in FIGS. 23A-23E refer to components that are the same as or generally similar to the components other figures discussed herein. It will be understood that the features described with reference to articular member 116' shown in FIGS. 23A-23E can be used with any of the embodiments described and/or contemplated herein. It will also be understood that any feature, structure, material, step, or component of any embodiment described and/or illustrated herein can be used with or instead of any other feature, structure, material, step, or component of any embodiment of articular member 116' shown in FIGS. 23A-23E.

Figure 23A:
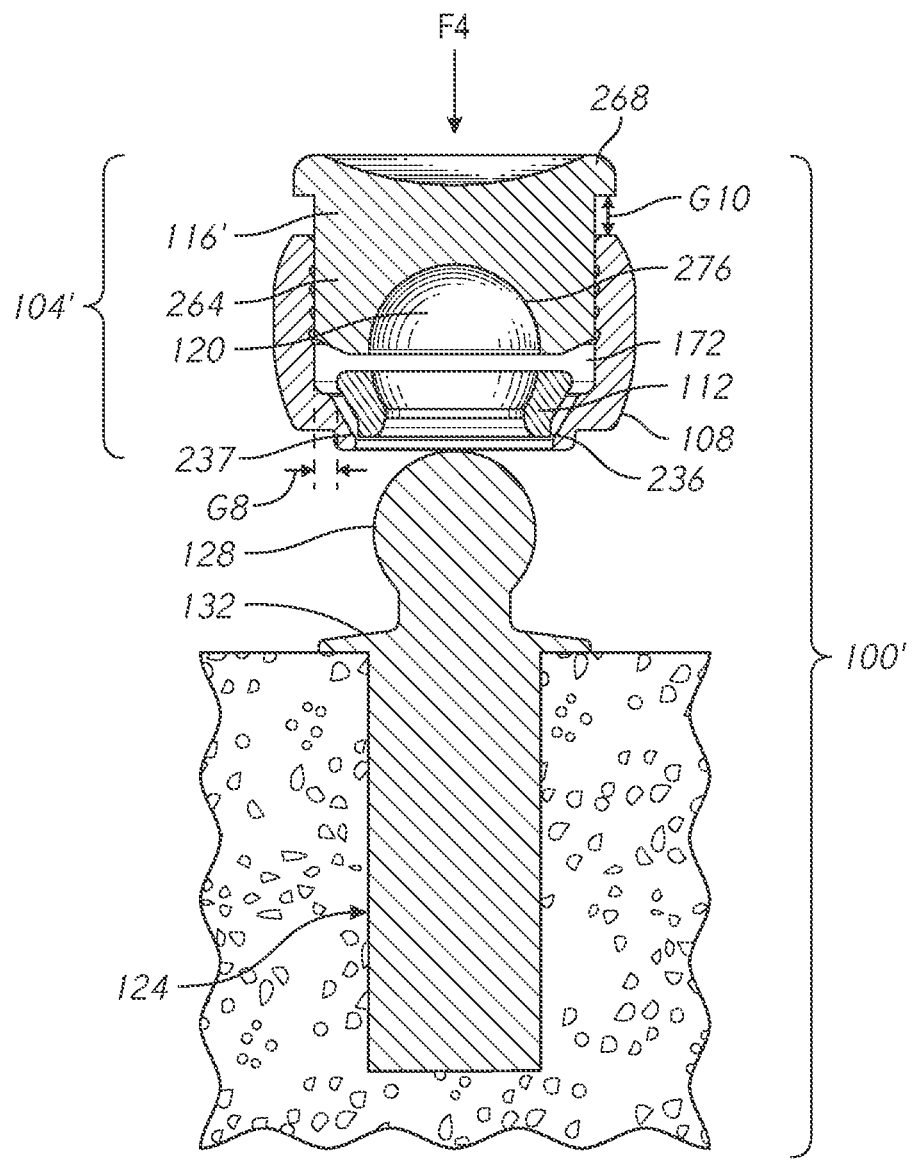
FIG. 23A is a schematic view illustrating a portion of a method of implanting a radial head assembly in a radius of a patient adjacent to an elbow joint.

In some instances, the articular assembly 104' is assembled in an unlocked configuration prior to implantation of the articular assembly 104' on the articular head 128, as shown in FIG. 23A. The articular member 116' may be partially inserted within the collar 108, thereby creating a gap G10 between a distal end face of a base 260 of the articular member 116' and a proximal end of the proximal portion 144 of the collar 108. The proximal portion 140 and at least a portion of the projection 264 can be exposed outside a proximal portion 144 of the collar 108. The portion of the projection 264 inserted within the collar 108 can be secured within the collar 108 through interaction with at least one of the collar connection feature 184 and the anti-rotational feature 188 (as shown and described in connection with FIGS. 7 and 8). In some embodiments, as shown in FIG. 23A, the distal end surface 280 of the articular member 116' (see FIGS. 14 and 15) can be disposed at a location proximal to the distal end of the collar 108, which provides the locking ring 112 with a range of axial and radial motion within the interior of the collar 108. Alternatively, the articular member 116' may be sufficiently inserted into the collar 108 so that the distal end surface 280 abuts against the locking ring 112 when the locking ring 112 is in the free or unlocked configuration within the collar 118.

Figure 23B:
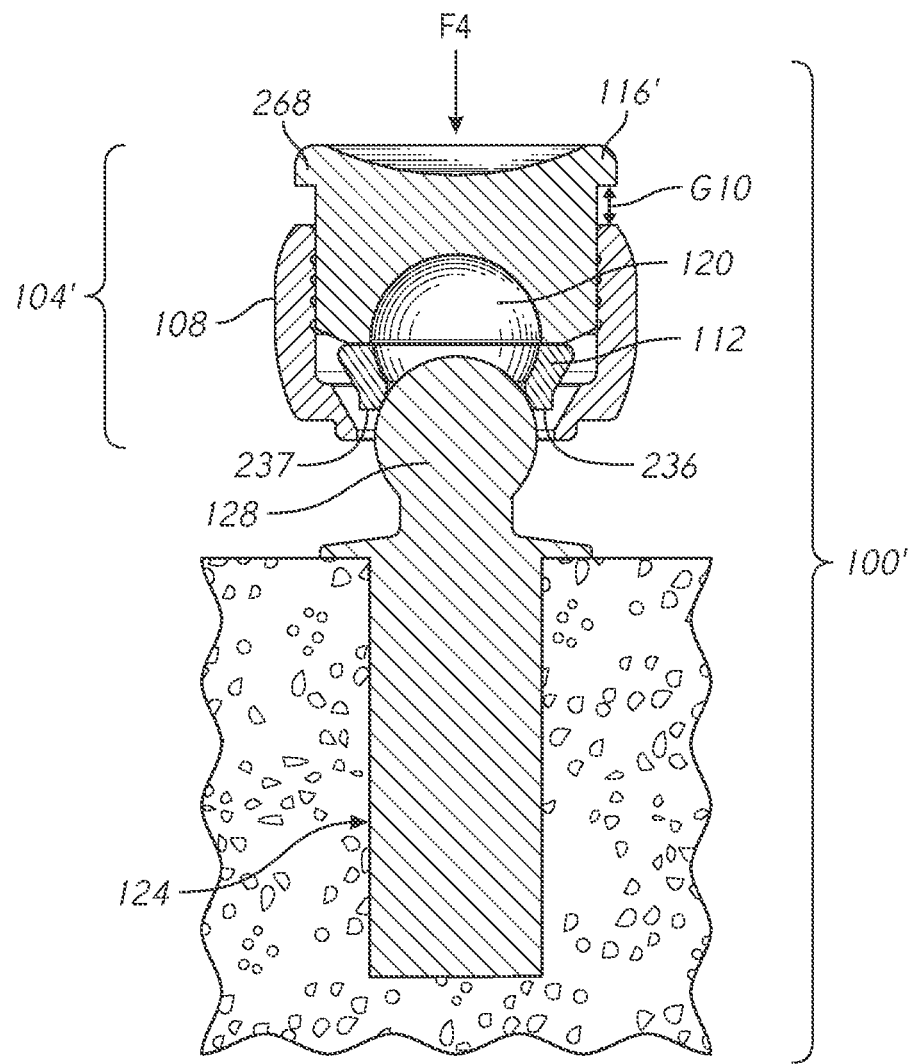
FIG. 23B illustrates a portion of a method of implanting a radial head assembly subsequent to the portion illustrated in FIG. 23A.
Figure 23E:
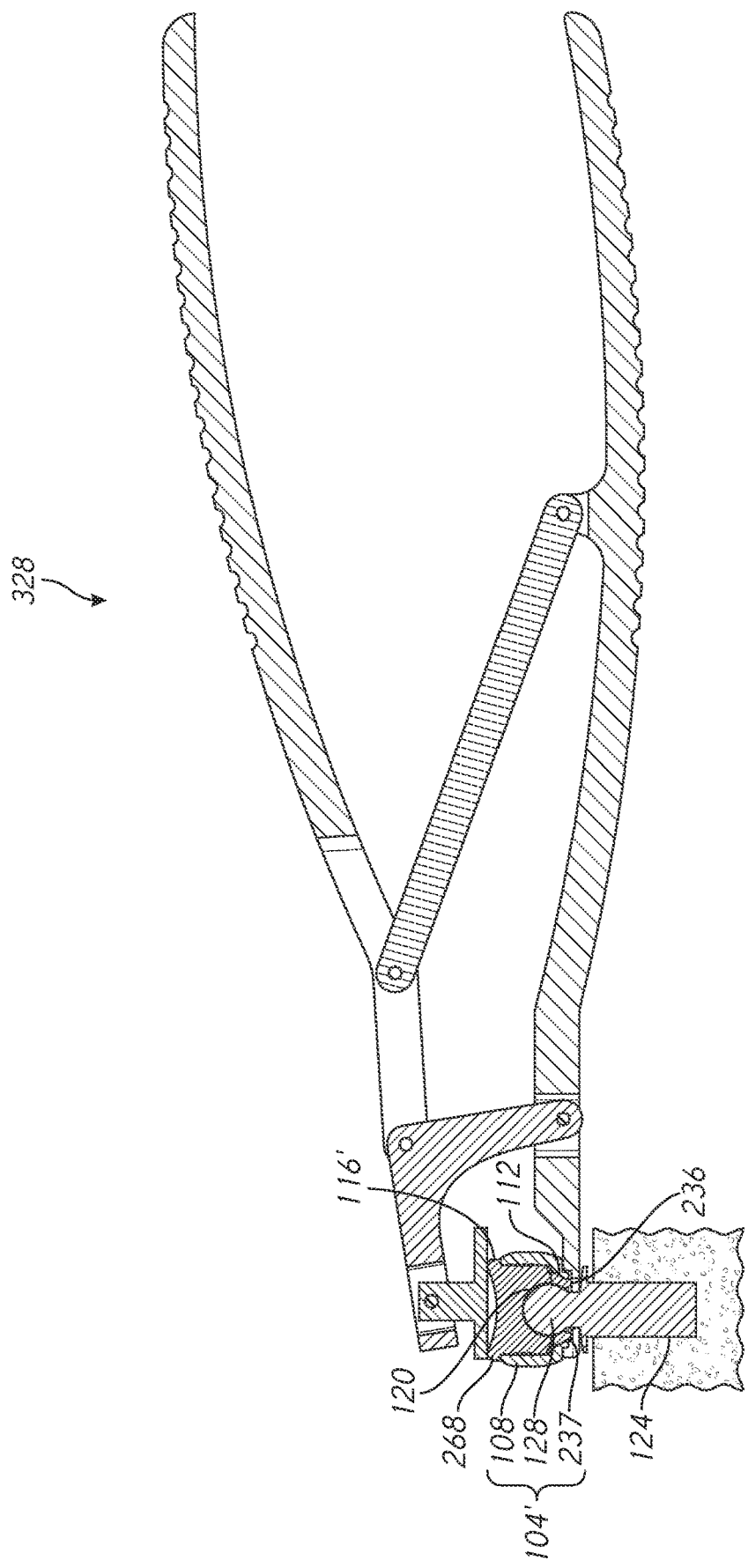
FIG. 23E illustrates a portion of a method of implanting a radial head assembly subsequent to the portion illustrated in FIG. 23C using the locking tool of FIG. 23D.

As discussed herein, the collar 108, locking ring 112, and the articular member 116' define an articular space 120 within the interior of the articular assembly 104' when the articular assembly 104' is assembled. To insert the articular head 128 into the articular space 120, the first collar opening 164 of the articular assembly 104' is placed on the articular head 128, as would be shown by axial movement of the articular assembly 104' onto the articular head 128 as illustrated in FIGS. 23A and 23B. The articular head 128 interacts with the distal portion 240 of the locking ring 112. The interaction with the articular head 128 may proximally advance the locking ring 112 within the collar 108 to a position abutting a distal end of the articular member 116', as illustrated in FIG. 23B. A force F4 in the direction of a longitudinal axis of the articular head 128 can be applied to the articular assembly 104'. The force F4 may cause the articular assembly 104' to engage the articular head 128 and compress the locking ring 112 between the articular member 116' and the articular head 128. As force F4 is applied the articular head 128 may be advanced to within the ring opening 224 and may then cause the locking ring 112 to expand. The slot 232 permits the two free ends 233 to move toward and away from each other. As such, the inner diameter D of the locking ring 112 (see FIGS. 9 and 10) is increased within the space provided by gap G8 or decreased as discussed further below. The expansion of the locking ring 112 permits the articular head 128 to be advanced through the increased diameter D of the locking ring 112. Once inserted through the locking ring 112, the articular head 128 is disposed in the articular space 120 between the locking ring 112 and the second concave surface 276. The locking ring 112 is disposed between the articular head 128 and the angular portion 176 (see FIGS. 7 and 8) of the interior collar surface 172, as illustrated in FIG. 23C.

FIGS. 23C-23E illustrates a method for placing the locking ring 112 in the locked configuration through use of the locking tool 328 shown in FIG. 23D. When the articular head 128 is disposed within the articular space 120, compressive forces F10, F10' (see FIG. 23C) can be applied between a distal end face of the collar 108 and a proximal end of the articular assembly 116' to position the radial head assembly 100' in the locked configuration. A compressive force F10, and a corresponding equal and opposite reactionary force F10', can be applied to the articular assembly 104'. The compressive forces F10, F10' causes the articular member 116' to move in a distal direction relative to the collar 108 and to interface with the locking ring 112. As the compressive forces F10, F10' are applied, the articular member 116' and the locking ring 112 may distally advance relative to collar 108 and cause the locking ring 112 to move to a position adjacent to the first collar opening 164. The angular outer surface 228 of the locking ring 112 can engage the angular portion 176 of the interior collar surface 172. Movement of the articular member 116' and the locking ring 112 distally decreases the gap G8 between locking ring 112 and the interior collar surface 172. As the gap G8 decreases, the ability of the locking ring 112 to expand decreases. This prevents the stem 124 from being inadvertently dislodged from the articular assembly 104'.

In some embodiments, upon continued application of the compressive forces F10 and F10', the projection 264 can be advanced into the collar 108 with the outer rim 268 acting as a positive stop upon insertion of the articular member 116' into the collar 108. The projection 264 of the articular member 116' may have a sufficient length to cause a distal portion 150 of the locking ring 112 to enter the locked configuration disposed distal to the first collar opening 164 when the outer rime 268 of the articular member 116' engages a proximal surface of the collar 108. The at least one ring connection feature 236 can engage the collar wall 160 to retain the locking ring 112 in the collar 108. As described previously, the ring connection feature 236 can include a groove or flange that can be configured to inhibit disengagement of the locking ring 112 from the collar 108. The collar wall 160 can confine the locking ring 112 and inhibit expansion of the locking ring 112 when in the locked configuration. The locked configuration prevents the articular head 128 from passing through the locking ring 112 and disengaging the articular assembly 104'. The locked configuration still allows bipolar articulation, however, providing a great degree of movement to provide natural or near natural joint motion in a prosthesis employing the radial head assembly 100.

B. Methods of Removing an Articular Assembly

As discussed above, the articulation and radial head assembles disclosed herein provide extremely secure connection. Disassembly is facilitated by advantageous features, as well. It may become necessary to remove the radial head assembly 100 from the articular head 128, for example, if the radial head assembly 100 begins to wear.

FIG. 21 shows a surgical method for removing an elbow joint prosthesis system. In the method, an articular assembly 104 is fully assembled and engaged in the locked configuration with the stem 124. When in the locked configuration, a distal end 150 of the locking ring 112 is disposed distal to and engaged with the collar wall 160. At least one ring connection feature 236, e.g. a groove or flange, may engage a distal end surface of the collar wall to retain the locking ring 112 within the first collar opening 164, as previously discussed. The locking ring 112 is contained by the collar wall 160, inhibiting the locking ring 112 to expand.

The removal tool 324 may be used to disengage the locking ring 112 from the collar wall 160. The removal tool 324 can be configured such that the projection 326 at a distal portion thereof can be inserted through the aperture 180 within the collar wall 160 to disengage the locking ring 112. The removal tool 324 can apply a compressive force F1 (as shown in FIGS. 8, 11, and 21) through the aperture 180. The compressive force F1 may act upon at least one of the ring connection feature 236, the slot 232, free ends 233 of the ring 112, and the ring wall 220 to compress the locking ring 112. Application of the compressive force F1 may decrease a distance between the two free ends 233 of the locking ring 112. As the two free ends 233 move closer to each other, a diameter of the locking ring 112 decreases and the locking ring 112 may disengage from the collar wall 160. FIGS. 21A and 22 show that the removal tool 324 can act on the articular member 116 in some embodiments to hold the articular assembly 104 stationary such that the force F1 is focused on the locking ring 112. FIG. 22 shows that the projection 326 can be formed on a tapered or wedge shaped distal end of one arm of the removal tool 324. The tapered or wedge shape of the distal end enables the tool 324 to be urged into the space between the annular member 132 and the locking ring 112. Once disengaged from the collar wall 160, the locking ring 112 may be advanced proximally within the collar 108 from the locking configuration to the free configuration. As discussed above in reference to FIG. 20A, gap G8 may be disposed between the ring wall 220 and the interior collar surface 172. The free configuration permits the locking ring 112 to expand and allow the articular head 128 to pass through the locking ring 112. As such, the articular assembly 104 may be removed from the stem 124.

Although this method is described in the context of the radial head assembly 100 shown in FIGS. 2-15, a similar method can be used to implant the radial head assemblies 400, 480 shown in FIGS. 17-19.

Terminology

Although certain embodiments have been described herein, the implants and methods described herein can interchangeably use any articular component, as the context may dictate.

As used herein, the relative terms "proximal" and "distal" shall be defined from the perspective of the radial head assembly.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1" includes "1." Phrases preceded by a term such as "substantially," "generally," and the like include the recited phrase and should be interpreted based on the circumstances (e.g., as much as reasonably possible under the circumstances). For example, "substantially spherical" includes "spherical." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y and at least one of Z to each be present.

Although certain embodiments and examples have been described herein, it should be emphasized that many variations and modifications may be made to the elbow joint prosthesis shown and described in the present disclosure, the elements of which are to be understood as being differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, it will be understood by those skilled in the art that the scope of the inventions extends beyond the specifically disclosed embodiments to any and all embodiments having equivalent elements, modifications, omissions, combinations or sub-combinations of the specific features and aspects of the embodiments (e.g., of aspects across various embodiments), adaptations and/or alterations, and uses of the inventions as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Any methods disclosed herein need not be performed in the order recited. The methods disclosed herein include certain actions taken by a practitioner; however, they can also include any third-party instruction of those actions, either expressly or by implication. For example, actions such as "placing an opening of an articular assembly on the articular head" include "instructing placement of an opening of an articular assembly on the articular head."

What is claimed is:

1. A radial head system comprising:
a collar comprising a collar wall defining a first collar opening, a second collar opening, and a passage therethrough, the collar wall having an interior collar surface comprising a collar engagement feature proximate to the first collar opening;
an articular member comprising:
a first concave surface; and
a second concave surface disposed at an end of the articular member opposite to the first concave surface; and
a peripheral surface configured to be disposed between the first concave surface and the second concave surface when the peripheral surface is disposed within the interior collar surface;
wherein the articular member at least partially defines an articular space within the collar when disposed in the collar;
an articular head component configured to be disposed within the articular space; and
a stem that is configured to engage the articular head component.

2. The radial head system of claim 1, wherein the stem includes a distal end portion that engages the articular head component.

3. The radial head system of claim 2, wherein the articular head component includes a concave surface disposed on a distal face of the articular head component, and an external mating surface,
wherein the concave surface of the articular head component is located between the external mating surface of the articular head component and a distal end of the articular head component opposite the external mating surface, and is configured to receive at least a portion of the distal end portion of the stem.

4. The radial head system of claim 1, further comprising a locking ring comprising a ring wall defining a ring opening, the ring wall being configured to radially expand.

5. The radial head system of claim 4, wherein the articular space is at least partially defined by one of the concave surfaces of the articular member and the locking ring, and/or the collar.

6. The radial head system of claim 4, wherein the articular member and the locking ring are configured to abut the articular head component when the articular head component is inserted into the articular space.

7. The radial head system of claim 4, wherein the external mating surface is configured to engage the first collar opening and to inhibit removal of the locking ring from the collar.

8. The radial head system of claim 3, wherein the external mating surface comprises a convex surface configured to be positioned within the articular space, and wherein the external mating surface is configured to engage the second concave surface of the articular member and an internal engagement surface of the locking ring.

9. The radial head system of claim 1, wherein the collar engagement feature comprises one or more threads.

10. The radial head system of claim 1, wherein the collar comprises a first collar portion and a second collar portion.

11. The radial head system of claim 10, wherein the first collar portion comprises the collar engagement feature, wherein the second collar portion comprises a second collar engagement feature, and wherein the collar engagement feature is configured to engage the second collar engagement feature to prevent removal of at least a portion of a stem from the articular space.

12. The radial head system of claim 10, wherein each of the first collar portion and the second collar portion has a collar wall that extends between an outer periphery of each of the collar portions and an inner periphery of each of the collar portions.

13. The radial head system of claim 10, wherein the second collar portion is configured to interface with and/or to abut against a locking ring and a portion of the articular member when the locking ring and/or articular member is inserted into the second collar portion.

14. The radial head system of claim 10, wherein a proximal portion of the second collar portion defines an inner diameter of the proximal portion having a dimension that is greater than an outer periphery of a locking ring.

15. The radial head system of claim 10, wherein the first collar portion is configured to removably engage the second collar portion to transition from an unlocked configuration to a locked configuration of the radial head assembly when a locking ring, the articular member, and the articular head are at least partially inserted within the first collar portion and/or the second collar portion.

16. The radial head system of claim 10, wherein each of the first collar portion and the second collar portion includes at least one collar engagement feature that protrude from and/or be receded within the collar wall of each of the respective collar portions.

17. The radial head system of claim 16, wherein the at least one collar engagement feature can be a peg, a barb, a screw, or other protruding structure, configured to engage the other collar engagement features by a screw fit, a snap fit, or an interference fit.

18. The radial head system of claim 16, wherein the at least one collar engagement feature can include an external concave structure that can receive an external convex structure of the other collar engagement feature.

19. The radial head system of claim 16, wherein each of the collar engagement features can include one or more screw threads configured to engage with the one or more screw threads of the other collar engagement feature.

* * * * *